(12) United States Patent
Goto et al.

(10) Patent No.: US 7,505,550 B2
(45) Date of Patent: Mar. 17, 2009

(54) RADIOTOMOGRAPHY APPARATUS

(75) Inventors: Taiga Goto, Kashiwa (JP); Osamu Miyazaki, Moriya (JP); Koichi Hirokawa, Kashiwa (JP); Hiroto Kokubun, Kashiwa (JP)

(73) Assignee: Hitachi Medical Corporation, Tokyo (JP)

( * ) Notice: Subject to any disclaimer, the term of this patent is extended or adjusted under 35 U.S.C. 154(b) by 62 days.

(21) Appl. No.: 11/629,756

(22) PCT Filed: Jun. 15, 2005

(86) PCT No.: PCT/JP2005/010953
§ 371 (c)(1),
(2), (4) Date: Dec. 14, 2006

(87) PCT Pub. No.: WO2005/122901
PCT Pub. Date: Dec. 29, 2005

(65) Prior Publication Data
US 2007/0189436 A1 Aug. 16, 2007

(30) Foreign Application Priority Data

| | | | |
|---|---|---|---|
| Jun. 16, 2004 | (JP) | | 2004-177903 |
| Jul. 14, 2004 | (JP) | | 2004-206814 |
| Oct. 19, 2004 | (JP) | | 2004-304357 |
| Dec. 13, 2004 | (JP) | | 2004-359873 |

(51) Int. Cl.
*A61B 6/00* (2006.01)

(52) U.S. Cl. ............................................. 378/4; 378/8

(58) Field of Classification Search ...................... 378/4, 378/8
See application file for complete search history.

(56) References Cited

U.S. PATENT DOCUMENTS 6,233,478 B1 * 5/2001 Liu ............................. 600/428

(Continued)

FOREIGN PATENT DOCUMENTS

DE 10251448 5/2004

(Continued)

OTHER PUBLICATIONS

Bruder et al., Segmented Cardiac Volume Reconstruction—A Novel Reconstruction Scheme for Multislice Cardiac Spiral CT, 3D-2001 Presentations, 2001, http://citeseer.ist.psu.edu/cache/papers/cs/25353/http:zSzzSzcfi.lbl.govzSz3D-2001zSzabstractszSz07-12.pdf/segmented-cardiac-volume-reconstruction.pdf.*

(Continued)

*Primary Examiner*—Edward J Glick
*Assistant Examiner*—Alexander H Taningco
(74) *Attorney, Agent, or Firm*—Cooper & Dunham, LLP

(57) ABSTRACT

A radiotomograph comprises radiation detecting means which applies radiation from a radiation source to a subject from many direction and detects radiation transmitted through the subject from the directions, a bed on which the subject lies and which can move the subject in the direction of the body axis of the subject, reconstruction parameter setting means which sets reconstruction parameters including the amount of movement of the bed in the direction of the body axis and used to reconstruct, an image of the subject, reconstruction view area calculating means which calculates the reconstruction view area for at least one data segment necessary for reconstruction calculation determined for each position in a space reconstructed according to the set reconstruction parameters, reference segment position setting means which sets a reference segment position in the calculated reconstruction view area according to a phase signal generated by dynamic state analysis of the subject, effective segment calculating means which calculates an effective segment from the data segment containing the set reference segment position using a predetermined weight function, and image creating means for creating an image by reconstructing the calculated effective segment. With this, a radiotomograph both having an improved time resolution and enabling reduced effective radiation exposure can be provided.

31 Claims, 49 Drawing Sheets

U.S. PATENT DOCUMENTS

| | | | |
|---|---|---|---|
| 6,370,217 B1 * | 4/2002 | Hu et al. | 378/8 |
| 6,522,712 B1 * | 2/2003 | Yavuz et al. | 378/4 |
| 6,597,803 B1 | 7/2003 | Pan et al. | |
| 6,665,370 B2 * | 12/2003 | Bruder et al. | 378/15 |
| 6,763,082 B2 * | 7/2004 | Ozaki | 378/8 |
| 6,879,665 B1 * | 4/2005 | Cook et al. | 379/67.1 |
| 6,937,690 B2 | 8/2005 | Bruder et al. | |
| 7,079,618 B2 * | 7/2006 | Tsuyuki | 378/8 |
| 7,346,143 B2 * | 3/2008 | Manzke et al. | 378/15 |
| 2002/0136350 A1 * | 9/2002 | Pan et al. | 378/8 |
| 2003/0072419 A1 | 4/2003 | Bruder et al. | |
| 2004/0131140 A1 * | 7/2004 | Bruder et al. | 378/4 |
| 2004/0179644 A1 * | 9/2004 | Tsuyuki | 378/8 |
| 2005/0089133 A1 * | 4/2005 | Tsuyuki | 378/8 |
| 2005/0129176 A1 | 6/2005 | Kokubun et al. | |

FOREIGN PATENT DOCUMENTS

| | | |
|---|---|---|
| JP | 2001-170044 | 6/2001 |
| JP | 2002-3300961 | 11/2002 |
| JP | 2003-93378 | 4/2003 |
| JP | 2003-204961 | 7/2003 |
| JP | 2004-160222 | 6/2004 |
| JP | 2004-313513 | 11/2004 |

OTHER PUBLICATIONS

Stierstorfer et al., Weighted FBP—a simple approximate FBP algorithm for multislice spiral CT with good dose usage for arbitrary pitch, Physics in Medicine and Biology, 49, 2004, pp. 2209-2218.*

Stierstorfer et al., Segmented multiple plane reconstruction: a novel approximate reconstruction scheme for multi-slice spiral CT, Physics in Medicine and Biology, 47, 2002, pp. 2571-2581.*

Flohr et al., A retrospectively ECG-gated multislice spiral CT scan and reconstruction technique with suppression of heart pulsation artifacts for cardio-thoracic imaging with extended vol. coverage, 2002, European Radiology, vol. 12, pp. 1497-1503.*

* cited by examiner

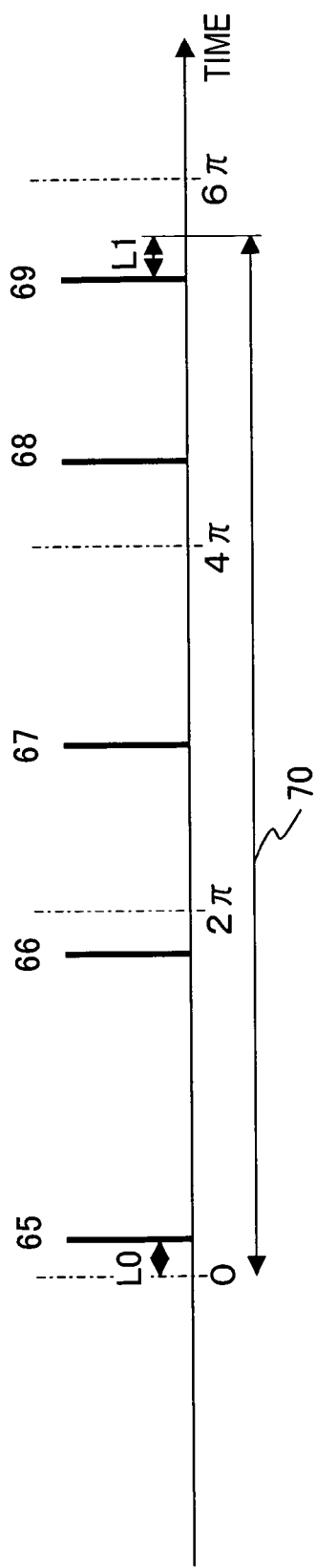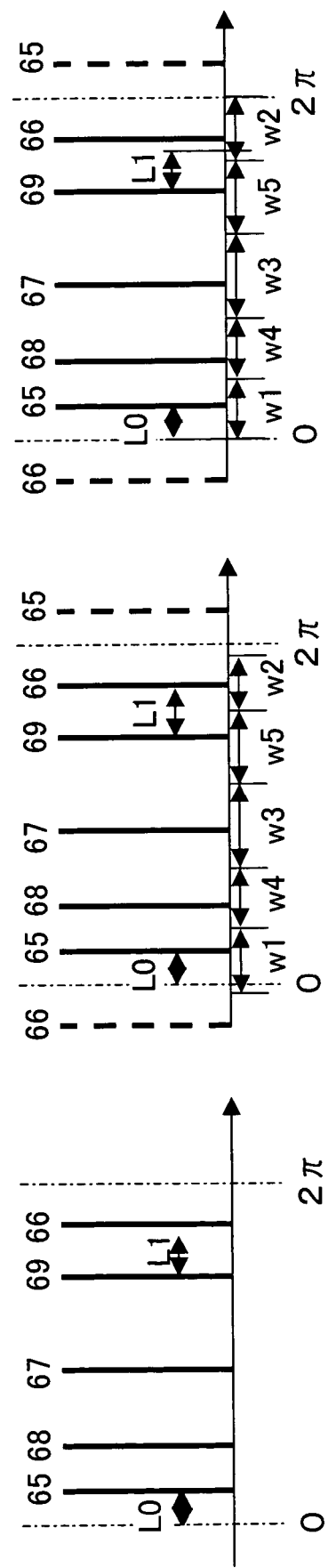

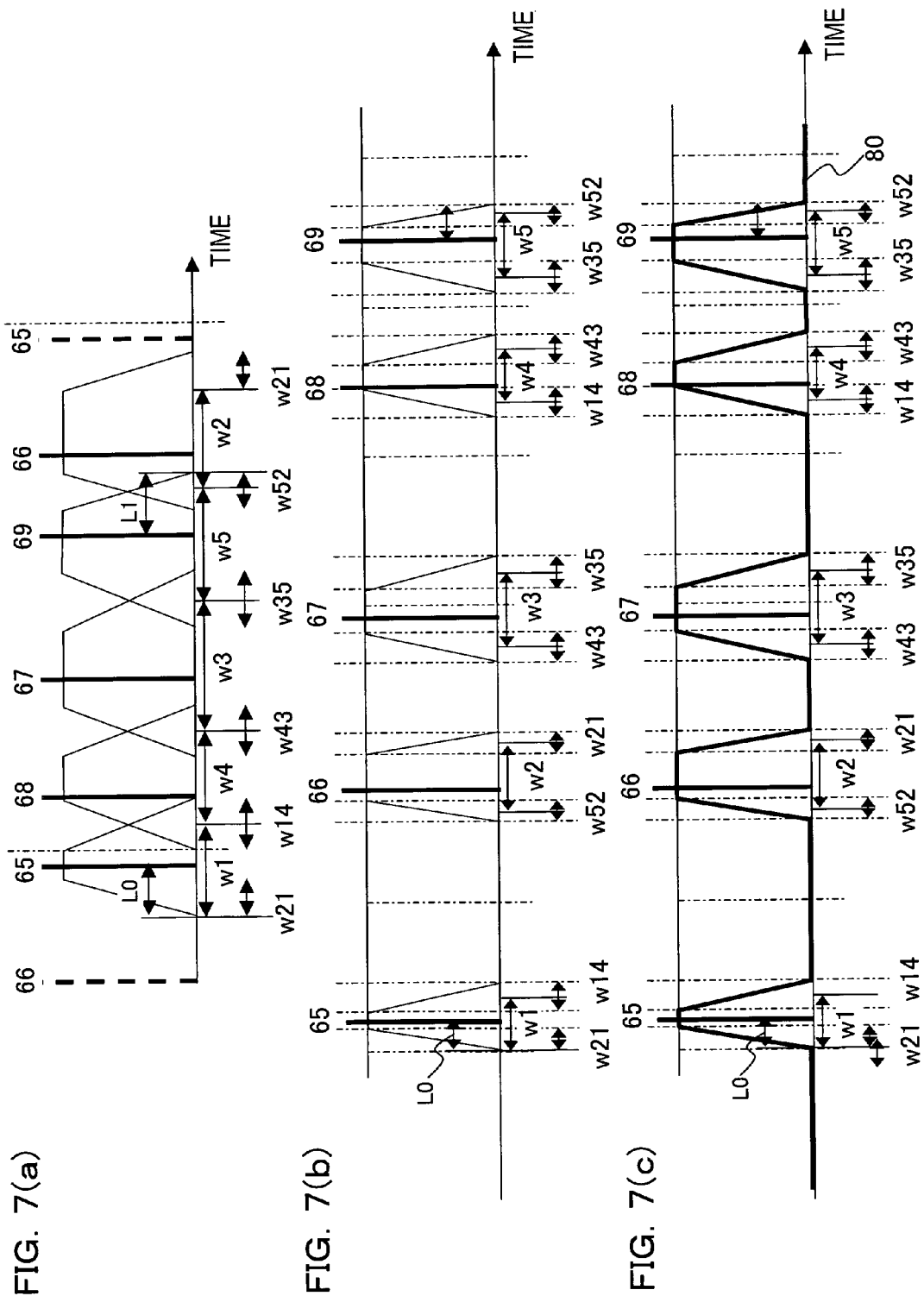

FIG. 8(a)   OVERLAP RATIO 100 %
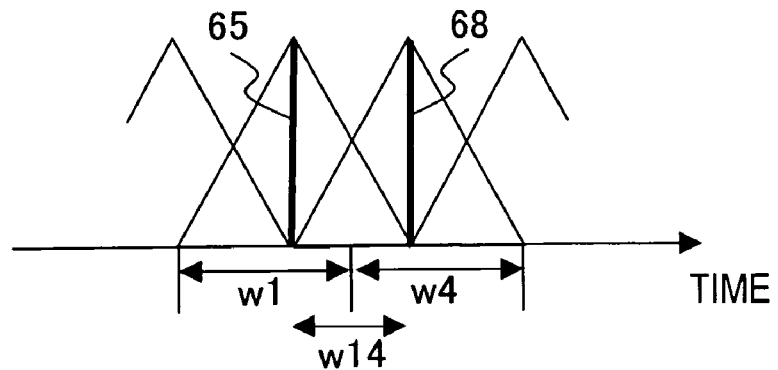
FIG. 8(b)   OVERLAP RATIO 50 %
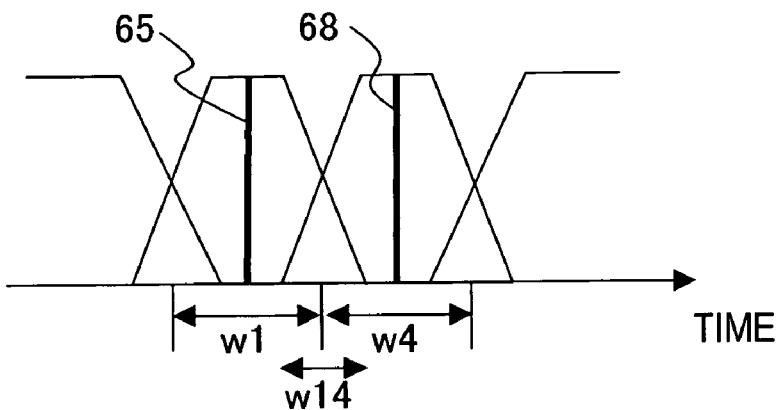
FIG. 8(c)   OVERLAP RATIO 0 %
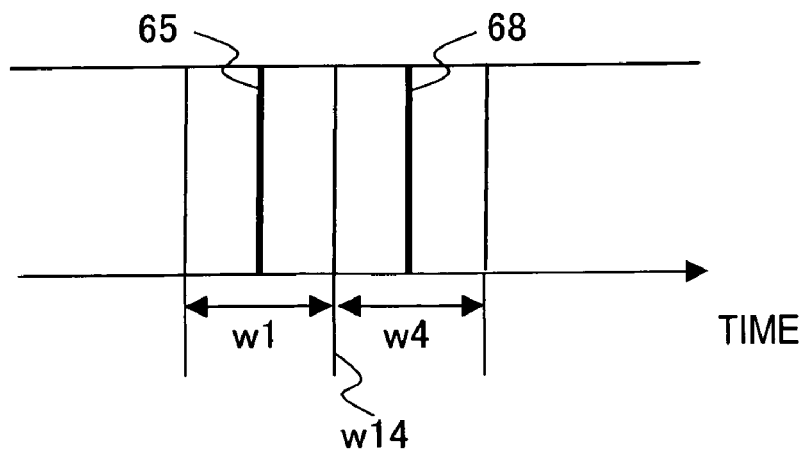

FAN BEAM

PALALLEL BEAM

FOCUS TRAJECTORY

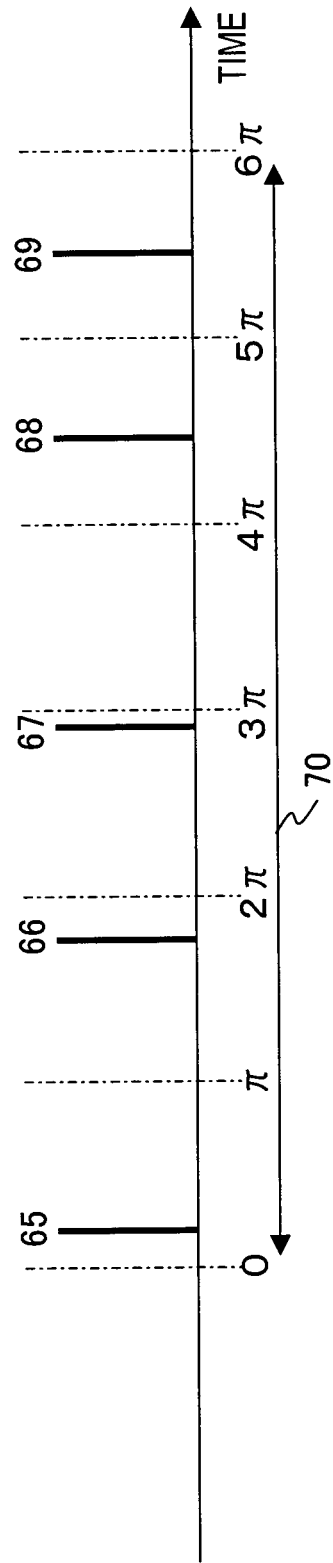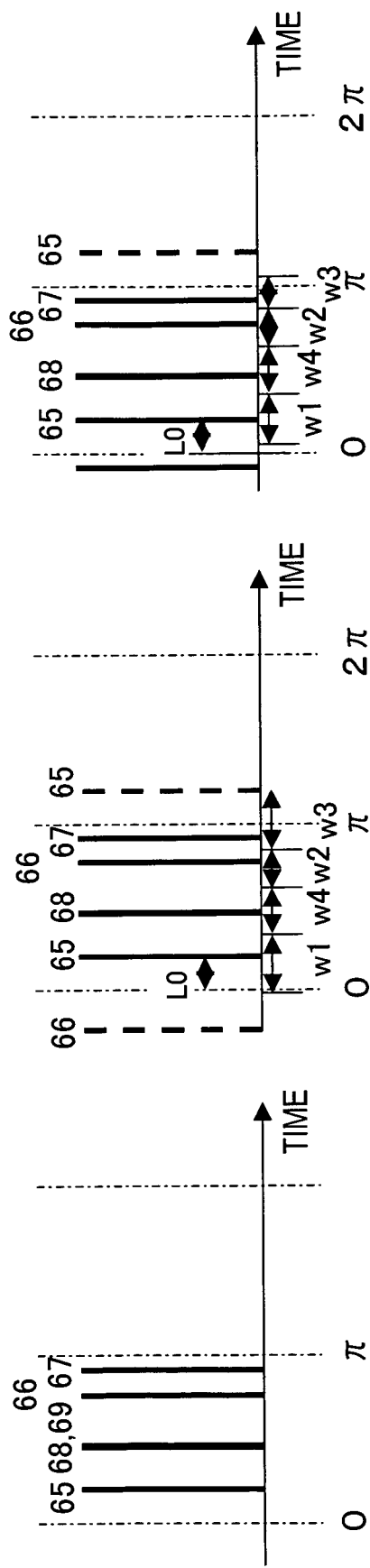

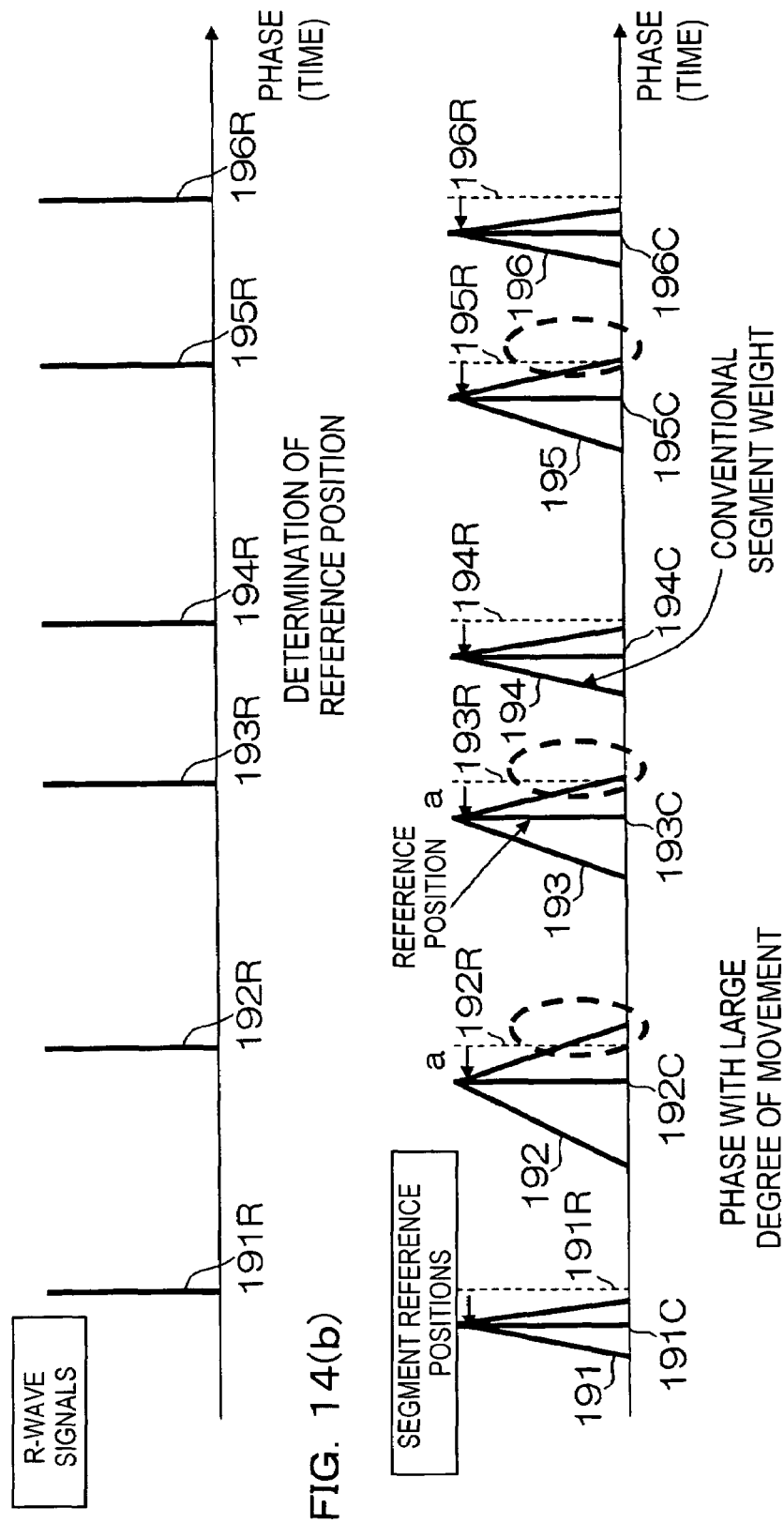

FOCUS TRAJECTORY

412 X-RAY DETECTOR

1ST ROW

X-RAY DETECTOR ARIGNMENT

8TH ROW  ....  3RD ROW  2ND ROW  1ST ROW

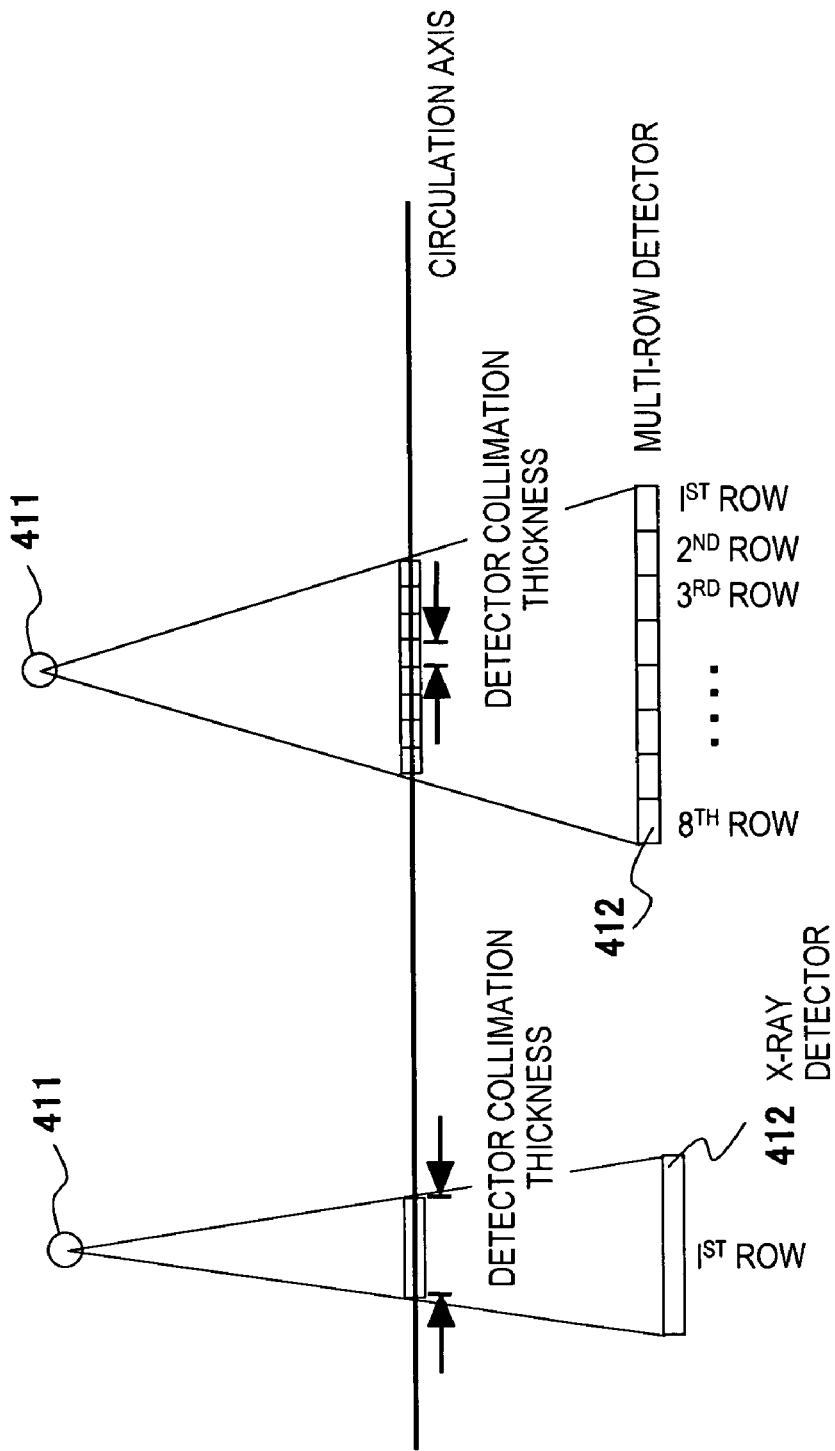

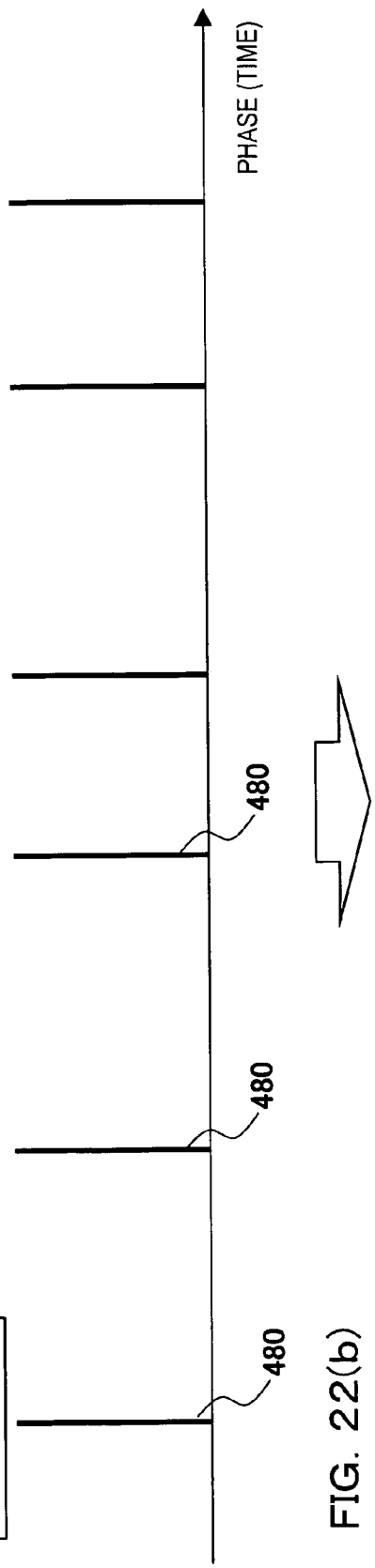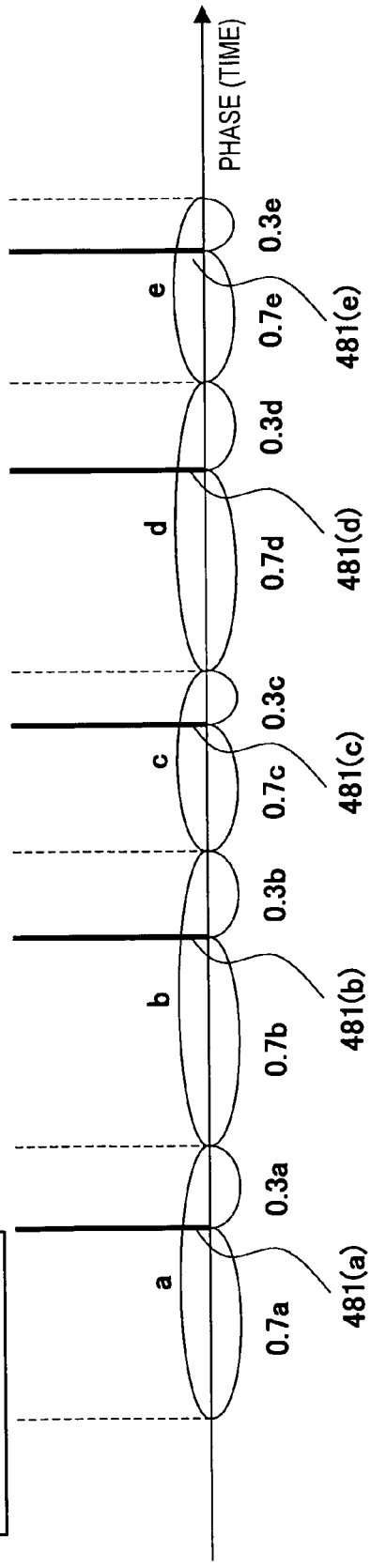

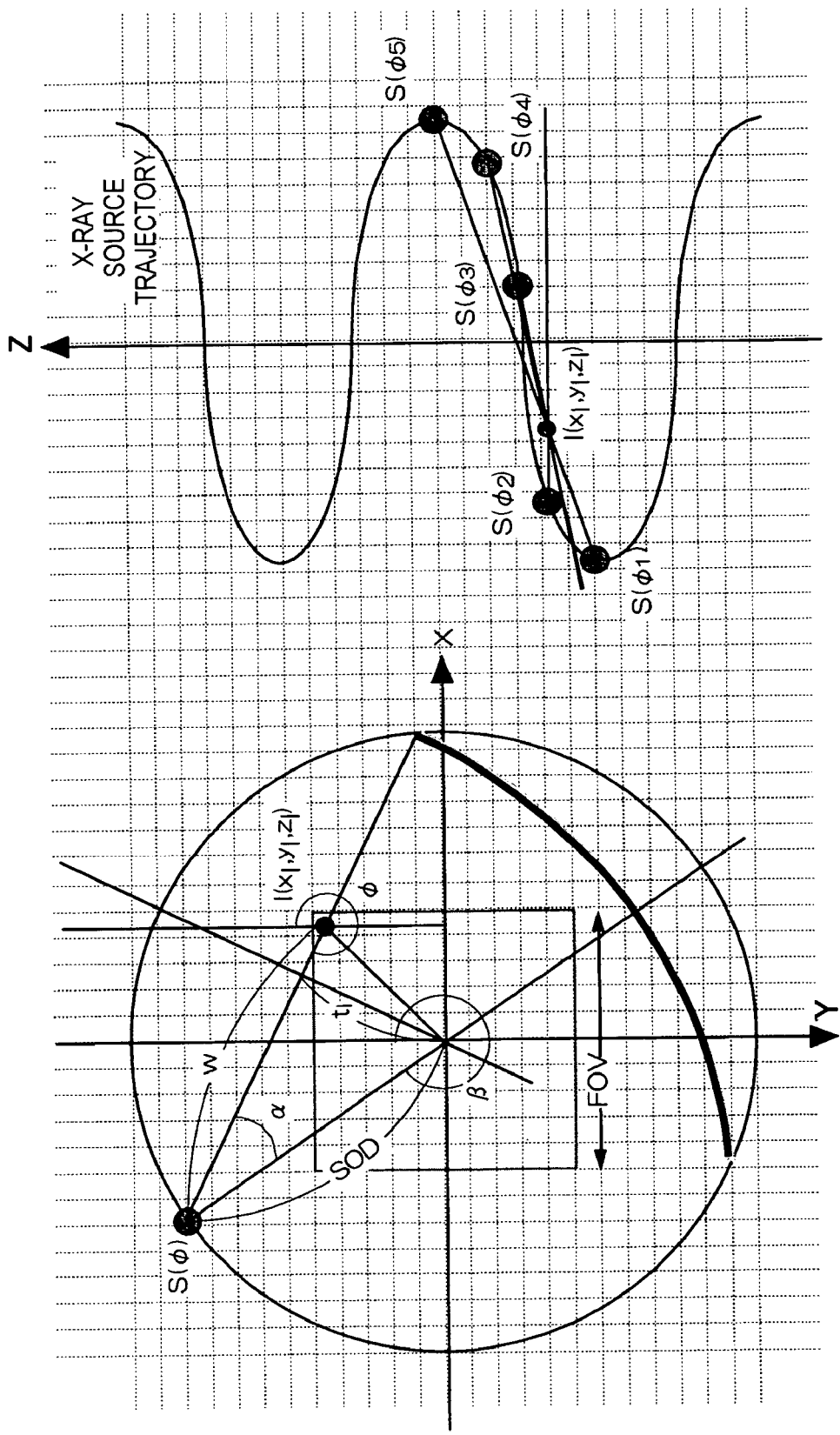

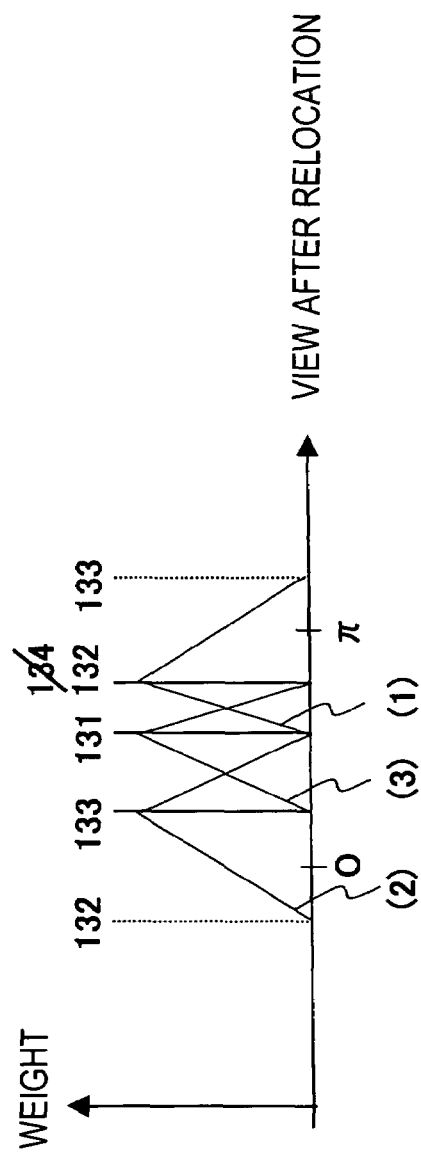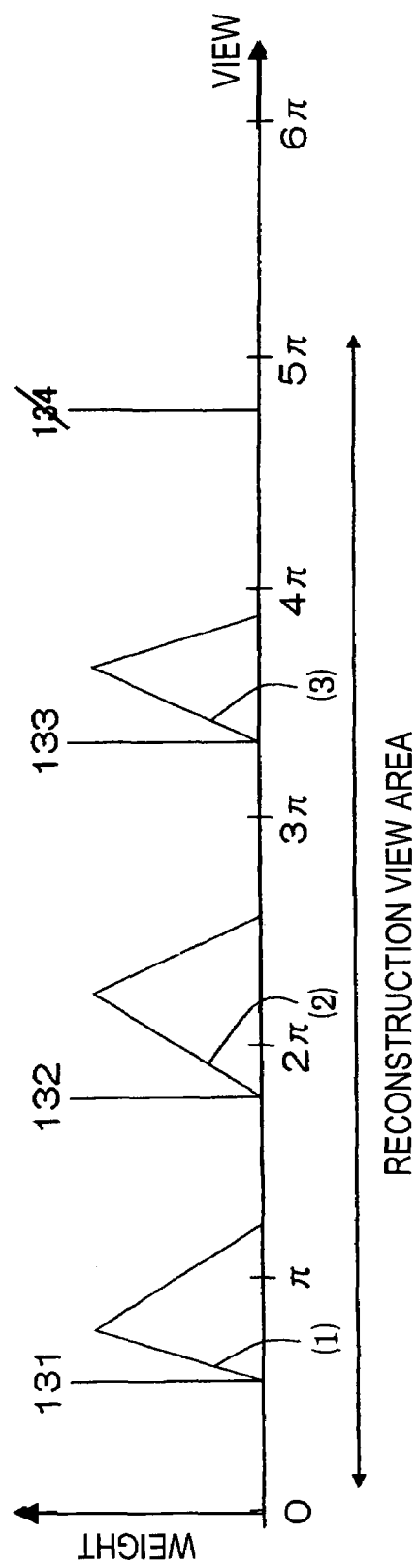
FIG. 27(a)
FIG. 27(b)

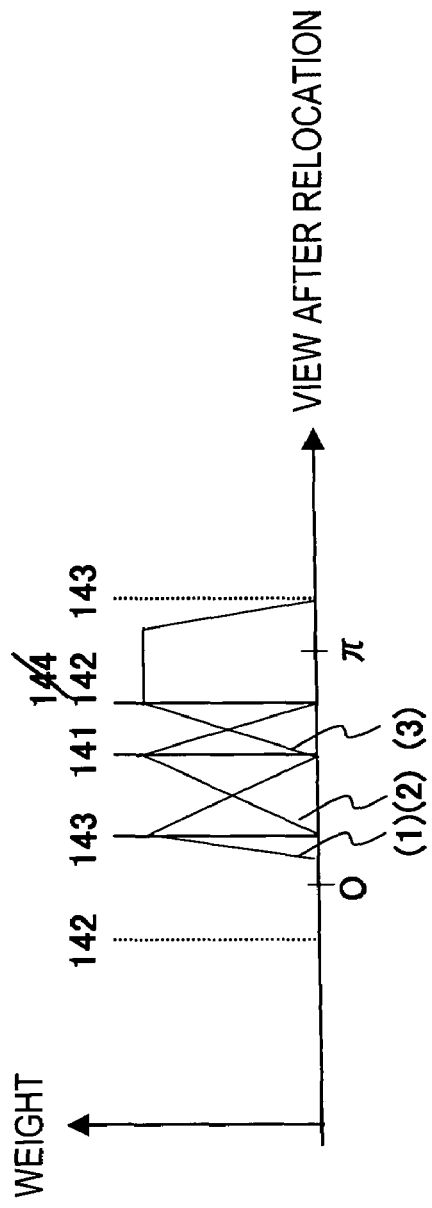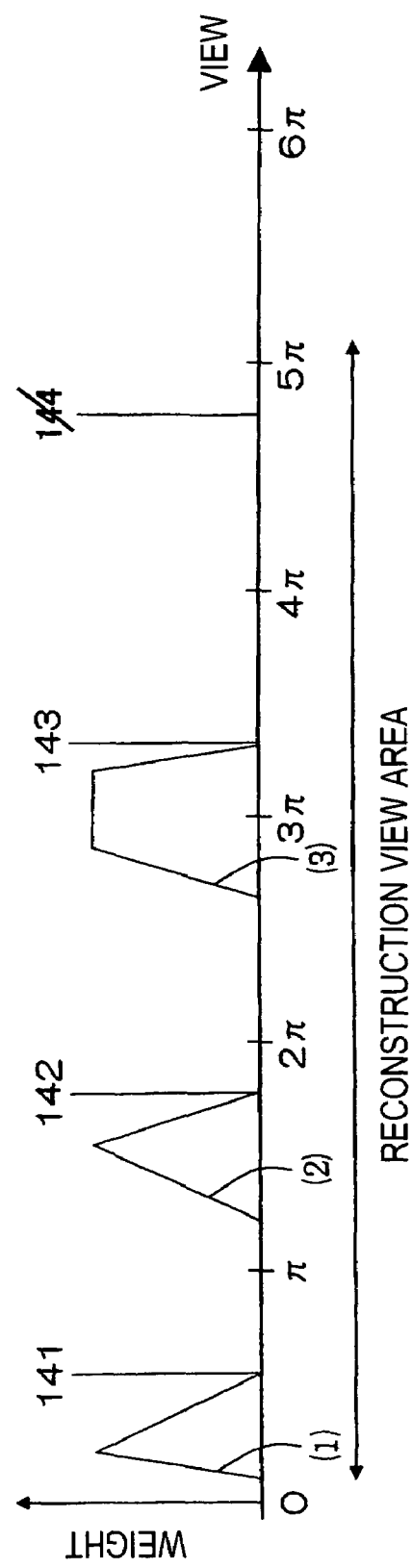
FIG. 28(a)
FIG. 28(b)

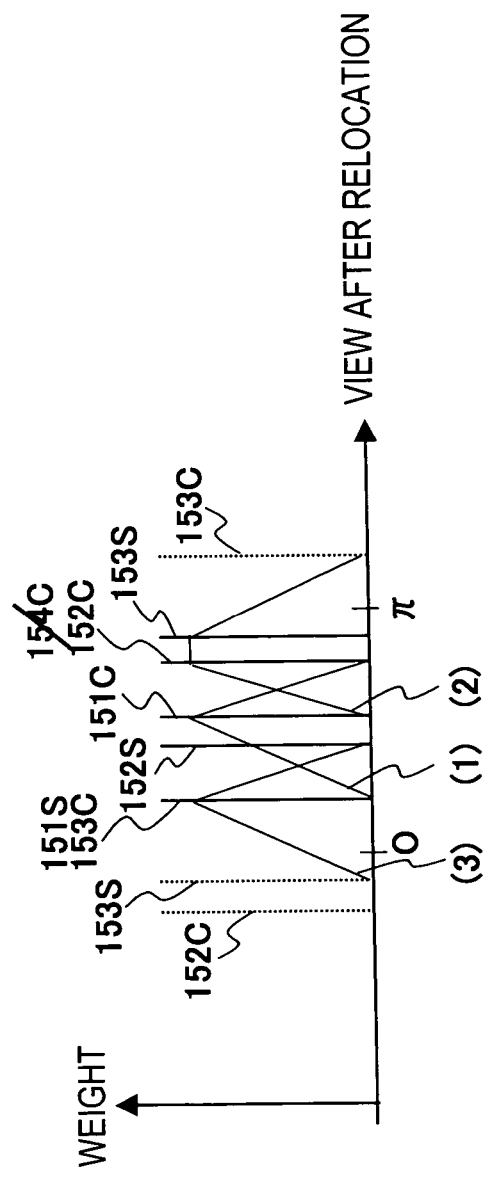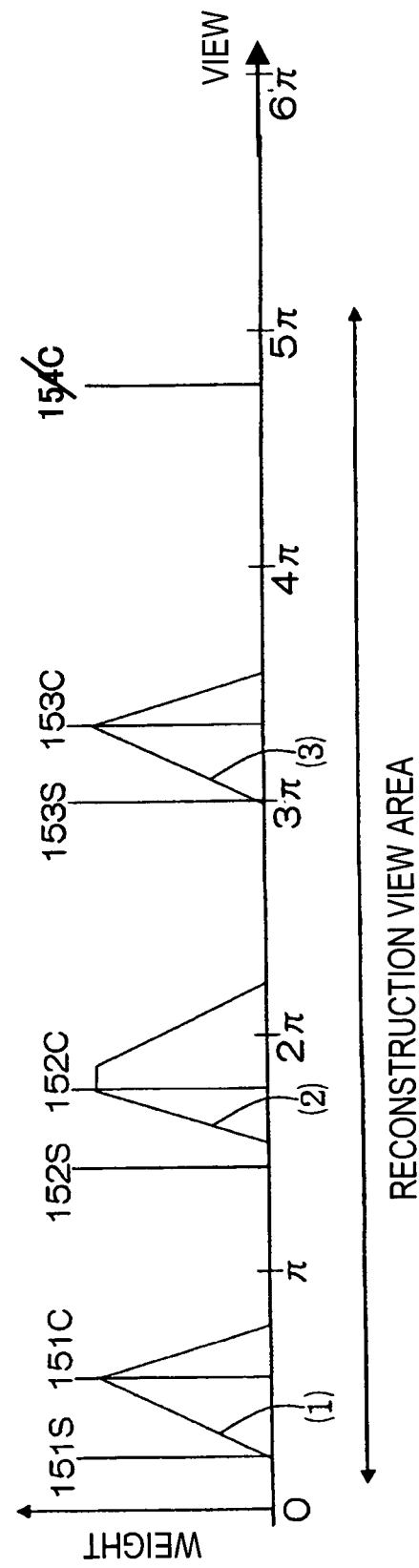

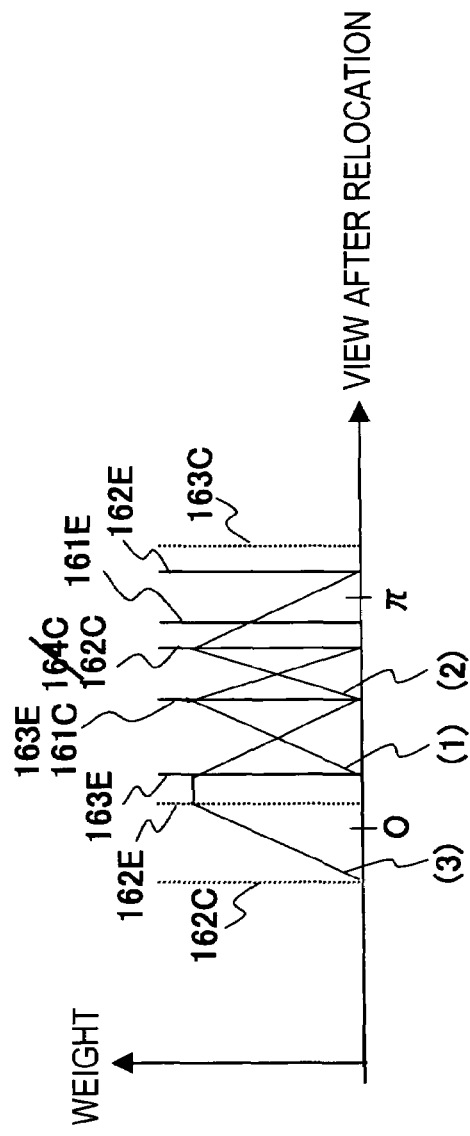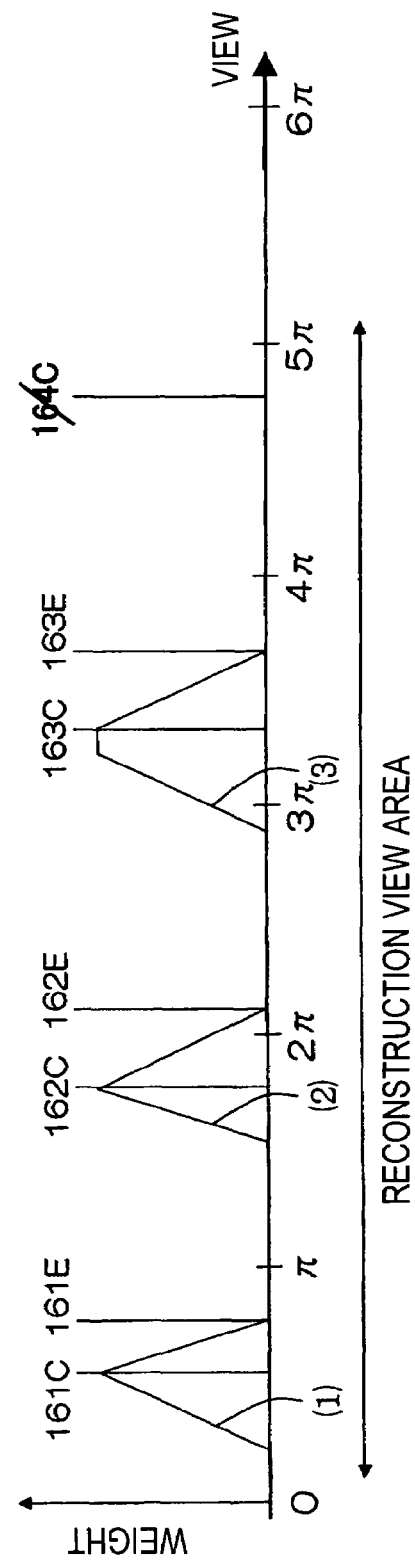

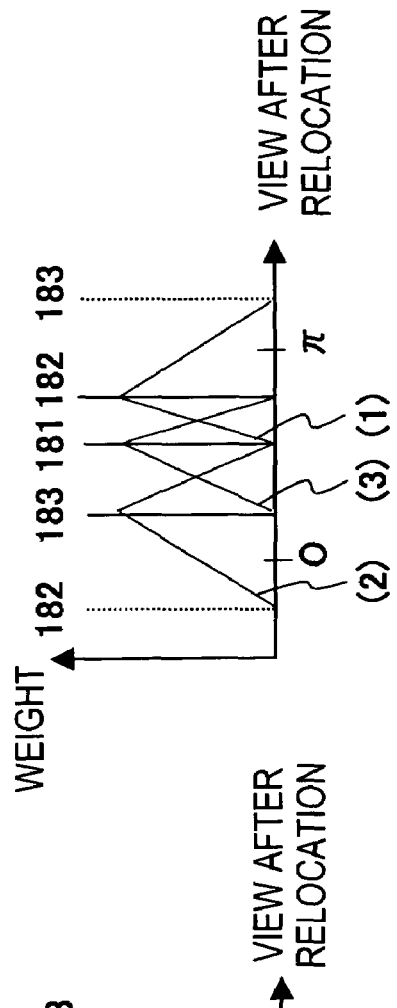
FIG. 32(a)
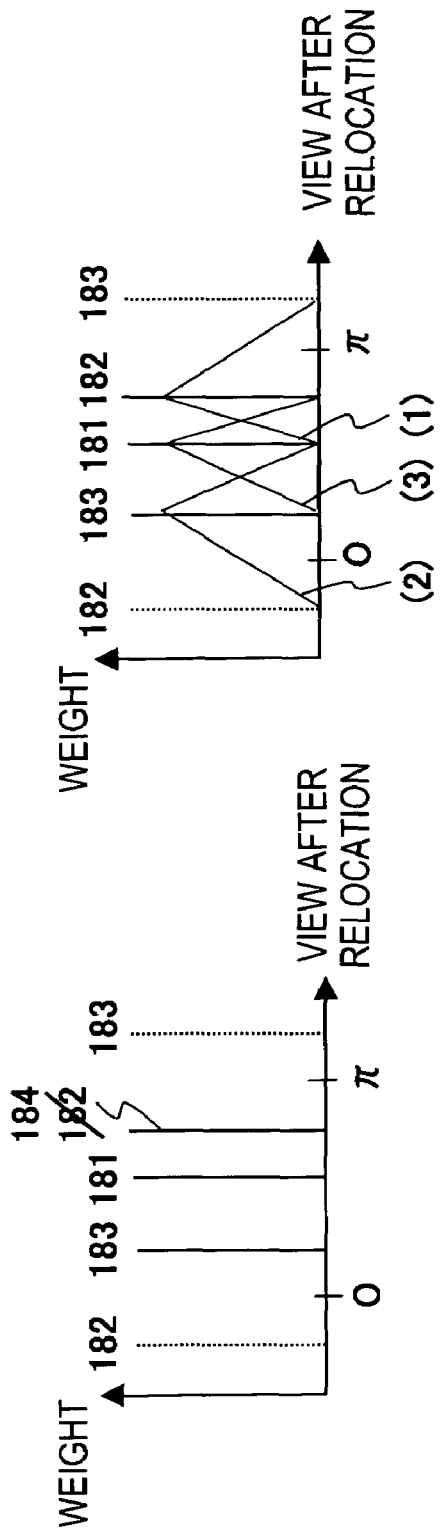
FIG. 32(b)
FIG. 32(c)

FIG. 33

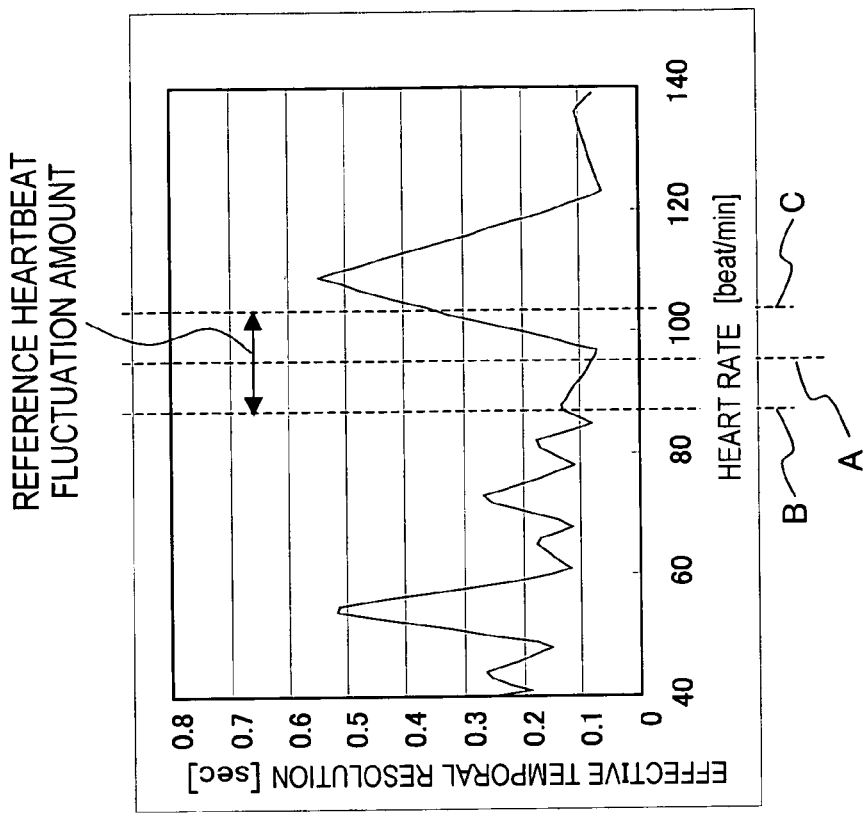
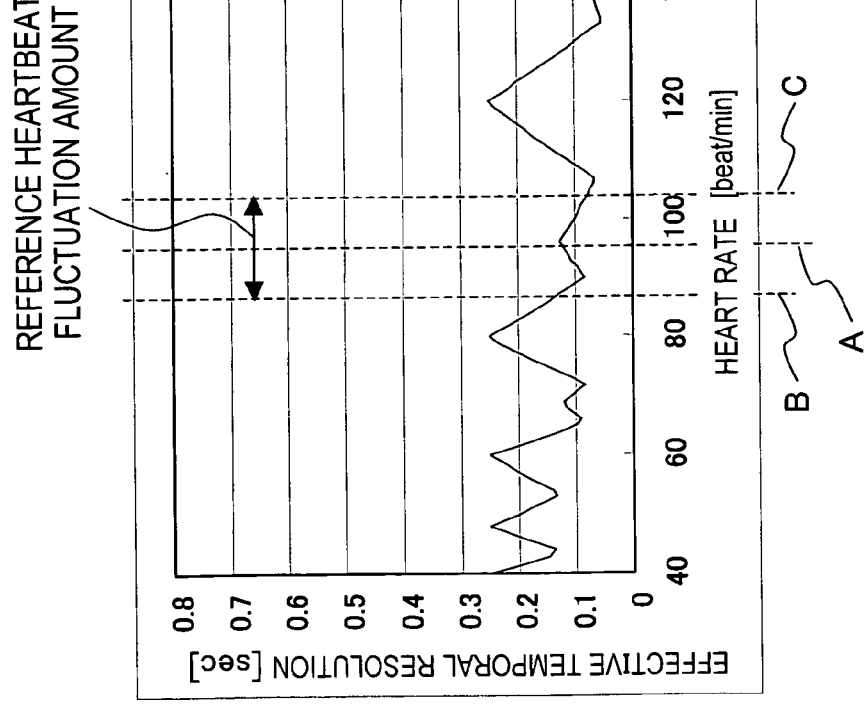

RADIOTOMOGRAPHY APPARATUS

TECHNICAL FIELD

The present invention relates to a radiotomography apparatus, and more particularly to a radiotomography apparatus for the purpose of scanning sites that carry out a periodic motion in an object to be examined, such as a cardiovascular region or respiratory organ.

The present application claims priority under the Paris Convention to Japanese Patent Application No. 2004-177903, Japanese Patent Application No. 2004-206814, Japanese Patent Application No. 2004-304357, and Japanese Patent Application No. 2004-359873 that are based on the Patent Law of Japan, the contents of which are incorporated herein by reference in their entirety to receive the benefit of these applications.

BACKGROUND ART

An X-ray CT apparatus is one kind of radiotomography apparatus. An X-ray CT apparatus irradiates X rays while rotating a rotating part equipped with an X-ray tube and an X-ray detector around the circumference of an object to be examined, and detects X rays that are transmitted through the body of the object with the X-ray detector.

With this kind of X-ray CT apparatus, cardiography is performed by arranging the cardiac X-ray transmission data for a desired cardiac phase according to the following method.

Data is collected so that the cardiac phase and the angle of the rotation direction (hereunder, referred to as "view angle") are not the same for each rotation.

Desired data is acquired from the above described collected "view angle" data by interpolation.

In this case, the term "desired cardiac phase" refers to, for example, immediately before a contraction phase in which the cardiac motion is comparatively stable. Since a tomogram can be constructed by collecting X-ray transmission data from at least a 180° direction around the object, the data of a desired cardiac phase is collected from a 180° direction or more while rotating the rotating part a plurality of times.

When performing the above described kind of cardiography with an X-ray CT apparatus, if a large number of projection images can be acquired at one time the X-ray transmission data can be obtained in a shorter scanning time. Collection of data in a short scanning time in this manner relates to the control of radiation exposure such as X rays, and is desirable for the object. Methods for acquiring a large number of projected images at one time include not only a view method, but also a method that uses X rays in the shape of a cone beam that spreads out in the direction of the body axis of the object. A plurality of X-ray detecting elements are disposed not only in the view direction that is the rotational direction, but also in the body axis direction that is the direction of the circulation axis, in correspondence to the plane of projection of the cone-beam X rays.

Patent Document 1 discloses technology that breaks down X-ray transmission data that includes a cardiac phase of interest into data segments using this type of cone-beam X-ray CT apparatus, and then combines a plurality of these data segments to reconstruct a cardiac tomogram at a certain section.

The term "data segment" refers to consecutive data that was obtained continuously in a view direction that includes X-ray transmission data for a certain cardiac phase, and the length in the circulation axis direction thereof and the length in the view direction depend on the scanning speed, the heart rate, the table feeding speed and the like.

In the case of cardiography performed by a helical scan using cone-beam X rays as disclosed in Patent Document 1, the number of data segments used to reconstruct a tomogram is fixed as the minimum number among the number of segments corresponding to each view angle area.

Patent Document 1: Japanese Patent Application Laid-Open No. 2003-93378

DISCLOSURE OF THE INVENTION

In Patent Document 1, since the number of segments corresponding to each view angle area is fixed as the minimum number, when the table feeding speed is fast, the length in the direction of the circulation axis and length in the view direction of data segments obtained within a predetermined time both increase and the number of data segments decreases. As a result, the temporal resolution declines.

In contrast, when the table feeding speed is slowed down to increase redundancy, since the number of segments used for reconstruction is fixed as the minimum number of data segments, the number of segments that are not used for reconstruction increases, the utilization rate of those segments falls, and there is a concern that ineffective radiation exposure of the object is increased.

A radiotomography apparatus according to the present invention comprises a radiation detection device that irradiates radiation from a radiation source in multiple directions around an object to be examined and detects radiation that is transmitted through the object from the multiple directions; a table on which the object lies and which can move the object in a body axis direction of the object; a reconstruction parameter setting device that sets reconstruction parameters that include the amount of movement of the table in the body axis direction, and that are used to reconstruct an image of the object; a reconstruction view area calculating device that calculates a reconstruction view area for at least one data segment that is necessary for reconstruction calculation that is determined for each spatial position that is reconstructed based on the reconstruction parameters that are set; a reference segment position setting device that sets a reference segment position in the calculated reconstruction view area according to a phase signal that is obtained by dynamic analysis of the object; an effective segment calculating device that calculates a data segment that includes the set reference segment position as an effective segment using a predetermined weight function; and an image creating device that creates an image by reconstructing the calculated effective segments.

It is thus possible to provide a radiotomography apparatus that is capable of achieving both an improvement in temporal resolution and a reduction in ineffective radiation exposure.

The effective segment calculating device may further comprise number of effective segments calculating device that calculates a number of effective segments for which the set reference segment position is present in the reconstruction view area; and a segment width calculating device that calculates a width of an effective segment that is defined at the reference segment position for each of the calculated number of effective segments, using an area which an adjacent data segment thereof has.

The predetermined weight function that is used for the effective segment calculating device is a weight function which highly contributes to image reconstruction of data segments for which the phase signals are equal by the widths of the calculated effective segments and the set reference segment positions, and for which the sum of weights of data segments that face the effective segments are equal.

Furthermore, a preferred embodiment of the present invention comprises a radiation source including a radiation generating unit that irradiates radiation and a control unit that controls the radiation generating unit; a radiation detection device that is disposed facing the radiation generating unit to sandwich an object to be examined therebetween, and that detects radiation transmitted though the object to output radiation transmission data; a rotating device that is equipped with the radiation source and the radiation detection device and is capable of rotation; a first image creating device that performs reconstruction calculation processing based on the radiation transmission data; a periodic motion data input device that measures periodic motion of the object and accepts input of periodic motion data that is obtained; a reconstruction reference position calculating device that calculates a reconstruction reference position that indicates an arbitrary periodic phase position at which reconstruction is performed, based on the periodic motion data; a significance calculating device that calculates a significance for each reconstruction reference position that is calculated by the reconstruction reference position calculating device, based on a feature quantity that shows a periodic motion of the object or a time at which the radiation generating apparatus passes the reconstruction reference position; an extraction range calculating device that calculates an extraction range in accordance with a significance that is calculated for each of the reconstruction reference positions such that as the significance of a reconstruction reference position increases, the extraction range of the radiation transmission data widens for that reconstruction reference position; and a second image creating device that performs reconstruction calculation processing based on the radiation transmission data that is included in the extraction range that is calculated.

Thus, since a reference segment is provided at the finishing edge of each segment to facilitate exclusion of phases with a large bodily motion such as a heartbeat, and it is therefore possible to deal with individual differences among different objects, it is possible to provide a radiotomography apparatus capable of inhibiting the effect of motion artifacts with respect to images.

Further, a preferred embodiment of the present invention comprises a radiation detection device that detects radiation that is transmitted through an object to be examined from around the object at a predetermined scanning speed; a table on which the object lies; a scanning speed control device that can set the predetermined scanning speed of the radiation detection device; an image creating device that processes the detected radiation to convert resulting data into data segments to create a tomogram; a heartbeat fluctuation measuring device that measures a heart rate and a heartbeat fluctuation amount of the object; a reference heartbeat fluctuation calculating device that determines a reference heart rate and a reference heartbeat fluctuation amount based on a heart rate and a heartbeat fluctuation amount that are measured by the heartbeat fluctuation measuring device; and a scanning speed selecting device that selects a scanning speed based on the reference heart rate and the reference heartbeat fluctuation amount that are output from the reference heartbeat fluctuation calculating device, and outputs the scanning speed to the scanning speed control device as the predetermined scanning speed.

It is thereby possible to provide a radiotomography apparatus that, even when dynamic information of an object to be examined such as the object's heartbeat differs between the time of setting the image speed and the time of actual scanning, is capable of employing the appropriate temporal resolution by using the fluctuation tendency of the heart rate and the like.

Furthermore, a preferred embodiment of the present invention comprises a radiation source including a radiation generating unit that irradiates radiation and a control unit that controls the radiation generating unit; a radiation detection device that is disposed facing the radiation generating unit to sandwich an object to be examined therebetween, and that detects radiation transmitted through the object to output radiation transmission data; a rotating device that is equipped with the radiation source and the radiation detection device and is capable of rotation; a first image creating device that performs reconstruction calculation processing based on the radiation transmission data; a periodic motion data input device that measures periodic motion of the object and accepts input of periodic motion data that is obtained; a reconstruction reference position calculating device that calculates a reconstruction reference position that indicates an arbitrary periodic phase position at which reconstruction is performed, based on the periodic motion data; a significance calculating device that calculates a significance for each reconstruction reference position that is calculated by the reconstruction reference position calculating device, based on a feature quantity that shows a periodic motion of the object or a time at which the radiation generating apparatus passes the reconstruction reference position; an extraction range calculating device that calculates an extraction range in accordance with a significance that is calculated for each of the reconstruction reference positions such that as the significance of a reconstruction reference position increases, the extraction range of the radiation transmission data widens for that reconstruction reference position; and a second image creating device that performs reconstruction calculation processing based on the radiation transmission data that is included in the extraction range that is calculated.

It is therefore possible to provide a radiotomography apparatus that can contribute to enhancing a spatial resolution or a temporal resolution when collecting divided image data of the same phase for a dynamic state such as a plurality of heartbeats.

According to the present invention, it is possible to achieve both improved temporal resolution and reduced ineffective radiation exposure.

BRIEF DESCRIPTION OF THE DRAWINGS

FIGS. 6(a), (b), (c) and (d) are schematic diagrams illustrating weight adjustment and relocation of segments within a reconstruction view area at the time of full reconstruction according to the first embodiment herein;

FIGS. 7(a), (b), and (c) are schematic diagrams illustrating a method of creating a weight function according to the first embodiment;

FIG. 8 consists of views illustrating a weighting function according to the first embodiment, in which (a) is a schematic diagram illustrating a case of an overlap ratio of 100%, (b) is a schematic diagram illustrating a case of an overlap ratio of 50%, and (c) is a schematic diagram illustrating a case of an overlap ratio of 0%;

FIGS. 13(a), (b) (c) and (d) are views illustrating weight adjustment and relocation of segments within a reconstruction view area at the time of half reconstruction according to the first embodiment;

FIG. 14 consists of schematic diagrams that illustrate segment weighting according to the conventional technology that precedes the fourth embodiment, in which (a) illustrates R wave signals and (b) illustrates segment reference positions;

FIG. 19 is a schematic diagram illustrating the thickness of an X ray that is focused by a collimator;

FIG. 22 consists of schematic diagrams that illustrate a method of calculating reference segment positions according to a relative method, in which (a) illustrates R wave signals and (b) illustrates reference segment positions;

FIG. 25(a) is a three-dimensional reconstruction explanatory drawing (X-Y plane), and (b) is a three-dimensional reconstruction explanatory drawing (X-Z plane);

FIG. 27(a) is a schematic diagram for explaining a starting edge reference method, which shows weight functions and reference segment positions after relocation, and (b) is a schematic diagram for explaining a starting edge reference method, which shows a state in which calculated weight functions are disposed at pre-relocation view positions;

FIG. 28(a) is a schematic diagram for explaining a finishing edge reference method, which shows weight functions and reference segment positions after relocation, and (b) is a schematic diagram for explaining a finishing edge reference method, which shows a state in which calculated weight functions are disposed at pre-relocation view positions;

FIG. 29(a) is a schematic diagram for explaining a center-starting edge reference method, which shows weight functions and reference segment positions after relocation, and (b) is a schematic diagram for explaining a center-starting edge reference method, which shows a state in which calculated weight functions are disposed at pre-relocation view positions;

FIG. 30(a) is a schematic diagram for explaining a center-finishing edge reference method, which shows weight functions and reference segment positions after relocation, and (b) is a schematic diagram for explaining a center-finishing edge reference method, which shows a state in which calculated weight functions are disposed at pre-relocation view positions;

FIG. 32(a) is a schematic diagram for explaining correspondence processing in a case where relocated phases were at the same reference position, showing a state in which, among the reference segment positions after relocation, a reference segment position that is far from the center of a reconstruction view area is deleted; (b) is a schematic diagram for explaining correspondence processing in a case where relocated phases were at the same reference position, showing a state in which a reference segment position that is far from the center of a reconstruction view area was deleted to generate a weight function; and (c) is a schematic diagram for explaining correspondence processing in a case where relocated phases were at the same reference position, showing a state in which reference segment positions and weight functions are disposed at pre-relocation view positions;

FIG. 33 is a block diagram showing the configuration of an X-ray CT apparatus according to the fifth embodiment;

FIG. 36(a) is a graph describing one correlation between a heartbeat fluctuation width and effective temporal resolution with respect to another two scanning speeds, that shows a view at the time of a 0.5 second scan (comparatively high temporal resolution), and (b) is a graph describing one correlation between a heartbeat fluctuation width and effective temporal resolution with respect to the two scanning speeds, that shows a view at the time of a 1.1 second scan (comparatively low temporal resolution);

DESCRIPTION OF SYMBOLS

1: X-ray tube, 2: collimator, 3: X-ray detector, 4: preamplifier, 5: bed, 6: rotational driving apparatus, 7: central control unit, 8: image processor, 9: display, 10: input device, 11: collimator controller, 12: X-ray controller, 13: high voltage generator, 20: scanner control device, 30: heartbeat fluctuation measuring device, 51-56: R wave, 61-69: segment position, 70: reconstruction view area, 80: weight function, 81: data segment creating device, 82: reconstruction view area calculating device, 83: reference segment position calculating device, 84: effective segment determining device, 85: relocation weighting device, 86: image creating device, 401:

X-ray CT apparatus, 402: object to be examined, 410: scanner, 411: X-ray generator, 4111: high voltage switching unit, 4112: high voltage generator, 4113: X-ray controller, 412: X-ray detector, 4121: preamplifier, 413: collimator, 4131: collimator controller, 414: driving apparatus, 415: scanner control apparatus, 416: central control unit, 420: bed, 421: table control apparatus, 422: table movement measuring device, 430: operation unit, 431: arithmetic unit, 4311: reconstruction calculating device, 4312: image processor, 4313: storage device, 432: input/output device, 4321: display, 4322: input device, 433: power/signal wire, 440: electrocardiograph, 501: X-ray tube, 502: collimator, 503: X-ray detector, 504: preamplifier, 505: bed, 506: rotational driving apparatus, 507: central control unit, 508: image processor, 509: display, 510: input device, 511: collimator controller, 512: X-ray controller, 513: high voltage generator, 514: high voltage switching unit, 516: table control apparatus, 517: table movement measuring device, 520: scanning speed control device, 530: heartbeat fluctuation measuring device, 540: reference heartbeat fluctuation calculating device, 550: scanning speed selecting device, 801: X-ray CT apparatus, 810: scanner gantry part, 811: X-ray tube, 812: X-ray detector, 813: rotary table, 814: collimator, 815: rotational driving apparatus, 820: image processor, 821: mouse, 822: computer, 823: display, 830: measurement controller, 840: electrocardiograph, 850: patient table, 860: object

BEST MODE FOR CARRYING OUT THE INVENTION

Hereunder, preferred embodiments of the present invention will be described with reference to the attached drawings.

FIRST EMBODIMENT

Figure 1:
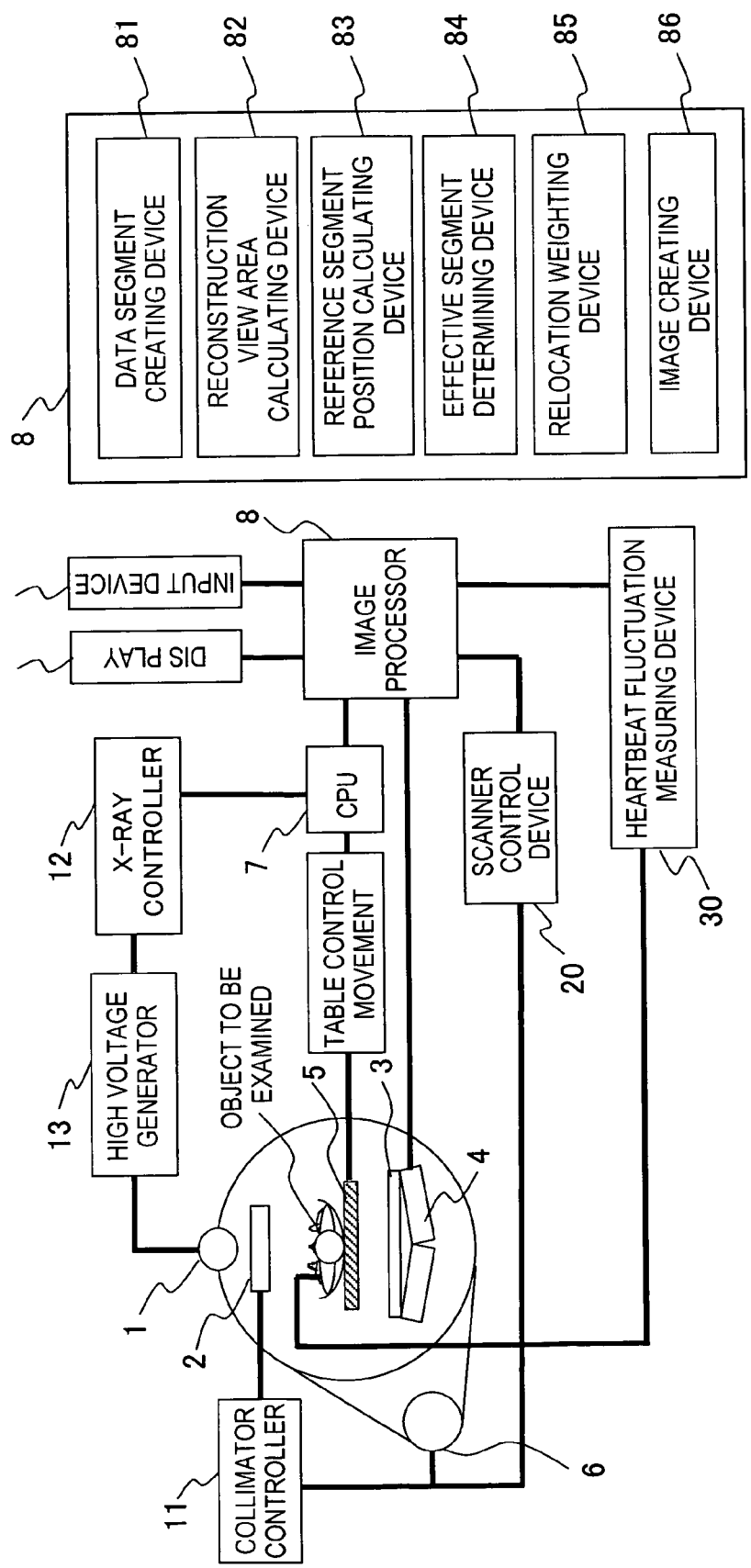
FIG. 1(a) is a block diagram showing the configuration of an X-ray CT apparatus according to the present invention, and (b) is an enlarged view of principal parts of the configuration of the X-ray CT apparatus.

FIG. 1 is an overall configuration view that illustrates a multislice X-ray CT apparatus using a cone beam X-ray that is one example of an X-ray CT apparatus according to this invention. The X-ray CT apparatus shown in FIG. 1 employs the so-called rotate-rotate (third generation) scanning method.

The X-ray CT apparatus shown in FIG. 1 comprises an X-ray tube 1, a collimator 2, an X-ray detector 3 as X-ray detecting device, a preamplifier 4, a table 5, a rotational driving apparatus 6 that implements a predetermined scanning speed, a central control unit (CPU) 7, an image processor 8, a display 9, an input device 10, a collimator controller 11, an X-ray controller 12, a high voltage generator 13, a scanner control device 20 and a heartbeat fluctuation measuring device 30. However, the heartbeat fluctuation measuring device 30 need not necessarily be included in the configuration of the X-ray CT apparatus according to this invention, and it is sufficient that it can be connected separately from outside.

The X-ray CT apparatus operates by the following procedures at the time of scanning. The high voltage generator 13 generates electric power as instructed from the input device 10 via the X-ray controller 12. The generated electric power is supplied to the X-ray tube 1 at a predetermined tube voltage and tube current. Upon receiving the tube voltage and tube current, the X-ray tube 1 emits an electron beam and the like to generate X-rays by striking the electron beam against a target. X-rays generated by the X-ray tube 1 are focused in accordance with a scanning site of the object by the collimator 2, and then irradiated at the object on the table 5. X rays that passed through the object are collected as transmitted X-ray data by the X-ray detector 3. The transmitted X-ray data that was collected is sent to the image processor 8 to reconstruct a tomogram of the object, and the reconstructed tomogram is displayed with the display 9. In this connection, normally, at the time of scanning a gantry that is equipped with the X-ray tube 1 and the X-ray detector 3 rotates around the object. The rotational driving apparatus 6 is responsible for this rotational driving, and it enables a circular scan or a helical scan by controlling movement of the table 5 via a CPU 7 simultaneously with rotation.

The characteristic parts of the present invention in the configuration shown in FIG. 1 are the input device 10 and the image processor 8. The image processor 8 includes a data segment creating device 81, a reconstruction view area calculating device 82, a reference segment position calculating device 83, an effective segment determining device 84, a relocation weighting device 85 and an image creating device 86. These components are described later.

Next, an outline of operations for ECG-gated reconstruction using the X-ray CT apparatus shown in FIG. 1 will be described referring to FIG. 2.

After ECG-gated scanning, in step S201 reconstruction parameters that were input from the input device 10 are sent to the image processor 8. The data segment creating device 81 of the image processor 8 extracts data segments (hereunder, "data segment" is abbreviated to "segment") from the transmitted X-ray data that was obtained by the ECG-gated scanning.

In step S202, the reconstruction view area calculating device 82 of the image processor 8 calculates a reconstruction view area in accordance with pixel positions or a reconstruction view area in accordance with a FOV (field of view) in the reconstruction parameters. The reconstruction view area is an area that is a natural number multiple of T. The scanning data of a predetermined cardiac phase that underwent ECG-gated scanning constitute the segments.

In step S203, the reference segment position calculating device 83 inside the image processor 8 calculates all of the segment positions. The subsequent processing is performed based on this positional information.

In step S204, the effective segment determining device 84 in the image processor 8 overlays the segment positions determined in step S203 on the reconstruction view area determined in step S202 to acquire only segment positions for which a reference segment position is within the reconstruction view area as effective segment positions.

In step S205, a relocation weighting device 85 in the image processor 8 performs adjustment so that the above described effective segment positions are contained in an at least 180° area.

In step S206, the relocation weighting device 85 performs adjustment so that a weight function that centers on the reference segment positions is contained in an at least 180° area. The relocation weighting device 85 relocates the reference segment position in a corresponding phase in the reconstruction view area. Next, weighting is performed so that the temporal resolution of the finally reconstructed image that is optimized. This weighting is carried out in order to align the data in each phase within the reconstruction view area, and weighting is carried out to complement the relocated data segments. More specifically, the relocation weighting device 85 relocates the reference segment position in a 180° area and also assigns weights to the relocated reference segment positions. According to this embodiment, although the relocation weighting device 85 is described as device that performs both relocation and weighting, it may be separated into relocating device and weighting device.

Finally, in step S207, the image creating device 86 within the image processor 8 allocates the weight function created in step S206 for each segment, and performs weighted three-dimensional reconstruction.

Figure 2:
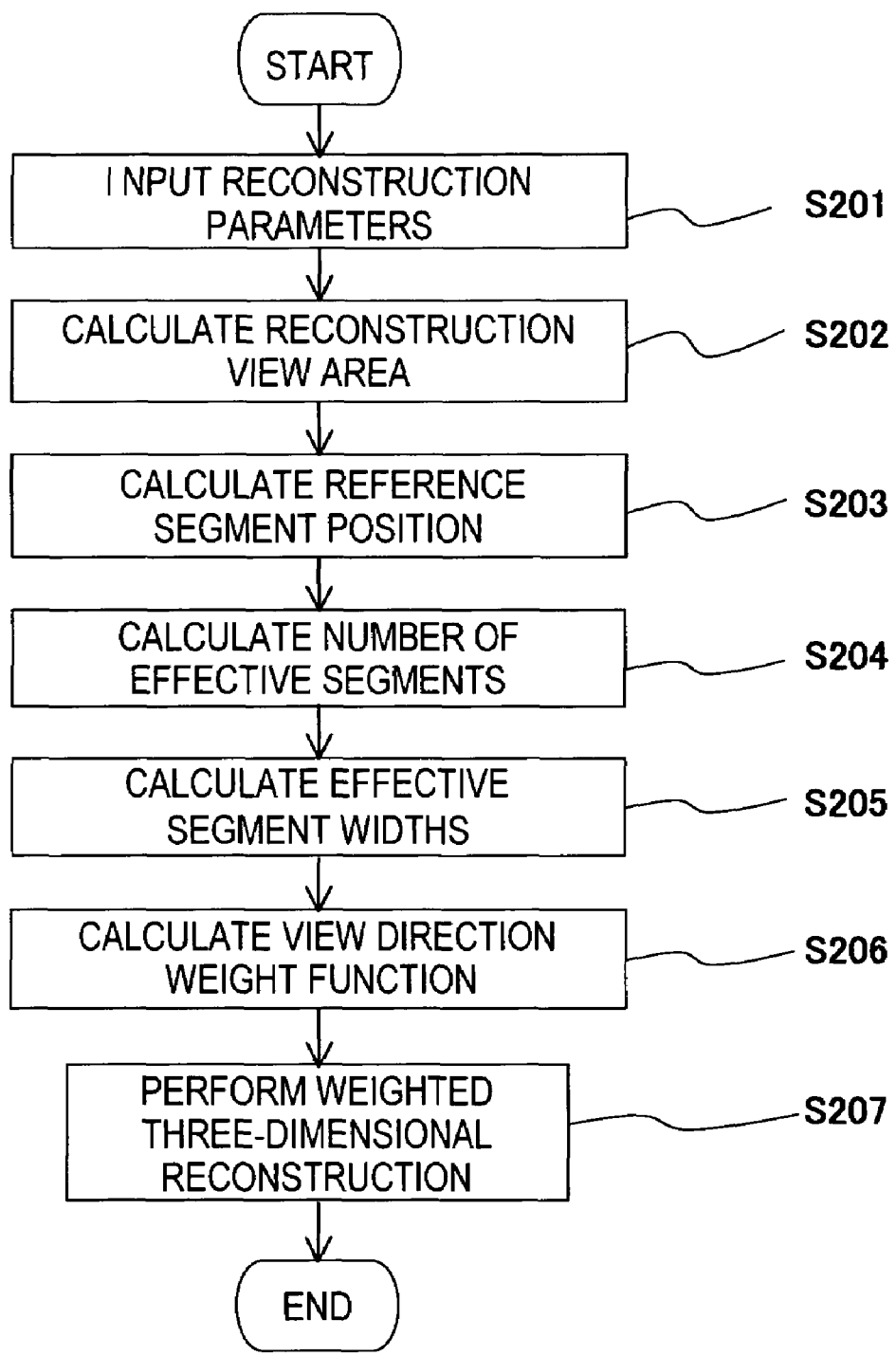
FIG. 2 is a flowchart that illustrates the operation of an X-ray CT apparatus according to the present invention.

Hereunder, the steps of the flowchart shown in FIG. 2 are described in detail. In this connection, the following description is made on the assumption that scanning was completed. Hereunder, the term "segment" refers to consecutive data that is consecutive in a view direction that includes X-ray transmission data in a certain cardiac phase, and the length thereof (hereunder, referred to as "segment width") depends on the scanning speed, heart rate, table feeding speed and the like. Further, the term "segment position" refers to a representative position in a view direction of a segment used to reconstruct a certain tomogram in a certain cardiac phase, and in most cases it is located at approximately the center of the segment width.

(Step S201) Input of Reconstruction Parameters

A user inputs reconstruction parameters using the input device 10.

For example, a mouse, keyboard, touch panel display and audio input device such as a microphone can be employed as the input device 10. The reconstruction parameters include, for example, FOV, region of interest (ROI), reconstruction image size, table feeding speed, cardiac phase to be reconstructed, a reconstruction mode such as half reconstruction or segment reconstruction, segment width index, reconstruction slice spacing, and reconstruction filter function, and all of the parameters need not necessarily be input.

(Step S202) Reconstruction View Area Calculation

The term "reconstruction view area" refers to the total extended distance of one or a plurality of data segments that can be used for reconstruction that is decided for each spatial position to be reconstructed. Although in the prior art the number of segments to be used for reconstruction is uniformly determined for the entire tomogram, according to this embodiment the number of segments is determined in correspondence with the FOV as described below.

As described in the foregoing, a reconstruction view area of segments created with the data segment creating device 81 shown in FIG. 1(b) is calculated by the reconstruction view area calculating device 82.

Figure 3B:
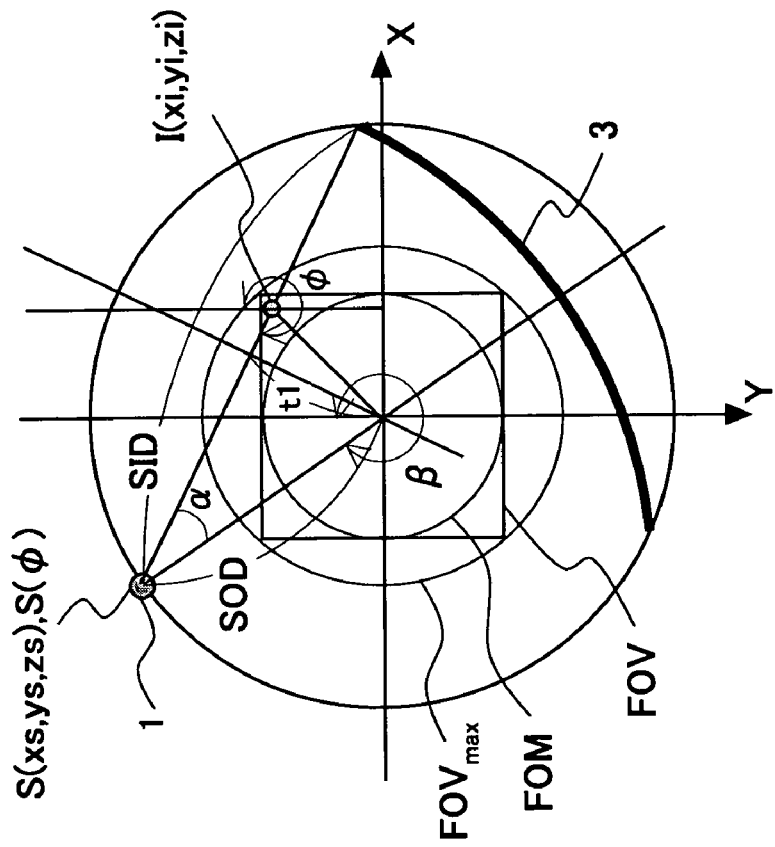
FIG. 3(a) is an explanatory view from one direction regarding calculation of a reconstruction view area, and (b) is an explanatory view from another direction regarding calculation of a reconstruction view area.
Figure 3A:
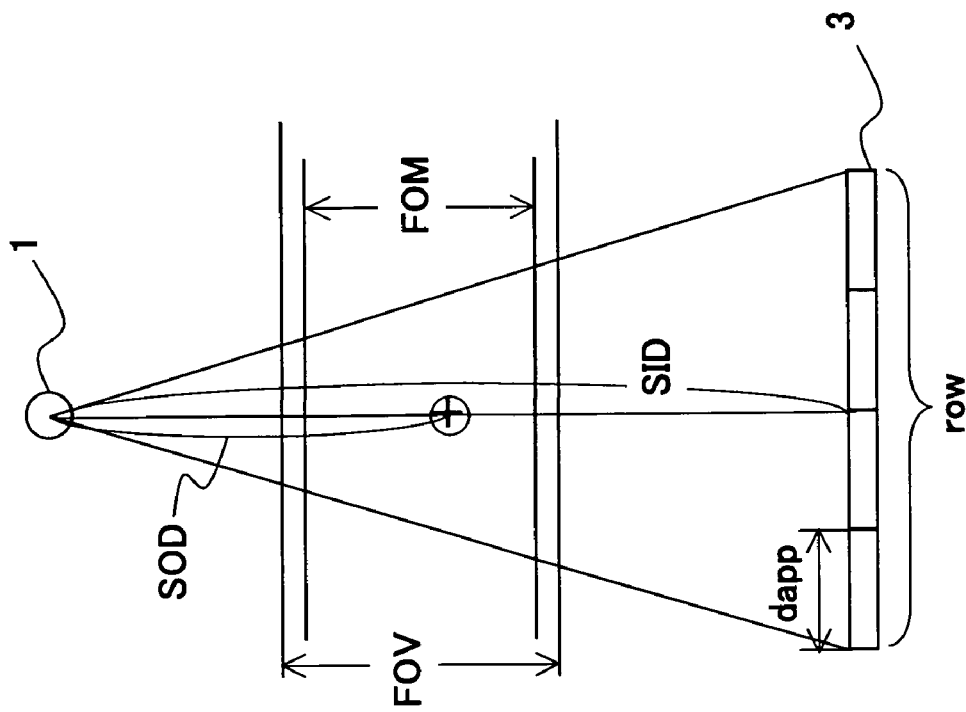

Calculation of a reconstruction view area in accordance with a FOV is described using FIG. 3. FIGS. 3(a) and (b) are respective sectional views of a rotating part including the X-ray tube 1 and the detector 3, that show the positional relationship of principle parts on the Y-Z axial plane and the X-Y axial plane. When it is assumed that dapp represents detector element size (body axis Z direction), row represents number of detector rows, SOD represents distance between X-ray source and center of rotation, SID represents distance between X-ray source and detector, T represents table feeding speed, FOV represents effective field of view, FOM represents effective operation field of view, and FOV max represents maximum value for effective field of view, FOM is obtained by Formula 1 below. In this example, "FOVX" and "FOVY" are components of the X axis and Y axis of FOV in FIG. 3(b), respectively.

[Formula 1]

$$FOM = \sqrt{\left(\frac{FOVX}{2}\right)^2 + \left(\frac{FOVY}{2}\right)^2} \quad (1)$$

Provided that, when FOM>FOV max, then FOM=FOV max.

Thus, a reconstruction view area R [rad] is, for example, obtained by Formula 2 below.

[Formula 2]

$$R = dapp * (\text{row} - 1) * \frac{SOD - \frac{FOM}{2}}{SID} * \frac{2\pi}{T} - 2 * \arcsin\left(\frac{FOM}{2 * SOD}\right) \quad (2)$$

The above described method of calculating a reconstruction view area is only one example thereof, and the method is not limited thereto. Further, since the reconstruction view area is changed by the operational precision in the body axis direction of the reconstruction algorithm, it is not limited to a single value.

(Step S203) Calculation of Reference Segment Position

In step S203, segment positions are determined on the basis of a contraction commencement signal, for example, an electrocardiographic R wave, that is acquired by dynamic analysis of scanning data obtained with an electrocardiograph or other X-ray CT apparatus and the maximum value of the reconstruction view area obtained in the above described step S202. As described above, the reference segment position calculating device 83 shown in FIG. 1(b) determines the segment positions.

Hereunder, a contraction commencement signal will be described as a cardiac R-wave. A segment position corresponding to the cardiac phase it is desired to reconstruct is calculated on the basis of an R wave.

Figure 4A:
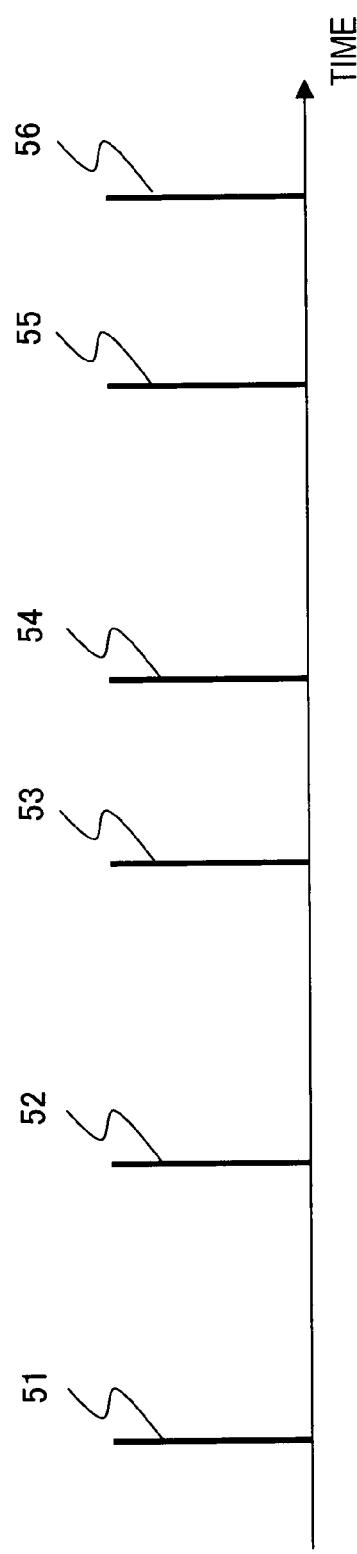
FIG. 4 consists of schematic diagrams that illustrate one example of the relation between R wave signals and segment positions in the X-ray CT apparatus according to the present invention, in which (a) illustrates R wave signals and (b) illustrates segment positions.
Figure 4B:
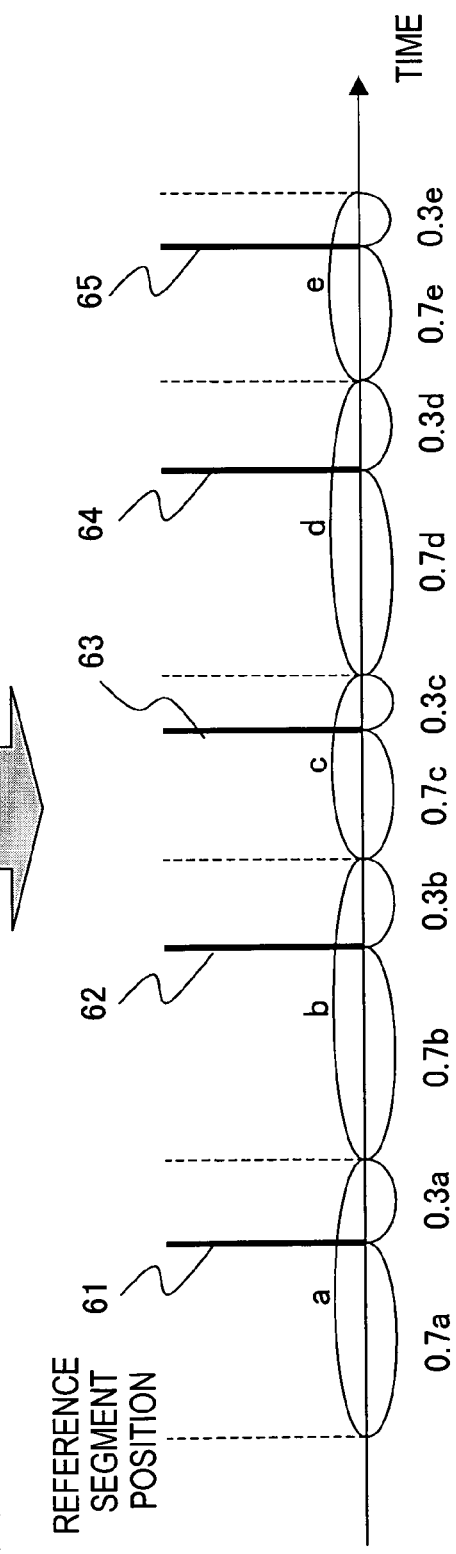

For example, as shown in FIG. 4(a) and FIG. 4(b), when an operator wants to set cardiac phases to be reconstructed as the 70% positions in the intervals between R wave signals from 51 to 56, respectively, the value 70% is previously input from the input device 10 in FIG. 1(a). The reference segment position calculating device 83 then determines the 70% position of each phase interval between adjoining R waves from 51 to 56 as reference segment positions 61 to 65. In this case, in FIG. 4(a), the intervals between the R waves 51, 52 and 53, and between 54 and 55 are approximately equal. Further, although the intervals between the R wave 53 and R wave 54 and the R wave 55 and R wave 56 are somewhat narrow, even in this case the respective 70% positions of the adjoining R wave intervals are employed as reference segment positions.

(Step S204) Calculation of Number of Segments

Figure 5:
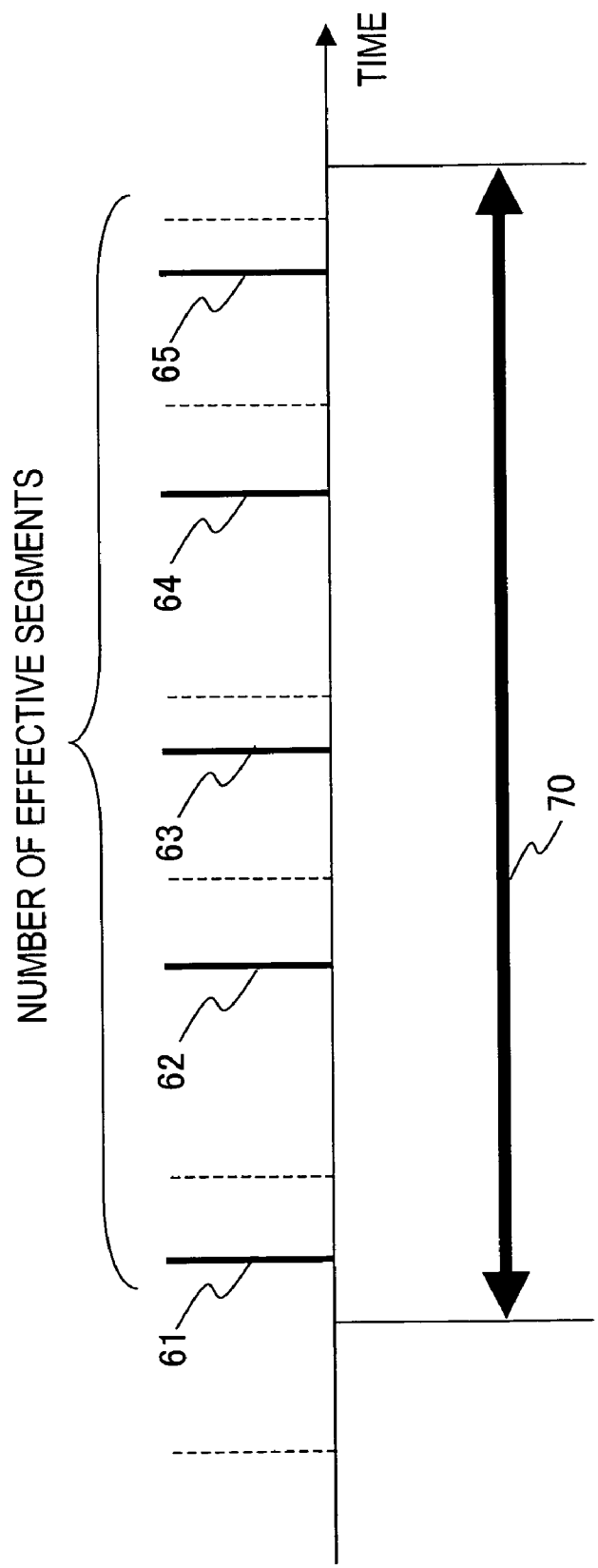
FIG. 5 is a schematic diagram that illustrates one example of the relation between a reconstruction view area and the number of effective segments for the X-ray CT apparatus according to the present invention.

In step S204, the number of effective segments is calculated in accordance with the FOV or each voxel position based on the maximum view width and the above described contraction commencement signal. As described in the foregoing, the effective segment determining device 84 shown in FIG. 11(b) applies the reference segment position to a reconstruction view area 70 that was determined in step S202, as shown in FIG. 5. The effective segment determining device 84 then acquires signals 61, 62, 63, 64 and 65 that indicate the reference segment positions included in the reconstruction view area 70, as effective segment positions.

In this case, according to the prior art, image reconstruction had been performed using the same number of segment positions across the entire tomogram, for example, FOV max shown in FIG. 3(a), and not by individually calculating the number of effective segment positions in accordance with the FOV or each voxel position.

The present embodiment is characterized by the fact that, if there is a segment position with high redundancy that can be utilized inside the FOV, the temporal resolution is enhanced as much as possible by utilizing that data as an effective segment position in reconstruction without allowing it to be omitted.

(Step S205) Segment Width Calculation

As described above, in step S205 the relocation weighting device 85 in FIG. 1(b) locates the reference segment positions in a repeating manner inside a $2\pi$ (360°) range, and refers to intervals between adjoining reference segment positions to adjust the segment width. In this connection, the repetition range is not limited to $2\pi$ (360°), and may be $N\pi$ (where, N is a natural number of 1 or more). Hereunder, segment width calculation is described taking FIG. 6 as one example.

It is assumed that X-ray transmission data as shown in FIG. 6(a) was obtained. The reference segment positions (effective segment positions) 65 to 69 shown in FIG. 6(a) correspond to, for example, reference segment positions 61 to 65 that were recognized as effective segments in FIG. 5. In this case, L0 and L1 are referred to as starting edge segment allowable maximum width and finishing edge segment allowable maximum width, respectively. The starting edge segment allowable maximum width L0 is the distance between the starting edge of the reconstruction view area 70 and the reference segment position 65 neighboring that starting edge. The finishing edge segment allowable maximum width L1 is the distance between the finishing edge of the reconstruction view area 70 and the reference segment position 69 neighboring that finishing edge. In this connection, this distance becomes the critical value (limiting condition) with respect to the shape and width of a weight for reference segment positions described later referring to FIG. 6(d) and FIG. 7(a).

Next, as shown in FIG. 6(b), reference segment positions (effective segment positions) inside the reconstruction view area 70 are repeated for each $2\pi$ (360°) and disposed in a certain $2\pi$ (360°) reconstruction area. When moving the reference segment positions, movement is performed while matching the positions with a view phase (or circular phase). Hereunder, moving reference segment positions while matching the positions with a view phase (or circular phase) to arrange X-ray transmission data of $N\pi$ (where N is a natural number of 1 or more) is referred to as "relocation". At the time of this relocation, when there are reference segment positions of almost the same view phase (or circular phase), it is best to select the reference segment position that is closer to the center of the reconstruction view area 70. The reason is that the reference segment position that is closer to the center of the reconstruction view area 70 is less liable to produce artifacts since it is possible to use X rays in a state in which the cone angle that is the circulation axis of the cone beam, i.e. the spread in the Z-axis direction, is small. Alternatively, with respect to both of the above described approximately identical cardiac phase segments, synthesis may be performed by assigning weights such that the sum thereof is one. This is because artifacts can be alleviated by assigning weights.

Next, as shown in FIG. 6(c), the relocation weighting device 85 determines the reference segment widths w1, w2, w3 and w4 of the segments including the reference segment positions (effective segment positions) 65 to 69 as ½ of the interval between the adjoining reference segment positions.

As will be understood from the figure, the reference segment position included in each segment is not necessarily located at the center of the segment width.

Next, as shown in FIG. 6(d), the relocation weighting device 85 adjusts the segment widths so that segments located at the edges of the reconstruction view area 70 are contained in the reconstruction view area 70. At this time, adjustment is carried out so that the aforementioned starting edge segment allowable maximum width L0 and the finishing edge segment allowable maximum width L1 do not exceed the reconstruction view area 70. As shown in FIG. 6(a), the starting edge segment allowable maximum width L0 corresponds to the distance from the reference segment position 65 to the starting edge of the reconstruction view area 70.

When the weight of the reference segment position 65 extends past L0, it overruns the reconstruction view area 70. If the reference segment position 65 exceeds the reconstruction view area 70, data that is different from the slice thickness that it is attempted to reproduce becomes mixed in with the desired data, and the spatial resolution decreases and affects the image quality. However, when it is desired to sacrifice spatial resolution to increase the temporal resolution or when deterioration of the spatial resolution is not a problem, a state in which the weight of the reference segment position 65 extends past L0 need not necessarily be avoided.

Likewise, as shown in FIG. 6(a), the finishing edge segment allowable maximum width L1 corresponds to the distance from the reference segment position 69 to the finishing edge of the reconstruction view area 70. When the weight of the reference segment position 69 extends past L1, it overruns the reconstruction view area 70. If the reference segment position 69 overruns the reconstruction view area 70, data that is different from the slice thickness that it is attempted to reproduce becomes mixed in with the desired data, and the spatial resolution decreases and the image quality deteriorates. However, similarly to the above described starting edge segment allowable maximum width L0, when it is desired to sacrifice spatial resolution to increase the temporal resolution or when deterioration of the spatial resolution is not a problem, a state in which the weight of the reference segment position 69 extends past L1 need not necessarily be avoided.

In FIG. 6(c), the segment width w1 is pushed leftward from the above described relocated $2\pi$ area, and the segment width w2 is pushed rightward from the above described relocated $2\pi$ area. In this case, adjustment is performed so that these match in an area that does not overrun from the starting edge segment allowable maximum width L0 when circular data is obtained that connects the segments w1 and w2 by narrowing the width of the reference segment width w1, and the width of the reference segment width w2 is widened by the amount that the reference segment width w1 was narrowed. As the result of this adjustment, the segment widths are completely contained in the $2\pi$ area as shown in FIG. 6(d).

(Step S206) Creation of View Direction Weight Function

As described above, in step 6 following on from step S205, as shown in FIG. 1(b), based on the segment widths and segment positions determined in the above described step 5, the relocation weighting device 85 generates weights so that the contribution to image reconstruction of segments for which the cardiac phase is equivalent increases and the sum of weights between opposing phase data is equal. At this time, as shown in FIG. 7(a), the weight for each segment is determined so that the ends thereof are overlaid in the order w14, w43, w35, w52, w21, respectively. FIG. 7 illustrates that determination method.

FIG. 7(a) is a view showing a state in which weight functions are overlaid on the diagram shown in FIG. 6(d). First, the relocation weighting device 85 drops the starting edge segment allowable maximum width L0 and the finishing edge segment allowable maximum width L1 described in FIG. 6(*a*), within the diagram shown in FIG. 7(*a*). At this time, the relocation weighting device 85 causes the left edge of L0 and the starting edge of the reconstruction view area 70 to coincide. Similarly, the relocation weighting device 85 causes the right edge of L1 and the finishing edge of the reconstruction view area 70 to coincide. Next, the relocation weighting device 85 adjusts the overlapping widths of weights w21, w14, w35, w43 and w52 to determine final segment widths W1 to W5. As described previously, causing the left edge of L0 and the right edge of L1 to coincide with the starting edge and finishing edge of the reconstruction view area 70 is a necessary condition for enhancing the spatial resolution. In this connection, when it is desired to sacrifice spatial resolution to increase temporal resolution or when deterioration of the spatial resolution will not be a problem, a state in which the weight of the reference segment position extends past the starting edge segment allowable maximum width L0 or the finishing edge segment allowable maximum width L1 need not necessarily be avoided.

Next, the overlap ratio of the weight function will be described. FIG. 7(*a*) shows a state in which the overlap ratio of the weight function is approximately 40%. FIG. 8 describes another weight overlap ratio centered on the reference segment positions 65 and 68. FIG. 8(*a*) illustrates a state in which the overlap ratio of the weight function is 100%, FIG. 8(*b*) illustrates a state in which the weight overlap ratio is 50%, and FIG. 8(*c*) illustrates a state in which the weight overlap ratio is 0%. In the state in which the overlap ratio is 100% as shown in FIG. 8(*a*), the weight reaches as far as the reference segment positions 65 and 68, and the weights overlapping width w14 is the entire distance between the reference segment positions 65 and 68.

In the state shown in FIG. 8(*b*) in which the overlap ratio is 50%, the weight reaches as far as halfway between the reference segment positions 65 and 68, and the overlapping width w14 of the weight function is half of the distance between the reference segment positions 65 and 68. However, when the overlapping width w14 is half as described above, it can be moved from side to side within a range in which the positions of intersection do not exceed past the reference segment positions 65 and 68. In the state shown in FIG. 8(*c*) in which the overlap ratio is 0%, rectangular weights contact between the reference segment positions 65 and 68, and the weights overlapping width w14 is a center point between the reference segment positions 65 and 68 and does not have any distance. The differences in the weight shapes were described above, and although the discontinuity of data between segments can be reduced by widening the overlapping width of the weights and the data amount can be increased and noise reduced, on the other hand since the time width that contributes to the segment expands, the effective temporal resolution decreases to some degree. In particular, since noise irregularities are produced when the number of segments changes in accordance with a position, the overlapping width is preferably set to 100% as shown in FIG. 8(*a*). In this connection, an overlap ratio for a weight may be constant between segments or may change for each segment.

In this case, among the weights of the area of Nπ, additional weights may be assigned so that the contribution ratio of an area in which the temporal resolution for a narrow segment width is favorable becomes high. As a result, although noise increases, a portion with a favorable temporal resolution is principally used and the contribution ratio of data with poor temporal resolution can be lowered. Thereafter, as shown in FIG. 7(*b*), the above described relocated segments together with the above described created weights are returned to the pre-relocation area of 2π or more as shown in FIG. 6(*a*). Further, by totaling up each segment weight function along the time axis as shown in FIG. 7(*c*), a weight function 80 in the view direction that is ultimately used with weighted back projection.

(Step S207) Weighted Cone Beam Reconstruction

The image creating device 86 shown in FIG. 1(*b*) performs weighted three-dimensional reconstruction in the view direction, for example, reconstruction with an existing weighted cone beam back projection algorithm using the weight functions created in step S206. Hereunder, the reconstruction is described taking parallel beam—cone beam back projection as an example.

(1) Cone Angle Correction

According to this embodiment, cone angle correction is performed by software. More specifically, data on a reconstruction image is corrected in accordance with the distance from the circulation axis. By this correction, the influence of beam inclination with respect to the direction of the circulation axis can be reduced. In this case, the following three elements are used as a coordinate system: a parallel beam view angle φ, a parallel beam channel direction position t on a cylindrical detector centered on the X-ray source, and a vertical axis (direction of circulation axis) v perpendicular to a beam with respect to the parallel beam. Further, data before filter correction is represented by Ppara(φ, t, v), data after filter correction is represented by fPpara(φ, t, v), and the reconstruction filter function is represented by g(t). At this time, a reconstruction filtering process can be represented as shown in Formula 3 below, with reference to FIG. 3 and using a convolution method. In the formula, cone angle correction is performed by the portion SID/($\sqrt{SID^2+v^2}$). When a reconstruction filtering process is performed with respect to a plurality of detector rows, cone angle correction is preferably performed prior to the reconstruction filtering process, and if the reconstruction filtering process is performed for each row of a certain X-ray detector 3, it may be performed prior to the reconstruction filtering process of Formula 3 below or after the reconstruction filtering process. Hereunder, a case is described in which a reconstruction filtering process is performed for each row of a certain X-ray detector 3. As the cone angle correction, a cone angle correction that is used with a known three-dimensional back projection method, starting with the Feldkamp method, can be applied.

[Formula 3]

$$fP_{para}(\phi, t, v) = \int_{-\infty}^{\infty} \frac{SID}{\sqrt{SID^2 + v^2}} P_{para}(\phi, t - t', v) g(t') dt' \quad (3)$$

(2) Realignment Processing (Rebinning)

Figure 9A:
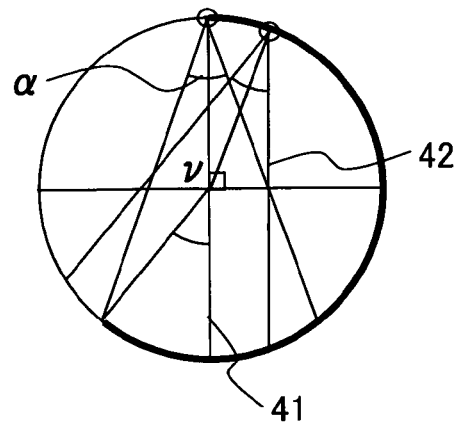
FIG. 9 consists of schematic diagrams that describe rearrangement (rebinning) between fan beams and parallel beams, in which (a) illustrates fan beams and (b) illustrates parallel beams.
Figure 9B:
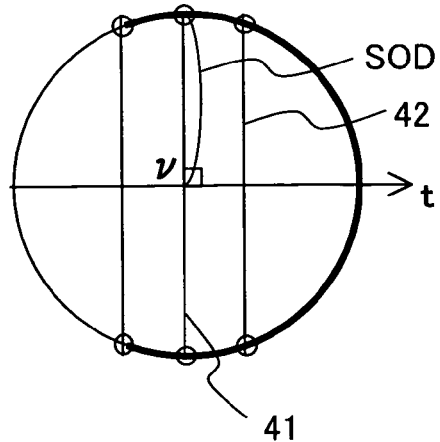

In order to speed-up calculation, all X-ray beams that are irradiated in a fan shape (hereunder, referred to as "fan beam") when viewed from the direction of the circulation axis as shown in FIG. 9(*a*) are rearranged into parallel X-ray beams (hereunder, referred to as "parallel beams") as shown in FIG. 9(*b*). The point to note in this instance is that the actual scanning is performed with fan beams. The term "parallel beam" refers to the result that data is rearranged so that it appears as if scanning was performed with parallel X-rays. For example, an X-ray beam 41 shown in FIG. 9(*a*) is common with an X-ray beam 41 shown in FIG. 9(*b*), and an X-ray beam 42 shown in FIG. 9(a) is common with an X-ray beam 42 shown in FIG. 9(b). A result in which X-ray beams that were collected from various view angles in this manner are rearranged in a parallel manner is, in this case, called parallel beams. In this connection, at the time of this rearrangement, properties that are common to an X-ray CT apparatus in which exchange of beams from diametrically opposed directions is possible can also be utilized. The above described realignment processing is also referred to as "rebinning". When fan beams are denoted as Pfan (β, α, ν) and shown as parallel beams, the realignment processing can be represented as in Formula 4 below. In the formula below, α is the fan beam opening angle in a circular direction (fan beam channel direction), β is the view angle of the fan beams, and ν is the axis (direction of circulation axis) perpendicular to the parallel beams.

[Formula 4]

$$P_{para}(\phi, t, \nu) = P_{fan}(\phi + \alpha, \alpha, \nu) \quad (4)$$

$$\text{wherein, } \alpha = \arcsin\frac{t}{SOD}$$

(3) Filter Correction (Reconstruction Filtering)

A reconstruction filter is applied to correct blurs in X-ray transmission data. A reconstruction filter can be implemented by, for example, a convolution operation. When the back projection processing as performed in step S207 is implemented without a filter, the obtained image is an image that is blurred in the same manner as if a filter having a $1/(\sqrt{(x^2+y^2)})$ point spread function with respect to F(X,y) was superimposed. Therefore, the role of the reconstruction filter is to rectify blurs in X-ray transmission data by executing a high-pass enhancement filter process prior to reconstruction.

Two types of methods exist for the reconstruction filtering: a convolution method that performs a convolution operation in real space (real space filtering), and a Fourier method (Fourier space filtering) that performs multiplication in Fourier space. Real space filtering is a convolution process of a filter function that was inverse Fourier transformed in real space. Fourier space filtering is a process that applies inverse Fourier transformation after transformation into Fourier space and multiplication of a filter function (spatial filter) using Fourier transformation. Although these are mathematically equivalent, the filter process in Fourier space for which computing time is fast is preferable.

Examples of a specific filter used in the reconstruction include a Shepp and Logan filter and a Ramachandran and Lakshminarayanan filter. Alternatively, a filter to be used may be selected based on clinical experience from among filters obtained by modifying these filter functions according to clinical experience.

When parallel X-ray transmission data is represented as Ppara (φ, t, ν), parallel X-ray transmission data after a filter process is represented as fPpara (φ, t, ν), and the reconstruction filter as G(ω), Fourier space filtering according to the Fourier method can be expressed by Formula 5 below.

[Formula 5]

$$fP_{para}(\phi, t, \nu) = \frac{1}{4\pi}\int_{-\infty}^{\infty}\int_{-\infty}^{\infty}P_{para}(\phi, t, \nu)\cdot\exp(-i\omega t)dt\cdot G(\omega)\cdot\exp(i\omega t)d\omega \quad (5)$$

In contrast, real space filtering according to a convolution method is as expressed in Formula 7 below, when the inverse Fourier transformation g(t) of G(ω) is obtained by Formula 6 below.

[Formula 6]

$$g(t) = \frac{1}{2\pi}\int_{-\infty}^{\infty}G(\omega)\cdot\exp(i\omega t)d\omega \quad (6)$$

[Formula 7]

$$fP_{para}(\phi, t, \nu) = \int_{-\infty}^{\infty}P_{para}(\phi, t-t', \nu)g'(t')dt' \quad (7)$$

In this case, although the application direction of the filter was taken as t direction for simplicity, the filter may be applied in a higher order direction that combines the t direction, ν direction and φ direction.

Further, the X-ray transmission data is originally discrete data and not continuous. Therefore, in order to calculate the X-ray transmission data as discrete data, for example, a known method that is similar to filter correction used with weighted helical correction reconstruction or the like can be used.

(Step S207) Weighted Three-Dimensional Back Projection

The image creating device 86 shown in FIG. 1(b) also executes step 7 following step 6. As shown in FIG. 3(b), when we assume a reconstruction vowel I (x1, y1, z1), a phase angle of parallel beams φ, a beam opening angle α, a distance between an X-ray source and center of rotation SOD, a relative moving distance of an X-ray source with respect to an object to be examined per single scanner rotation on a detector T, a ν axis direction position on a cylindrical detector centered on an X-ray source V, and a position in a channel direction as t1, Formula 8 below holds.

[Formula 8]

$$I(x_1, y_1, z_1) = \frac{1}{\pi}\int_{B_e(x_1,y_1,z_1)}^{B_s(x_1,y_1,z_1)}fP_{para}(\phi, t_1, \nu)\cdot W(\theta - B_s(x_1, y_1, z_1))d\phi \quad (8)$$

In a weighted three-dimensional back projection, a reconstruction image or X-ray transmission data that actually should be handled discretely is handled as continuous data. Therefore, to approximately calculate data that is insufficient for three-dimensional scanning, it is necessary to combine interpolation of the phase direction (time direction, φ direction), and the detector row direction (ν direction) and detector channel direction (t direction) using a known interpolation method such as Lagrange interpolation. In this connection, in order to shorten the computing time the interpolation directions (dimensions) can be decreased. Further, nearest-neighbor data that was resampled to a high intensity may be selected. A cardiac image in a desired cardiac phase can be reconstructed by the above described series of processing.

Further, although this embodiment was described for a case of a helical scan of a multislice X-ray CT apparatus using a cone beam X-ray, the present invention is not limited thereto, and the invention can also be applied to a circular scan.

Figure 10A:
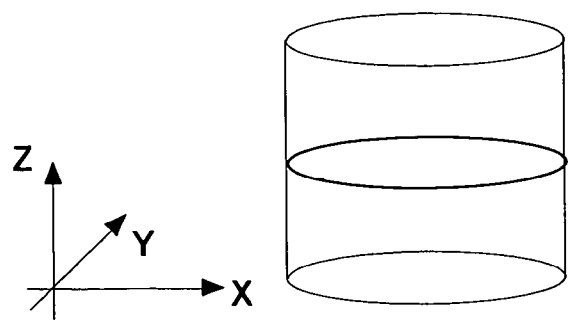
FIG. 10 consists of conceptual diagrams illustrating a circular scan and a helical scan of an X-ray CT apparatus, in which (a) illustrates a circular scan and (b) illustrates a helical scan.
Figure 10B:
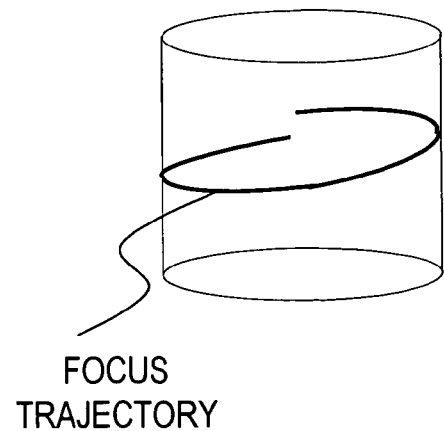

When a helical scan as shown in FIG. 10(b) was performed using a multi-row detector, for example, scanning control can be performed whereby after the first row of detectors collect X-ray transmission data from a certain view angle for a certain tomographic plane, the second row collect X-ray transmission data from a certain view angle for the same tomographic plane, and likewise the third to nth rows continue to collect data from a certain view angle for that tomographic plane in the same manner.

In general, when performing helical scanning with a multi-row detector, it is possible to perform scan control such that different detector rows on the detector respectively detect transmission X-rays of a certain predetermined tomographic plane from respective view angles. At this time, if the interpolation is used, by the circular scan shown in FIG. 9(a), an effect can be obtained that is ultimately the same as detecting transmission X rays from various view angles.

In the case of this embodiment, by performing a helical scan using the above described multi-row detector it is possible to acquire a plurality of cross sections of segments of a predetermined cardiac phase from many view directions at one time. However, even if circular scanning is performed using the above described multi-row detector, it is possible to apply the present invention in a similar manner as described above without any different with respect to the fact that it is possible to acquire a plurality of cross sections of segments of a predetermined cardiac phase from many view directions.

Although a tomographic apparatus that uses X rays is used according to this embodiment, the present embodiment is not limited thereto, and it can also be applied to a tomographic apparatus that uses gamma rays, neutron rays, positrons, electromagnetic energy or light. A scanner method is also not limited to the first generation, second generation, third generation or fourth generation method, and the invention can be used for an electron beam CT, a cathode scan CT or a multi-tube CT equipped with a plurality of X-ray sources. Further, regarding the detector shape, the invention is applicable to any kind of detector such as a detector disposed on a cylindrical surface that is centered on an X-ray source, a flat panel detector, a detector disposed on a spherical surface that is centered on an X-ray source, and a detector disposed on a cylindrical surface that is centered on the circulation axis.

Figure 11C:
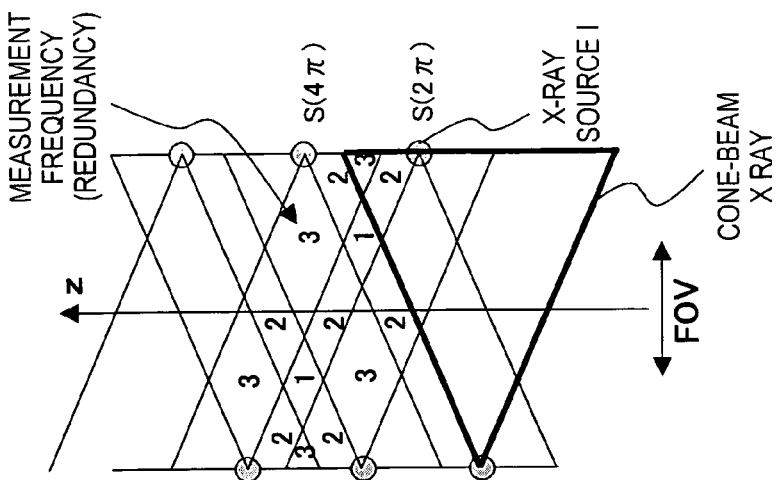
FIGS. 11(a), (b) and (c) are conceptual diagrams that illustrate a relation along a circulation axis that shows a detector collimation thickness on a circulation axis for an X-ray source and a multi-row X-ray detector in an X-ray CT apparatus as one example of the X-ray CT apparatus.
Figure 11B:
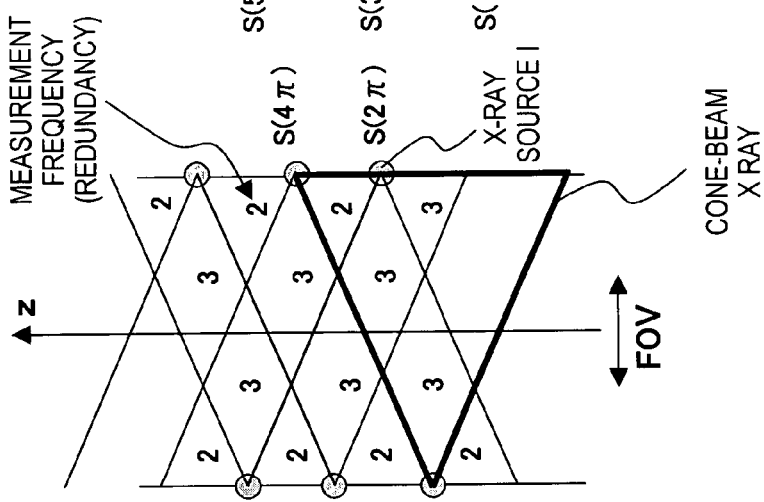
Figure 11A:
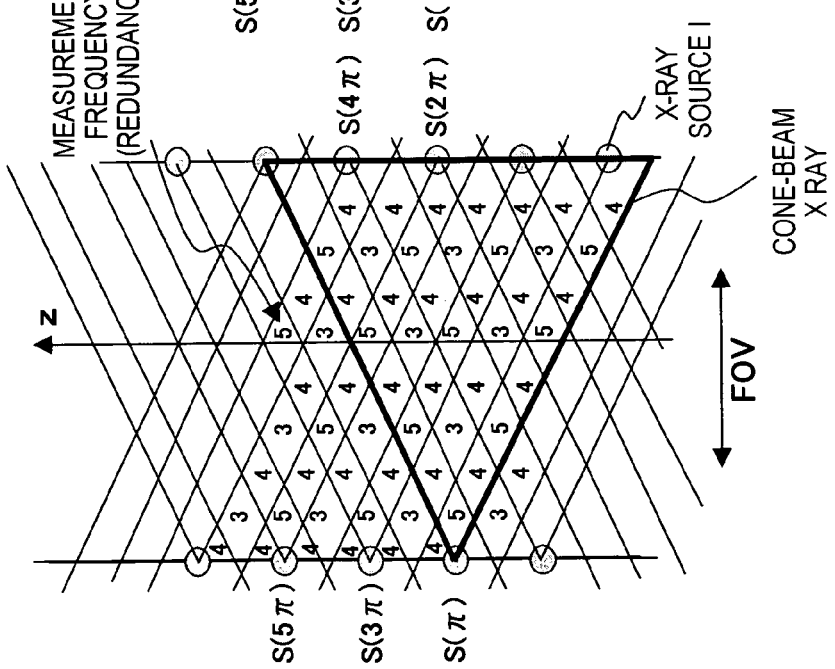

The effect in a case of ECG-gated reconstruction using a helical scan according to the above described flow will now be described. FIG. 11(a) shows a state in which a table feeding speed is slower than in FIG. 11(b), and FIG. 11(b) shows a state in which the table feeding speed is slower than in FIG. 11(c). These figures are views in which an object to be examined was observed from one direction, and the measurement frequency when the same portion is measured a number of times irrespective of redundancy, i.e. that collection of scanning data is completed, is noted. In FIG. 11(a), the measurement frequency is mixed between from three times to five times. In FIG. 11(b), the measurement frequency for the sides is twice, and the measurement frequency for the center part is three times. In FIG. 11(c), the measurement frequency for the center part is from one to three times. That is, as the table feeding speed decreases, the overall redundancy increases. The X-ray irradiation time in this case becomes longer, and thus the exposure increases. Meanwhile, when the table feeding is slow, the number of segments increases since the measurement frequency per unit time increases.

According to the conventional technology, temporal resolution is decided by the minimum measurement frequency during scanning, that is, the minimum number of segments. More specifically, although the number of segments for FIG. 11(a) is from three to five since the measurement frequency is between three and five times and a temporal resolution in accordance with the minimum number of three segments is obtained, there is a lot of radiation exposure because the table feeding speed is slow. Similarly, in FIG. 11(b), since the measurement frequency is between two and three times, a temporal resolution in accordance with the minimum number of two segments is obtained, and since the table feeding speed is faster than in FIG. 11(a) the exposure is less than in FIG. 11(a). Similarly, in FIG. 11(c), since the measurement frequency is between one and three times, a temporal resolution in accordance with the minimum number of one segment is obtained, and the exposure is less than in FIG. 11(b). More specifically, the slower the table feeding speed, although an advantage is obtained that the temporal resolution is high and image quality is enhanced, on the other hand redundancy and ineffective radiation exposure increase. A contradiction thus arises with respect to a desirable result.

According to this embodiment all measured data within the FOV is offered for reconstruction. More specifically, in FIG. 11(a), since all of the segments, numbering from three to five, within the FOV are used, reconstruction is enhanced in comparison with the conventional technology in which the minimum number of three segments is uniformly used. In FIG. 11(b), since three is used for the number of segments within the FOV, the temporal resolution within the FOV is enhanced in comparison with the conventional technology in which the minimum number of two is used. In FIG. 11(c), since the number of segments from one to three within the FOV are used, the temporal resolution within the FOV is enhanced in comparison with the conventional technology in which the minimum number of one is used.

Figure 12:
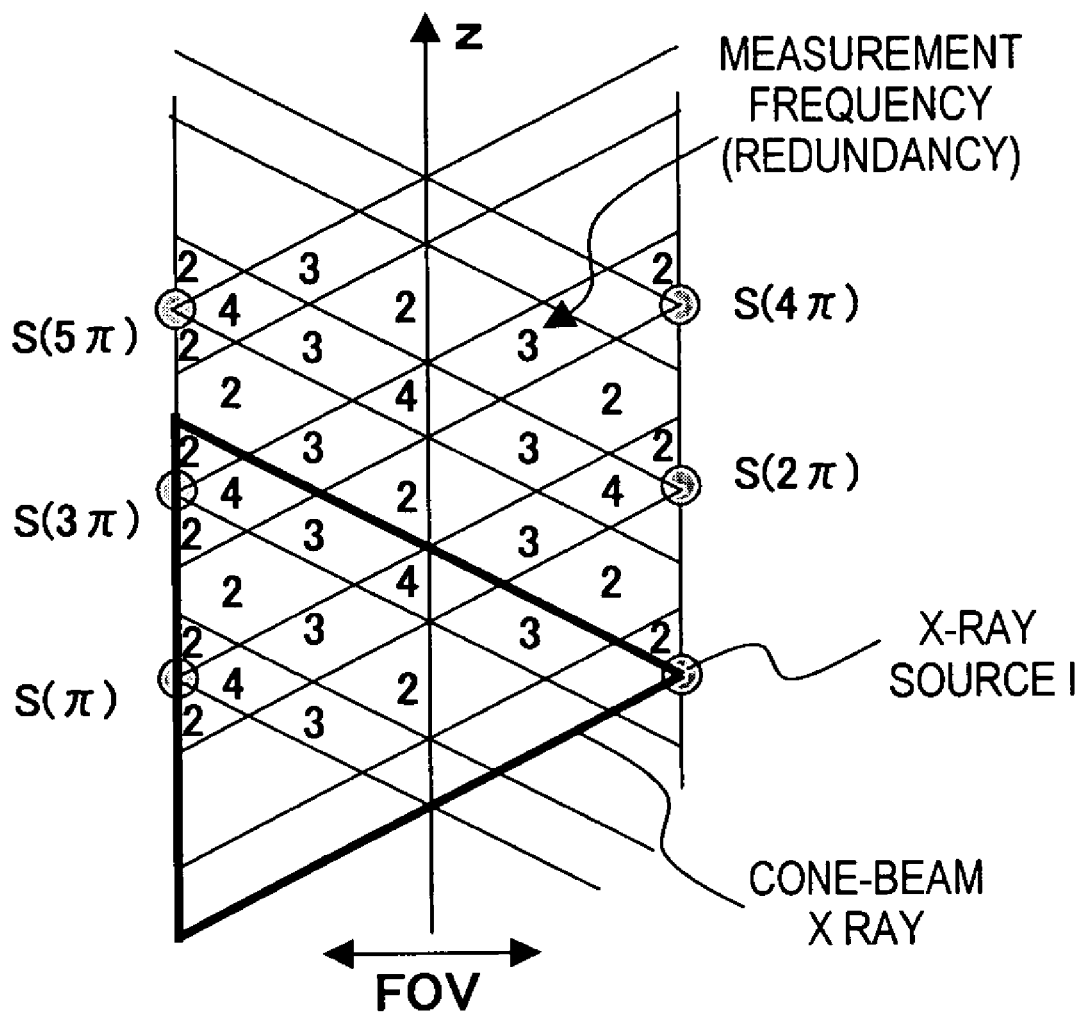
FIG. 12 is a view that describes redundancy produced by a difference in table feeding speeds.

FIG. 12 shows one example of measurement frequency in a case of a circular scan according to the present embodiment. According to this embodiment, reconstruction is performed using from the number of segments from two to four within the FOV. Since a temporal resolution in accordance with a minimum number of two segments is obtained according to the conventional technology, the temporal resolution within the FOV is enhanced in comparison with the conventional technology.

As described in the foregoing, according to this invention, since a configuration is adopted that is capable of using scanned data as much as possible, it is possible to improve temporal resolution as far as possible within the area of the scanning data while reducing ineffective radiation exposure. It is therefore possible to reconstruct and image minute parts with intense movement, such as the cardiac coronary artery terminus, under a condition of low ineffective radiation exposure.

SECOND EMBODIMENT

The second embodiment follows substantially the same procedures from step S201 to step S204 in FIG. 2 as described in the first embodiment. Consequently, unless specifically stated otherwise, the reference symbols used for this embodiment are the same as those used in Embodiment 1. While according to the first embodiment the relocation relating to FIG. 6 was related to full reconstruction performed in a $2\pi$ (360°) area, in Embodiment 2 half reconstruction is performed in a $\pi$ (180°) area. Hereunder, Embodiment 2 is described with reference to FIG. 2 and FIG. 13.

In step S205 in FIG. 2, a segment width is calculated. First, it is assumed that up to step S204, X-ray transmission data as shown in FIG. 13(a) was obtained. Reference segment positions 65 to 69 shown in FIG. 13(a) are, for example, segment data that correspond to the reference segment positions 61 to 65 that were recognized as effective segment positions in FIG. 5. In this case, L0 and L1 are the starting edge segment allowable maximum width and the finishing edge segment allowable maximum width, respectively, similarly to Embodiment 1. The starting edge segment allowable maximum width L0 is the distance between the starting edge of the reconstruction view area 70 and the reference segment position in the vicinity thereof. The finishing edge segment allowable maximum width L1 is the distance between the finishing edge of the reconstruction view area 70 and the reference segment position in the vicinity thereof. This distance is the critical value (limiting condition) with respect to the shape and width of a weight for reference segment positions described later. Next, as shown in FIG. 13(b), relocation is performed by repeating reference segment positions inside the reconstruction view area 70 for every $\pi$ (180°), to dispose the reference segment positions in a certain $\pi$ (180°) portion of the reconstruction area 70. When relocating the reference segment positions, the positions are disposed while matching the coordinates of a view phase (or circular phase).

At the time of this relocation, when there are segments of approximately the same cardiac phase it is better to select the segment that is closer to the center of the reconstruction view area. The reason being that it is difficult for the segment that is closer to the center of the reconstruction view area to generate artifacts since X rays are used in a state in which the cone angle that is the spread in the axial direction of the circulation axis Z of the cone beam is small. Alternatively, with respect to both of the segments of approximately the same cardiac phase as described above, synthesis may be performed by assigning weights such that the sum thereof is one. This is because artifacts can be alleviated by assigning weights. In this case, the reference segment positions 68 and 69 are disposed in approximately the same view phase (or circular phase). Therefore, since the reference segment position 68 is closer to the center of the reconstruction view area than the reference segment position 69 in FIG. 13(a), i.e. is the position nearer the center of the view area, in FIG. 13(c) the reference segment position 68 is used for reconstruction and the reference segment position 69 is not used for reconstruction. In this connection, in FIG. 13(c) the reference segment position included in each segment is not necessarily located at the center of the segment width.

Next, as shown in FIG. 13(d), the segment widths are adjusted so that segments located at the edges of the reconstruction view area are contained in the view area. At this time, adjustment is carried out so as not to exceed the aforementioned starting edge segment allowable maximum width L0 and the finishing edge segment allowable maximum width L1. As shown in FIG. 13(a), the starting edge segment allowable maximum width L0 corresponds to the distance between the reference segment position 65 and the starting edge of the reconstruction view area. When the weight of the reference segment position 65 extends past L0, it overruns the reconstruction view area. In that case, data that is different from the slice thickness that it is attempted to reproduce becomes mixed in with the desired data, and thus the spatial resolution is degraded and image quality deteriorates.

However, when it is desired to sacrifice spatial resolution to increase the temporal resolution or when deterioration in spatial resolution will not be a problem, a state in which the weight of the reference segment position 65 extends past L0 need not necessarily be avoided. Likewise, as shown in FIG. 13(a), the finishing edge segment allowable maximum width L1 corresponds to the distance between the reference segment position 69 and the finishing edge of the reconstruction view area. When the weight of the reference segment position 69 extends past L1, it overruns the reconstruction view area 70. In that case, data that is different from the slice thickness that it is attempted to reproduce becomes mixed in with the desired data, and thus the spatial resolution deteriorates. However, when it is desired to enhance temporal resolution more than spatial resolution or when deterioration of spatial resolution will not be a problem, a state in which the weight of the reference segment position 65 extends past L0 need not necessarily be avoided.

According to the present embodiment, since the reference segment position 69 is deleted in FIG. 13(c) it is not necessary to pay attention so that the weight of the segment does not extend past the finishing edge segment allowable maximum width L1, and it is sufficient to perform adjustment so that the weight of the reference segment position 65 does not extend past the starting edge segment allowable maximum width L0. In FIG. 13(c), since the segment width w1 extends leftward from the above described certain $2\pi$ region, the width of the segment width w1 is narrowed. As a result of this adjustment, as shown in FIG. 13(d), all of the segment widths are contained in the area of $2\pi$. Thereafter, reconstruction is carried out through the same processing as that of steps S206 and S207 of the first embodiment.

According to this embodiment, since segments required for reconstruction are from a 180° direction, image reconstruction can be carried out based on segments collected by scanning that further decreased radiation exposure. In this case also, the scanned data can be effectively utilized to the maximum to enable enhancement of temporal resolution. Accordingly, the relation between radiation exposure and temporal resolution can be optimized.

Although a tomographic apparatus that uses X rays is used according to this embodiment, the present embodiment is not limited thereto, and it can also be applied to a tomographic apparatus that uses gamma rays, neutron rays, positrons, electromagnetic energy or light.

THIRD EMBODIMENT

Although the processing of step S202 in the third embodiment is different to that of the first embodiment, the other steps are the same as those of the first embodiment and therefore a description of those steps is omitted. Hereunder, the difference with the first embodiment is described. Unless specifically stated otherwise, the reference numerals used correspond to the parts that are the same as in the first embodiment.

Although in the prior art the segments to be used for reconstruction are uniformly determined for the entire tomogram, and in the first embodiment the reconstruction view area 70 was calculated according to the FOV, according to the present embodiment the reconstruction view area 70 is calculated for each pixel.

In FIGS. 3(a) and (b), when a reconstruction pixel position is taken as I (xi,yi,zi), the position of an X-ray source is taken as S (xs,ys,zs), and row denotes the number of rows of the detector, the width R [rad] of a reconstruction view area is, for example, as shown in Formula 9 below.

[Formula 9]

$$R = dapp * (\text{row} - 1) * \frac{\sqrt{(xi - xs)^2 + (yi - ys)^2 + (zi - zs)^2}}{SID} * \frac{2\pi}{T} \quad (9)$$

Even when reconstruction is performed within the reconstruction view area 70 that was determined in this manner, the occurrence of artifacts is small since the reconstruction view area 70 does not change greatly between neighboring pixels. In this connection, the above described method of calculating the reconstruction view area 70 represented in Formula 9 is only one example, and a calculation method is not limited thereto. Further, since the reconstruction view area 70 will vary according to the operational precision in the body axis direction of the reconstruction algorithm, it is not limited to a single value.

According to this embodiment, instead of making the image slice thickness thicker to lower the precision in the body axis direction, a wider reconstruction view area 70 can be used. For example, although when there is a lot of noise, the noise can be reduced by intentionally increasing the slice thickness, at that time the temporal resolution can be further enhanced by determining a wider reconstruction view area 70 for each pixel according to the present embodiment. More specifically, although the spatial resolution is not high, an image that has high temporal resolution and low noise is obtained.

In this connection, in Formula 9, row denotes the number of rows of the detector, and for example, in the case of a detector with four rows, row=4. However, by using a known extrapolation method it is possible to form six rows by creating one row before and after the data from the four-row detector by interpolation. Alternatively, it is possible to expand the data of the outside detector rows by the amount of one row as a row including the same data. By adding assumed detector rows before and after the data by extrapolation or expansion in this manner, it is possible to improve the temporal resolution further since the data in the direction of the time axis of the cardiac phase increases. It is also possible to perform extrapolation or attachment of a row width that is a multiple of a decimal number that is less than 1 row, such as 0.5 rows, and this is effective in a case where data in the time axis direction is slightly lacking.

Although a tomographic apparatus that uses X rays is used according to this embodiment, the present embodiment is not limited thereto, and it can also be applied to a tomographic apparatus that uses gamma rays, neutron rays, positrons, electromagnetic energy or light.

FOURTH EMBODIMENT

The fourth embodiment is a method of extracting X-ray transmission data that is X-ray transmission data for electrocardiogram (ECG) reconstruction that can further reduce motion artifacts. First, the X-ray transmission data extraction method according to this embodiment will be described in comparison with the prior art.

In the prior art, for example Japanese Patent Laid-Open No. 2002-330961 discloses an X-ray CT apparatus that collects, from a plurality of heartbeats, X-ray transmission data of different views or scans that were scanned in approximately the same cardiac phase based on R waves of an electrocardiographic waveform. It is possible to attempt to enhance the temporal resolution by performing image reconstruction based on X-ray transmission data that was collected in this manner. FIG. 14 illustrates an X-ray transmission data extraction method according to the prior art.

FIG. 14(*a*) shows phases 191R, 192R, 193R . . . in which there is an R wave signal of an electrocardiographic waveform among the electrocardiogram data that was obtained from an electrocardiograph. According to the reconstruction of the first embodiment to the third embodiment, as shown in FIG. 14(*b*), weights 191, 192, 193 . . . generated that centered on positions 191C, 192C, 193C . . . that were offset on the basis of RR signals 191R, 192R, 193R . . . of an electrocardiographic waveform. Therefore, there was a high possibility of the weights 191, 192, 193 . . . straddling phases with a large movement, such as a P wave or R wave included in the electrocardiographic waveform. There was thus a problem that motion artifacts were liable to be produced because of straddling of phases with large movement (phases surrounded by a dotted line). There was also a problem that individual differences exist with respect to the optimal offset amount when determining reference positions for calculating the weightings.

The X-ray CT apparatus according to the fourth embodiment was designed in consideration of the above described problems, and it can realize fewer motion artifacts using the equivalent electrocardiogram information as heretofore in ECG reconstruction, and also address individual differences in an optimal offset amount.

Figure 15:
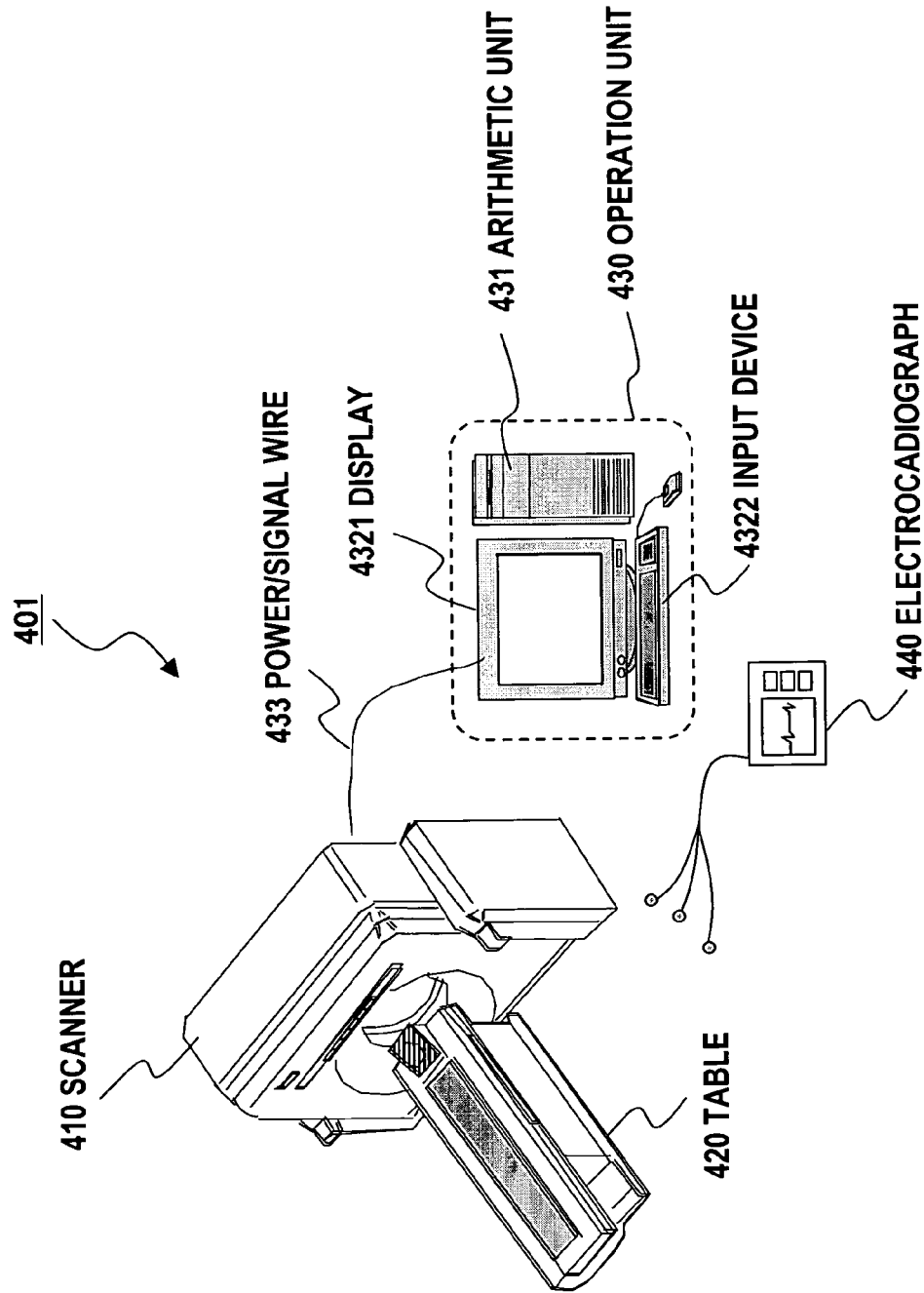
FIG. 15 is an overall profile view showing the configuration of an X-ray CT apparatus according to the fourth embodiment.
Figure 16:
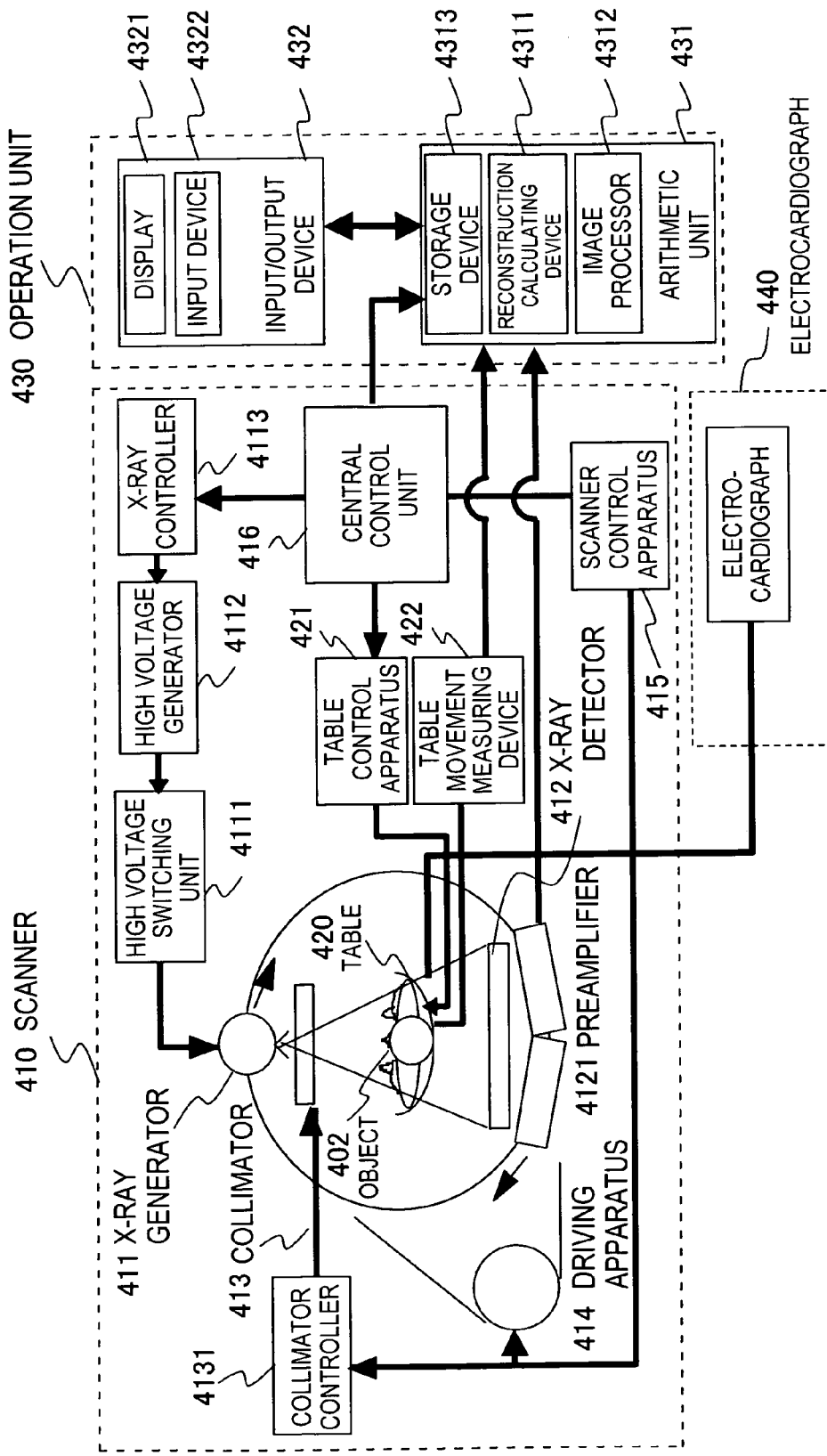
FIG. 16 is a block diagram that illustrates the configuration of the X-ray CT apparatus according to the fourth embodiment.

FIG. 15 is an overall profile view showing the configuration of an X-ray CT apparatus to which the present embodiment is applied. FIG. 16 is a block diagram that illustrates the configuration of the X-ray CT apparatus shown in FIG. 15.

An X-ray CT apparatus 401 shown in FIG. 15 mainly comprises a scanner 410 and an operation unit 430 which are connected to each other by a power/signal wire 433. The X-ray CT apparatus 401 also comprises a table 420 on which an object to be examined 402 lies, and is connected to an electrocardiograph 440 as device that recognizes a periodic motion of the object 402.

The scanner 410 comprises an X-ray source that consists of an X-ray generator 411, a high voltage switching unit 4111, a high voltage generator 4112 and an X-ray controller 4113; the table 420 on which the object 402 lies; an X-ray detector 412 that is disposed facing the X-ray source to sandwich the object 402 therebetween; and a preamplifier 4121 that converts X rays that were detected by the X-ray detector 412 to electric current, performs amplification thereof, and outputs this to an arithmetic unit 431 as X-ray transmission data. The scanner 410 further comprises a collimator 413 that is disposed between the X-ray source and the object 402 to restrict X rays, and restriction device that is constituted by a collimator controller 4131. The scanner 410 also comprises a driving apparatus 414 that is disposed at the outer periphery of the object 402 and rotates the scanner 410 in a circumferential direction, a scanner control apparatus 415, and a central control unit 416 that controls these components.

The operation unit 430 comprises an arithmetic unit 431 that reconstructs and image based on electrocardiogram data acquired from the electrocardiograph 440 and X-ray transmission data acquired from the preamplifier 4121, and an input/output device 432 that includes an input device 4322 comprising a keyboard or pointing device such as a mouse and a display 4321. The arithmetic unit 431 comprises a reconstruction calculating device 4311 that performs a back-projection operation based on an X-ray transmission data signal (X-ray transmission data), an image processor 4312 that performs other image processing, and a storage device 4313 for storing data.

When an operator uses the input device 4322 to input scanning conditions, that is, the table movement speed, tube current, tube voltage, slice position, or reconstruction conditions (reconstruction high image quality mode, reconstruction high-speed mode, reconstruction spacing, reconstruction FOV, image size and the like), the central control unit 416 sends control signals required for scanning based on those scanning conditions to the X-ray controller 4113, the table control apparatus 421 and the scanner control apparatus 415. Thereafter, upon receiving an image start signal, the X-ray CT apparatus 401 start scanning. When scanning starts, a control signal is sent to the high voltage generator 4112 by the X-ray controller 4113, to apply a high voltage to the X-ray generator 4111 through the high voltage switching unit 4111. The X-ray generator 411 then irradiates X-rays at the object 402.

Simultaneously thereto, the scanner control apparatus 415 sends a control signal to the driving apparatus 414. Thereby, the X-ray generator 411, the X-ray detector 412 and the preamplifier 4121 rotate in a circumferential direction around the circumference of the object 402.

In the case of a circular scan (dynamic scan), the table control apparatus 421 keeps the table 420 on which the object 402 is lying at a standstill and performs X-ray scanning. In the case of a helical scan, it causes the X-ray generator 411 and the like to move in a parallel manner in a circumferential axial direction. The movement speed of the table 420 that moves parallelly at this time is measured by the table movement measuring device 422 and input into the arithmetic unit 431. Further, in the case of perspective scanning (scanning of planar perspective images of an object to be examined 2), only the table 420 is moved in a state in which the X-ray generator 411, the X-ray detector 412 and the preamplifier 4121 are standing still.

The irradiation region of X rays that were irradiated from the X-ray generator 411 is restricted by restriction device such as the collimator 413. X rays that passed through the object 402 are detected by the X-ray detector 412. X rays that were detected by the X-ray detector 412 are converted to electric current, and then amplified by the preamplifier 4121 and output as X-ray transmission data signals to the arithmetic unit 431.

The reconstruction calculating device 4311 inside the arithmetic unit 431 performs reconstruction processing based on the X-ray transmission data signals that were input into the arithmetic unit 431, to thereby generate a reconstruction image. The image processor 4312 performs image processing on the reconstruction image, and stores the reconstruction image that underwent image processing in the storage device 4313 and also displays the image on the display 4321 as a CT image.

An electrocardiograph 440 is attached to the chest of the object 402. The electrocardiograph 440 measures the heartbeat of the object 402 to generate heartbeat data. This heartbeat data is input to the arithmetic unit 431.

Figure 17A:
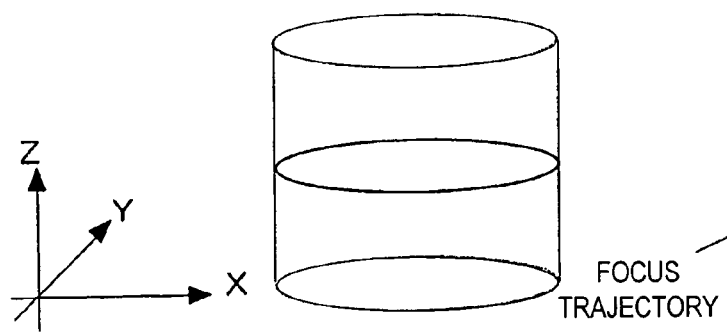
FIG. 17 consists of schematic diagrams that show the trajectories of an X-ray focus at the time of a circular scan and the time of a helical scan, in which (a) illustrates a circular scan and (b) illustrates a helical scan.
Figure 17B:
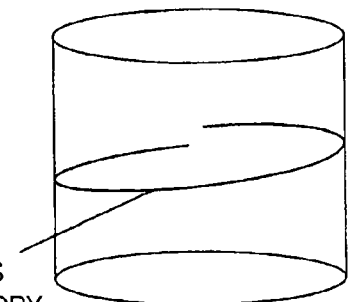

FIG. 17 shows schematic diagrams that illustrate the trajectories of an X-ray focus. FIG. 17(a) shows the trajectory of an X-ray focus in the case of a circular scan, and FIG. 17(b) shows the trajectory of an X-ray focus in the case of a helical scan. In the case of a circular trajectory, the X-ray focus draws a circular trajectory on the XY plane. In the case of a helical scan, the X-ray focus moves on the Z axis while a projected image of the X-ray focus draws a circular trajectory on the XY plane.

Figure 18A:
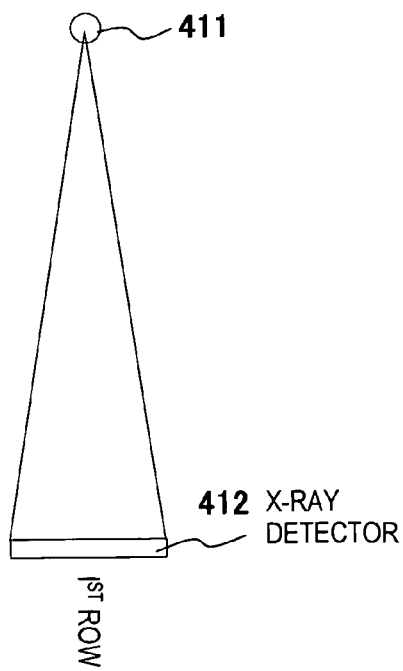
FIG. 18 consists of schematic diagrams that show the configuration of an X-ray detector 12, in which (a) illustrates a single slice and (b) illustrates multislices.
Figure 18B:
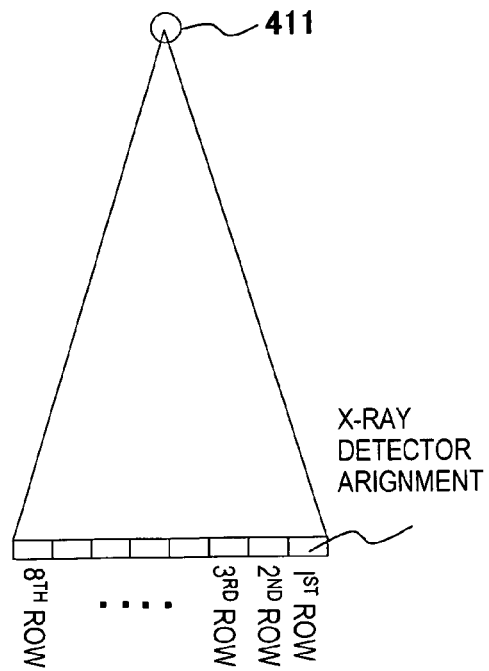

FIG. 18 is a schematic diagram that shows the configuration of an X-ray detector 412. FIG. 18(b) illustrates the case of an X-ray detector 412 that is used for a single-row detector CT apparatus (single-slice X-ray CT apparatus), and is formed by arranging the detector in only a single row. FIG. 18(a) illustrates the case of an X-ray detector 412 that is used for a multi-row detector CT apparatus (multislice X-ray CT apparatus), and is formed by arranging the detector in a plurality of rows. FIG. 18(b) illustrates an X-ray detector 412 with 8-rows, i.e. 8-slices.

FIG. 19 shows schematic diagrams that illustrate the thicknesses of X rays that are focused by a collimator. In the single-row detector CT apparatus in FIG. 19(a) and the multi-row detector CT apparatus in FIG. 19(b), X rays are focused to a thickness corresponding to the detector collimation thickness (slice thickness) at a position on the circulation axis by a separator mounted on the X-ray detector 412.

Figure 20:
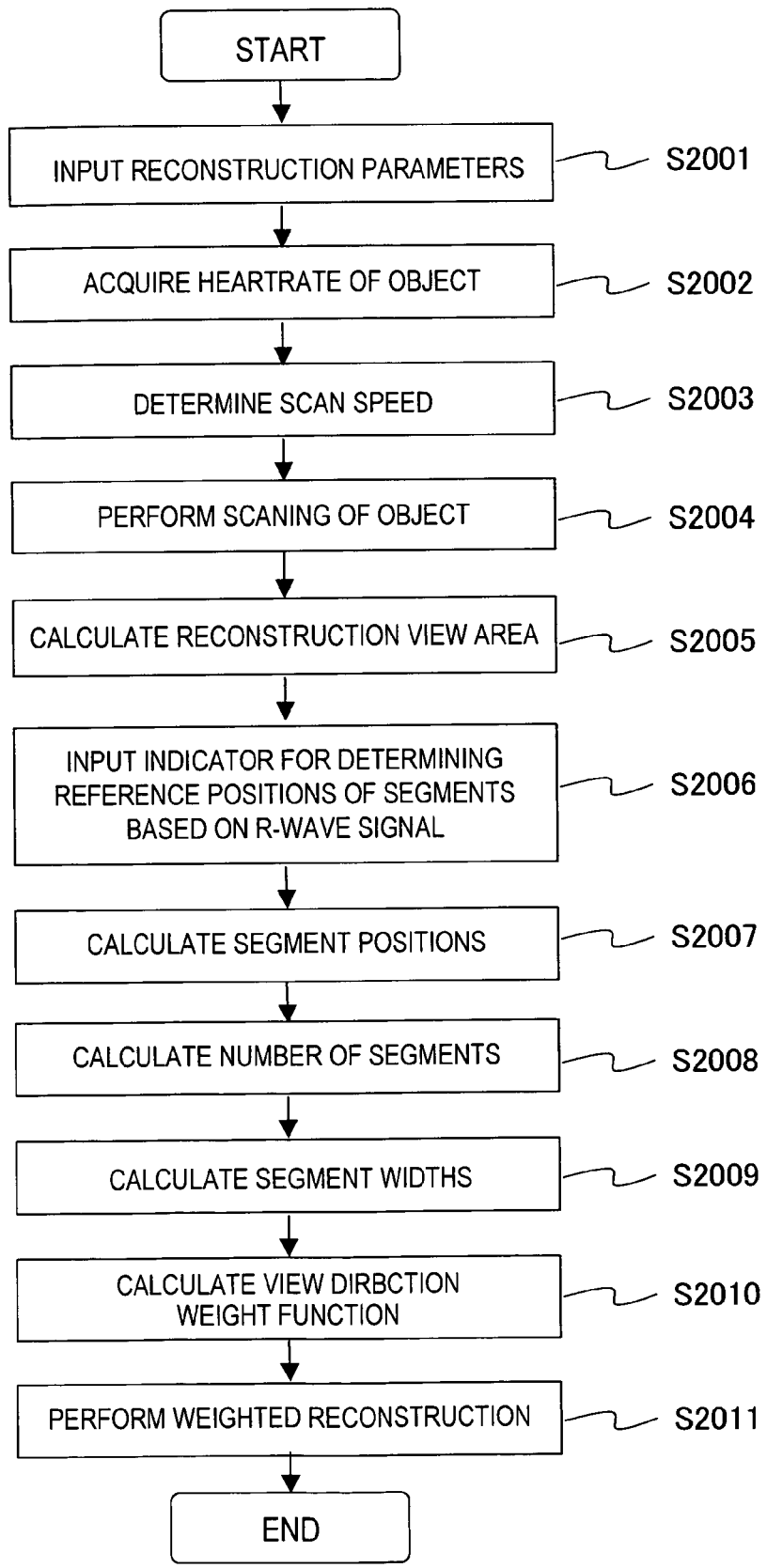
FIG. 20 is a flowchart that illustrates a method of assigning weights to view directions.

A method of collecting X-ray transmission data for the same cardiac phase and generating a cardiac reconstruction image with the above described X-ray CT apparatus 401 will now be described using FIG. 20.

(Step S2001)

The operator inputs the maximum number of segments and the table movement speed (or the helical pitch, redundancy, radiation exposure amount, or temporal resolution) using the input device 4322 having communication device, such as a mouse, a keyboard, a touch panel display or a voice input device (microphone), that communicates with the scanner 410, the scanner control apparatus 415 and the arithmetic unit 431 (S2001). The operator also inputs other reconstruction parameters, for example, FOV (pixel position), number of reconstruction matrices, and reconstruction mode (full reconstruction or half reconstruction). The initial values may also be input for the input parameters.

(Step S2002)

The heart rate of the object 402 is acquired by the electrocardiograph 440 (S2002).

(Step S2003)

The scan speed is decided based on the heart rate that was acquired in step S2002 (S2003).

(Step S2004)

The object 402 is scanned with that scan speed and the table movement speed that was input by the operator (S2004).

(Step S2005)

The arithmetic unit 431 calculates the maximum value of the view area that can be used for reconstruction for each pixel (S2005). The term "reconstruction view area" refers to a view area of the X-ray transmission data that contributes to reconstruction with respect to the cone beam reconstruction.

Methods for determining the reconstruction view area include a method of calculating the reconstruction view area in accordance with the FOV and a method of calculating the reconstruction view area in accordance with a pixel position. The reconstruction view area in accordance with the FOV can be calculated by the following formula.

$$FOM = ((FOV.x/2)^2 + (FOV.y/2)^2)^{(1/2)} \quad \text{[Formula 10]}$$

where, dapp: detector element size (body axis direction), row: number of detector rows, SOD: distance between X-ray source and center of rotation, SID: distance between X-ray source and detector, T: table movement speed, FOV: effective field of view, FOM: effective operation field of view, and FOV max: maximum effective field of view (Provided that, when FOM>FOV max (maximum FOV), then FOM=FOVmax)

Thus, a reconstruction view width [rad] can be calculated by the formula shown in Formula 11.

$$\text{reconstruction view width} = \text{CalcViewWidth\_FOM}(FOM) \quad \text{[Formula 11]}$$

A specific example is illustrated in the formula shown in Formula 12.

reconstruction view width=$dapp*(row-1)*(SOD-FOM/2)*2\pi(SID*T)$-arcsin$(FOM/(2*SOD))*2$ [Formula 12]

Calculation of a reconstruction view area in accordance with a pixel position can be performed using the following formula.

Using the same definitions as described above, and further, when taking a reconstruction pixel position as (xi, yi, zi), and taking an X-ray source position as (xs, ys, zs), the reconstruction view width [rad] can be calculated by the formula shown in Formula 13.

reconstruction view width=CalcViewWidth_Pixel(xi, yi, zi) [Formula 13]

A specific example is illustrated in the formula shown in Formula 14.

(reconstruction view width)=$dapp*(row-1)*(((xi-xs)^2+(yi-ys)^2+(zi-zs)^2)^(1/2))*2\pi(T*SID)$ [Formula 14]

The calculation method described above represents one example, and the method is not limited thereto. More specifically, the method will change depending on the operational precision in the body axis direction of the reconstruction algorithm, and is not limited to the above formula. The number of X-ray detector rows can be extended using extrapolation or nearest rows. Further, a predetermined number of scans, for example, three revolutions (0-6π) may be decided for the reconstruction view area.

(Step S2006)

Based on R wave information included in electrocardiogram information acquired from the electrocardiograph 440, the operator inputs an indicator for determining a reference position of a segment (reference segment position), for example, a segment shift index, a segment shift unit (relative method, absolute method), a segment shift method (terminus specifying method or the like), or a segment width index (S2006).

(Step S2007)

A reference segment position is calculated based on the indicator input in step S2006 (S2007).

Methods for calculating a reference segment position include an absolute method and a relative method. The methods are not limited to an absolute method and a relative method, and another known method may also be used.

Figure 21A:
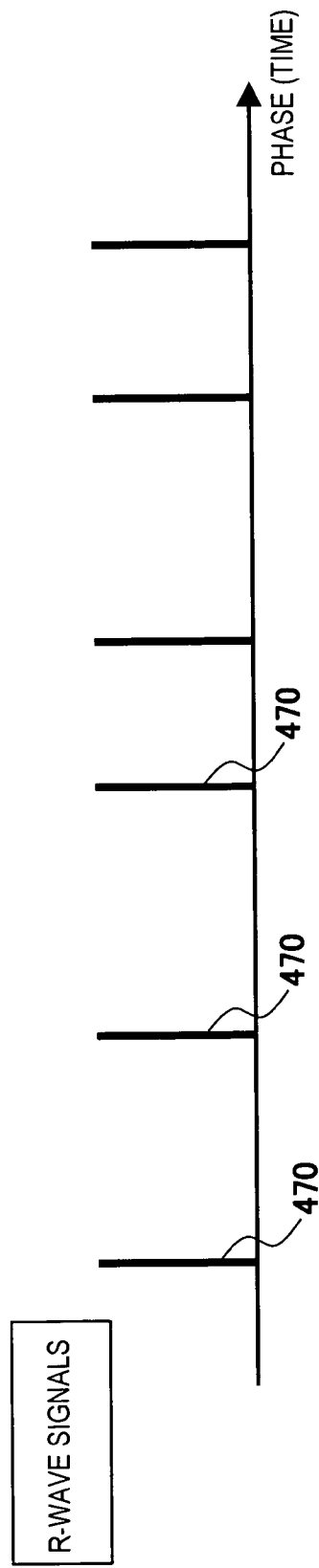
FIG. 21 consists of schematic diagrams that illustrate a method of calculating reference segment positions according to an absolute method, in which (a) illustrates R wave signals and (b) illustrates reference segment positions.
Figure 21B:
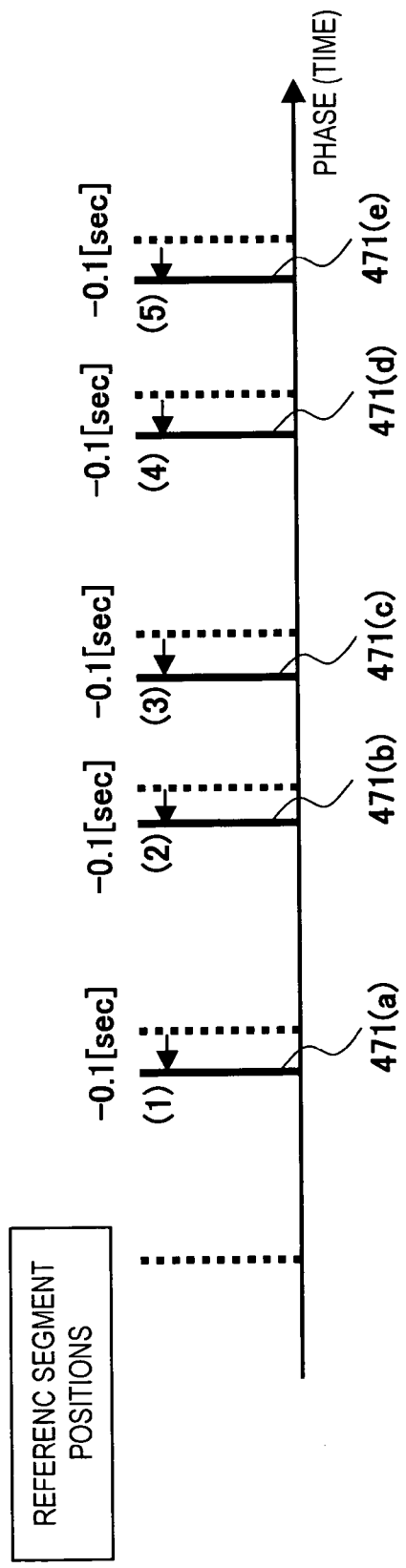

The above described absolute method is a method that calculates a reference segment position using an absolute time from a reference signal (an R wave included in electrocardiogram data acquired from the electrocardiograph 440). The value of the absolute time is decided by the operator. A method of calculating reference segment positions according to an absolute method will now be described based on FIG. 21. FIG. 21 is a schematic diagram illustrating a method of calculating reference segment positions according to an absolute method.

A reference segment position is calculated based on an R wave signal, a segment shift method, a segment shift index or a segment shift unit. For example, when a segment shift method is a terminus specifying method, a segment shift unit is the absolute method, and a segment shift index is −0.1 [sec], the reference segment position (in this case, a segment rear end position) is the position denoted by reference numeral 471 in FIG. 21, that is, a position 0.1 seconds before an R wave 470.

Next, a method of calculating reference segment positions according to a relative method will be described based on FIG. 22. FIG. 22 is a schematic diagram illustrating a method of calculating reference segment positions according to a relative method. The term "relative method" refers to a method that calculates reference segment positions using relative positions in a case in which a time interval from one reference signal (R wave) until a neighboring reference signal (R wave) is taken as 100%. The relative position values are determined by the operator. A segment position is calculated on the basis of an R wave signal, a segment shift method, a segment shift index and a segment shift unit. For example, when a segment shift method is a terminus specifying method, a segment shift unit is the relative method, and a segment shift index is an RR interval of 70%, the reference segment positions (in this case, segment rear end positions) are positions at intervals of 0.7 between the adjacent R waves 480, 480, i.e. 481a, 481b, 481c . . . .

(Step S2008)

The number of effective segments in accordance with a pixel position (FOV) is calculated based on electrocardiogram information (R wave) and the reconstruction view area that was calculated in step S2005 (S2008).

The number of effective segments (number of segments used in reconstruction) is taken as the number of signals that indicate a segment position in the reconstruction view area. Calculation of the number of effective segments will be described later based on FIG. 23.

(Step S2009)

The reference segment positions are relocated in an Nπ area. Segment widths are then calculated based on the relocated reference segment positions (S2009). More specifically, a certain reference segment position is disposed in the reconstruction view area 90 by repeating (relocating) it within a 360° range for full reconstruction or a 180° range for half reconstruction, and the segment width is calculated based on the reconstruction view area 90 and adjoining reference segment positions. A method for calculating the segment width is described later referring to FIG. 23.

(Step S2010)

A weight function is calculated based on each reference segment position so that the contribution ratio of the center position of the segment is high and the sum of weights for each phase and the opposing phase is equal (S2010).

By totaling up the weight of each segment for each phase, a final weight function of the view direction is generated. Weight generation for each segment is described later based on FIG. 23.

(Step S2011)

Reconstruction is performed with an existing weighted cone beam back-projection algorithm or a weighted 2D back-projection algorithm using the weight function created in step S2010 (S2011). Hereunder, an example is described of back projection that uses realignment processing from fan beams to parallel beams.

Initially, two-dimensional reconstruction will be described. First, a view area to be subjected to back projection is calculated according to the formula shown in Formula 15.

$$Be(z)=Bs(z)+2\pi F$$ [Formula 15]

Provided, 2πF: reconstruction data width

Next, the X-ray transmission data of the view area calculated by the formula shown in Formula 15 is extracted, and realignment processing (rebinning) that performs realignment from fan beams to parallel beams is carried out according to the formula shown in Formula 16.

$$P_{para}(\phi,t,v)=P_{fan}(\phi+\alpha,\alpha,v) \quad \text{[Formula 16]}$$

Figure 24A:
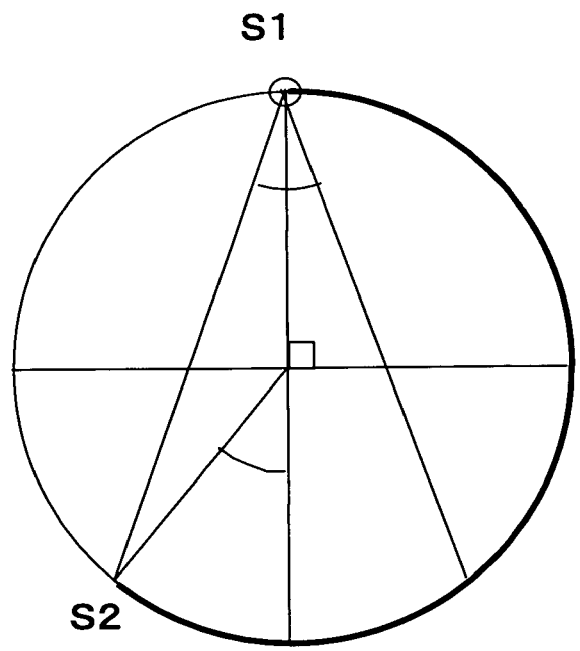
FIG. 24(a) is a schematic diagram showing a 180 degree reconstruction of fan beams and a parallel beam, and (b) is a schematic diagram showing a 180 degree reconstruction of parallel beams.
Figure 24B:
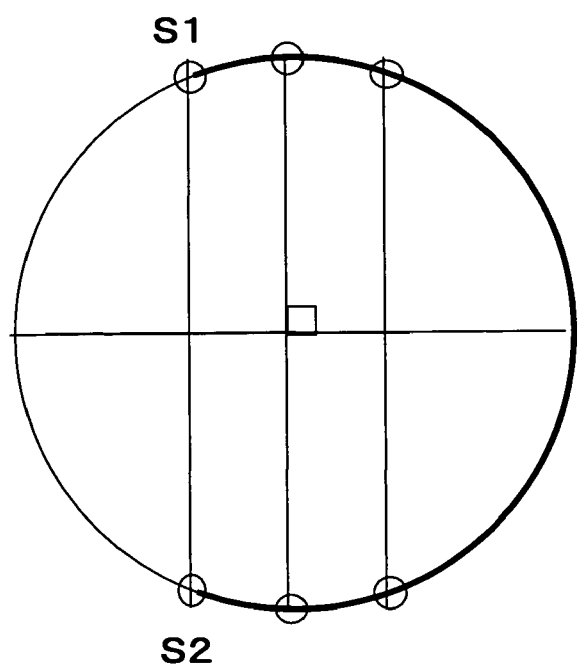

Provided, $P_{para}(\phi,t,v)$: parallel beam,
$P_{fan}(\phi+\alpha,\alpha,v)$: fan beam Fan beam reconstruction and parallel beam reconstruction in the case of a half scan will be described based on FIG. 24. FIG. 24(a) shows 180° reconstruction for fan beams, and FIG. 24(b) shows 180° reconstruction for parallel beams. The beam denoted by reference characters S1, S2 in FIG. 24(a) is converted to the beam denoted by reference characters S1, S2 in FIG. 24(b) by applying the formula shown in Formula 16 as described above.

Next, a reconstruction filtering process (recon filtering) in the detector channel direction is performed according to the formula shown in Formula 17 with respect to X-ray transmission data that was converted to parallel beams.

FIG. 25(a) is a three-dimensional reconstruction explanatory drawing for the X-Y plane, that shows the SOD, $\phi$, and X-ray source trajectory on the X-Y plane $S(\phi)$ used in a reconstruction filtering process. FIG. 25(b) is a three-dimensional reconstruction explanatory drawing for the X-Z plane, that shows the relation between a reconstruction image I (XI, yI, zI) and an X-ray source trajectory on the X-Z plane $S(\phi)$.

[Formula 17]

$$fP_{para}(\phi, t, v) = \int_{-\infty}^{\infty} \frac{SOD}{\sqrt{SID^2 + v^2}} P_{para}(\phi, t-t', v)g(t')dt'$$

Provided, SOD: distance between X-ray source and center of rotation;
SID: distance between X-ray source and detector;
F: reconstruction data width index; and
g(t'): reconstruction filter.

Next, weighted 2D back projection processing (back projection) is performed along the route of the beam in accordance with the formula shown in Formula 18 with respect to the X-ray transmission data after the filtering process.

[Formula 18]

$$I(x_I, y_I, z_I) = \frac{1}{\pi} \int_{Bs(z_I)}^{Be(z_I)} fP_{para}(\phi, v, t_I) \cdot W(\phi - Bs(z_I)) \cdot d\phi$$

Provided, I(XI, yI, zI): reconstruction image; and
$W(\phi-Bs(zI))$: weight function calculated in step S606.

Next, weighted reconstruction processing in the case of cone beam reconstruction is described.

First, a view area to be subjected to back projection is calculated according to the formula shown in Formula 19.

$$Be(x,y,z)=Bs(x,y,z)+2\pi F \quad \text{[Formula 19]}$$

Provided, $2\pi F$: reconstruction data width.

Next, the X-ray transmission data of the view area calculated by the formula shown in Formula 19 is extracted, and realignment processing (rebinning) that performs realignment from fan beams to parallel beams is carried out according to the formula shown in Formula 20.

$$P_{para}(\phi,t,v)=P_{fan}(\phi+\alpha,\alpha,v) \quad \text{[Formula 20]}$$

Provided, $P_{para}(\phi,t,v)$: parallel beam; and
$P_{fan}(\phi+\alpha,\alpha,v)$: fan beam.

Next, a reconstruction filtering process (recon filtering) in the detector channel direction is performed according to the formula shown in Formula 21 with respect to the X-ray transmission data that was converted to parallel beams.

[Formula 21]

$$fP_{para}(\phi, v, t_I) = \int_{-\infty}^{\infty} \frac{SOD}{\sqrt{SID^2 + v^2}} P_{para}(\phi, t-t', v)g(t')dt'$$

Provided, SOD: distance between X-ray source and center of rotation;
SID: distance between X-ray source and detector;
F: reconstruction data width index; and
g(t'): reconstruction filter.

Next, weighted cone beam back projection processing (back projection) is performed along the route of the beam in accordance with the formula shown in Formula 22 with respect to the X-ray transmission data after the filtering process.

[Formula 22]

$$I(x_I, y_I, z_I) = \frac{1}{\pi} \int_{Bs(x_I,y_I,z_I)}^{Be(x_I,y_I,z_I)} fP_{para}(\phi, v_I, t_I) \cdot W(\phi - Bs(x_I, y_I, z_I)) \cdot d\phi$$

Provided, I(XI, yI, zI): reconstruction image; and
$W(\phi-Bs(zI, yI, zI))$: weight function calculated in step S606.

It is thus possible to perform reconstruction in which weighting was carried out in the view direction.

Although calculation was performed according to a cone beam back projection method in the above described embodiment, calculation may also be performed using a three-dimensional Radon transformation method.

Figure 23A:
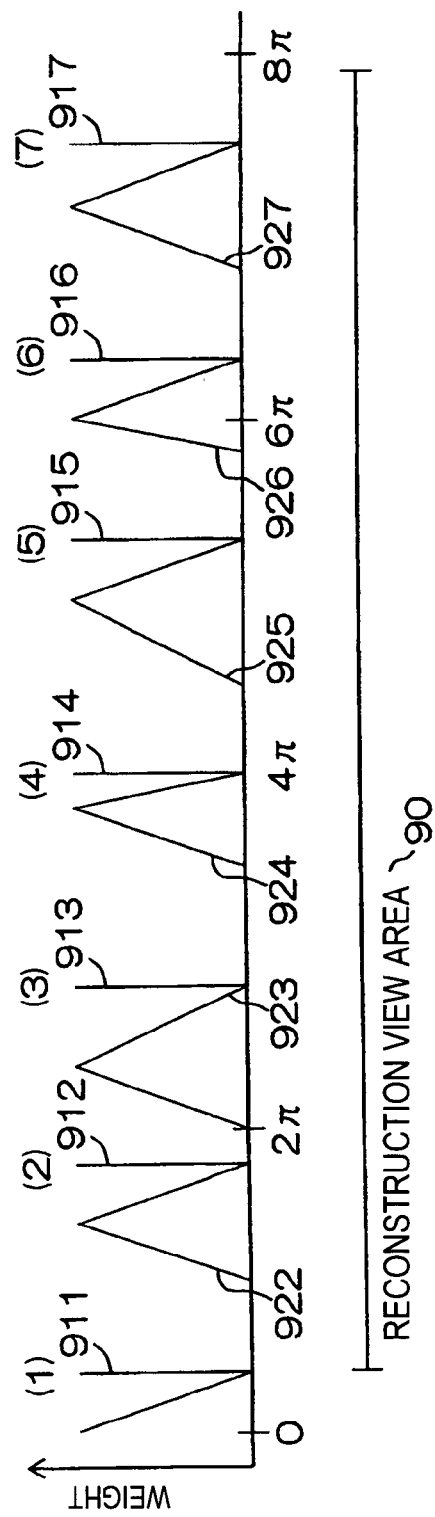
FIG. 23(a) is a schematic diagram illustrating a method of calculating segment weights that shows a view in which reference segment positions are represented in association with the actual phases, and (b) is a schematic diagram illustrating a method of calculating segment weights that shows a view in which reference segment positions are relocated in a range of 0 to 2π.
Figure 23B:
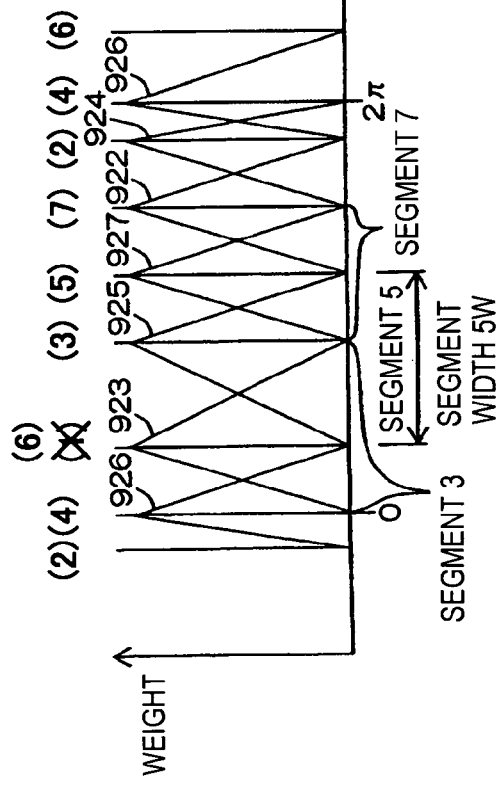

The above described reference segment position calculation and segment weight generation will now be described with reference to FIG. 23. FIG. 23(a) is a view in which reference segment positions are represented in association with actual phases, and FIG. 23(b) is a view in which reference segment positions are relocated in a range of 0 to $2\pi$.

The reconstruction view area 90 in FIG. 23(a) represents the reconstruction view area that was calculated in step S2005. Further, the reference segment positions 911, 912, 913, 914, 915, 916 and 917 represent reference segment positions calculated in step S2007. In FIG. 23(a), there are seven reference segment positions (hereunder, referred to as "effective segment positions"), i.e. 911, 912, 913, 914, 915, 916 and 917, included in the reconstruction view area 90. Accordingly, the number of segments calculated in step S2008 is seven. These effective segment positions are relocated in the 0 to $2\pi$ area. At this time, when segment phases overlap, the segment phase with the smaller cone angle (segment phase nearer the center of the reconstruction view area) is selected. In FIG. 23(a), the segment phases of the effective segment positions (1) and (6) overlap. In this case the effective segment position (6) is selected. The result obtained by relocation is shown in FIG. 23(b). The effective segment positions (1) to (7) shown in FIG. 23(b) correspond to the effective segment positions (1) to (7) shown in FIG. 23(a).

Next, the segment finishing edge position, segment center position, segment starting edge position and segment width of each segment are calculated based on the effective segment positions that were relocated. Hereunder, an example is described that calculates the segment center position, segment starting edge position and segment width of a segment (hereafter, referred to as "segment 5") that corresponds to the effective segment position (5).

First, the effective segment position (5) is set as the segment finishing edge position. Next, the segment center position of the segment 5 is determined. The segment center position is taken as the effective segment position (3) that is adjacent to the effective segment position (5) and is positioned in a phase prior to the effective segment position (5). Further, the segment starting edge position is taken as the effective segment position (6) that is positioned even further prior to the segment center position (in this example, the effective segment position (3)) and is adjacent to the segment center position.

Thereby, the segment 5 is calculated as a segment for which a segment width w5 is an area that starts at the effective segment position (6) and ends at the effective segment position (5) in which the segment center is the effective segment position (3). Similarly, the segment starting edge position, segment center position and segment width are calculated for all effective segment positions.

Next, a weight is created for each segment. The gable-shaped solid lines 926, 923, 925, 927, 922, 924 and 926 shown in FIG. 23(*b*) are weights. The weight 926 is a weight that corresponds to the effective reference segment position (6), and reference numerals 923, 925 and 927 denote weights that correspond to reference segments (3), (5) and (7).

The weighting method will now be described taking the weight 925 as an example.

The weights that correspond to each segment are set such that the segment center position in the relevant segment is the highest weight, and the segment starting edge position and segment finishing edge position are the lowest weights. With respect to the segment 5, the effective segment position (3) that corresponds to the segment center position is set as the highest weight "1", and the effective segment position (6) and effective segment position (5) that correspond to the segment starting edge position and segment finishing edge position are set as the lowest weight "0". Thus, the phases between the effective segment positions (6), (3) and (5) create a gable-shape weight 925 by use of a linear function of weights "0", "1" and "0". The other weights are generated in the same manner. In each phase that was relocated, a weight function is generated that continuously changes so that the sum of weights attached to adjacent segments is constant. For example, for segment 5, a weight function is set so that the sum of the weight 925 from the effective segment position (6) to the effective segment position (3) and the weight 923 of the segment 3 that is adjacent to segment 5 is continuously "1" for each phase. Likewise, for the area from the effective segment position (3) to the effective segment position (5), a continuously changing weight function is generated so that the sum of the weight 925 and the weight 927 of the segment 7 that is adjacent to segment 5 is constantly a weight "1" in each phase.

Weights generated in this manner are in the actual phases as shown in FIG. 23(*a*). Then, an image reconstruction process is performed by performing back projection processing by weighting the weights for each phase shown in FIG. 23(*a*) with respect to X-ray transmission data for the relevant phase.

Although the case of full reconstruction was described above, in the case of half reconstruction also, it is possible to relocate segment positions in a 0-π area and create a weight function in the same manner.

In this connection, although a weighting function was calculated using a linear function in this embodiment, it is possible to reduce discontinuity between segments by generating a weighting function using a non-linear function.

Figure 26A:
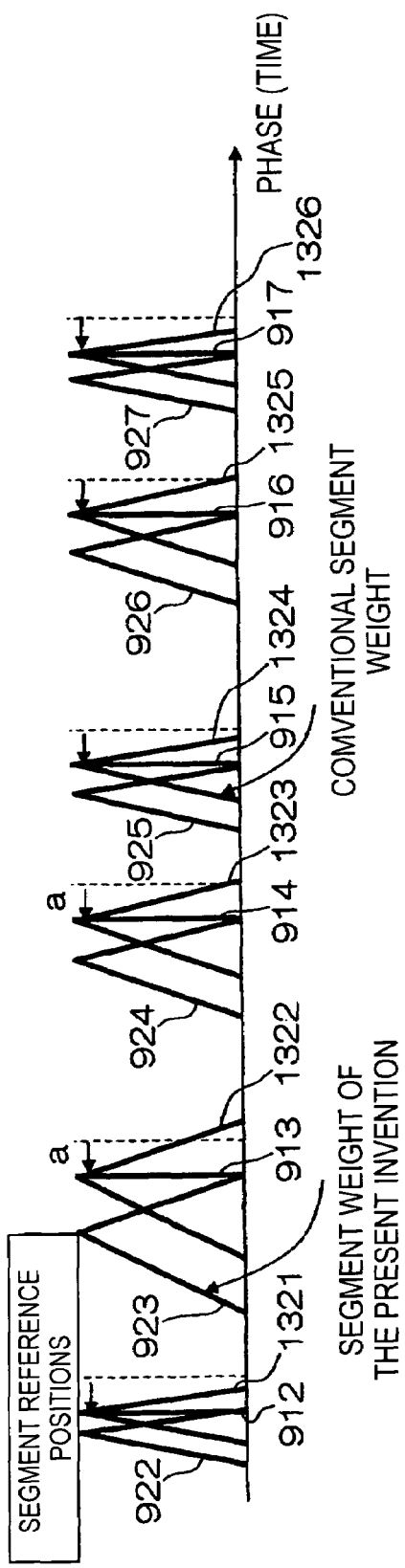
FIG. 26(a) is a schematic diagram showing a comparison between segment weights of the fourth embodiment and segment weights according to the prior art, and (b) is a schematic diagram showing a case in which the center position of the conventional segment weights shown in (a) are shifted to approach the center of the weights according to the fourth embodiment.
Figure 26B:
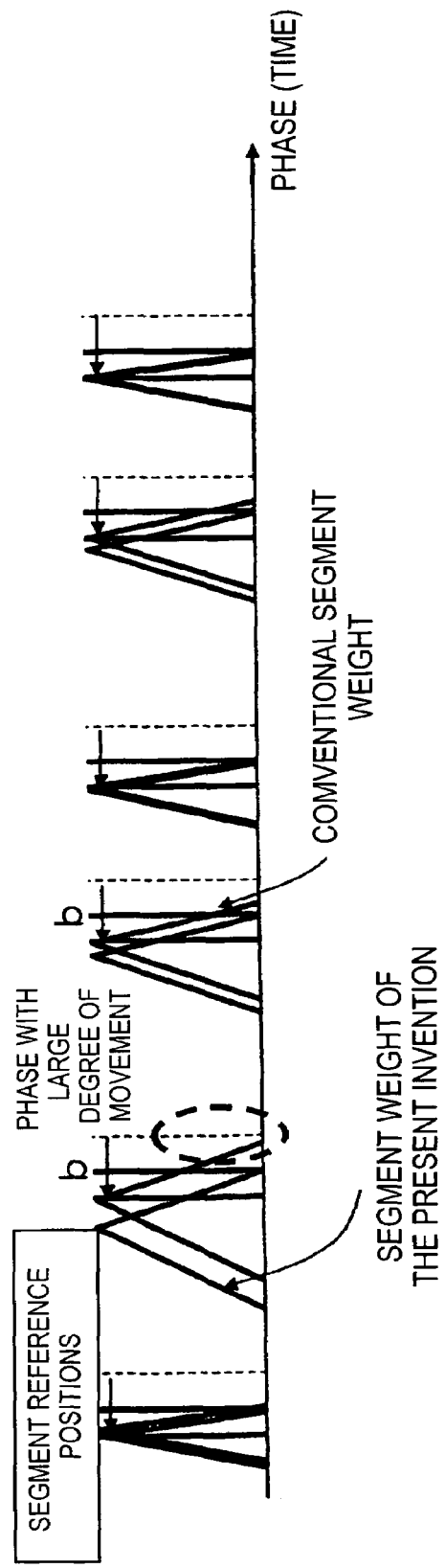

Next, segment weights according to this embodiment and the conventional segment weights are compared based on FIG. 26. FIG. 26 is a schematic diagram that illustrates a comparison between this embodiment and the prior art.

In FIG. 26(*a*), the phases before a phase based on an R wave signal are represented as reference segment positions 912, 913, 914 . . . . Conventional segment weights 1321, 1322, 1323 . . . are set so that the reference segment positions 912, 913, 914 . . . become the highest weights. For the segment weights of the present invention, segment weights 922, 923, 924 . . . are generated taking the reference segment positions 912, 913, 914 . . . as the finishing edges.

FIG. 26(*b*) is a view in which the center positions (912, 913, 914 . . . ) of the conventional segment weights in FIG. 26(*a*) are shifted so as to approach the center of the weights of the present invention. As shown by the location surrounded by a dotted line in FIG. 26(*b*), although with the conventional segment weights reconstruction is performed that includes a phase with a high degree of motion (position surrounded by dotted line), according to the segments of this embodiment, reconstruction is performed that does not include a phase with a high degree of motion.

Thus, with respect to the segments of this embodiment and the conventional segments, although the segment center positions are individually different, the segment widths are equivalent. More specifically, it can be said that in the present embodiment employs weights that do not use X-ray transmission data that was scanned in a phase with a high degree of motion with respect to the equivalent heartbeat phases as the conventional method.

Next, a variation of this embodiment will be described.

First, referring to FIG. 27, an embodiment will be described in which starting edge positions are determined by overlaying on reference segment positions. FIG. 27 consists of schematic diagrams that illustrate an embodiment that determines starting edge positions by overlaying on segments.

Reference numerals 131 to 134 in FIG. 27(*a*) denote reference segment positions after relocation (starting edge reference positions). According to a method that employs a starting edge of a segment as a reference segment position (hereunder, referred to as "starting edge reference method") as in the present invention, a reference segment position is disposed at a small position of the view positions for each segment. When reference segment positions after relocation overlap, as in the case of reference segment positions 132 and 134, the signal that is further from the center of the reconstruction view area (in this example, 134) is deleted (not used). According to a starting edge reference method, a reference segment position on the side on which an adjacent view is large is taken as the segment center position, and the reference segment position on the side on which a view adjacent to the segment center position is large is taken as the finishing edge reference position, and weights are generated so that weights are high in the segment center positions and weights are low at the edge reference positions (starting edge, finishing edge). In this example, for the relocated area shown in FIG. 27(*a*), it is necessary that weights are generated so that the total sum of weights of the same phase are constant for each view. By disposing the obtained weights in the view positions before relocation, a final weight function as shown in FIG. 27(b) is acquired. When determining the starting edge position of this segment, the above described relative method and absolute method are available. In FIG. 27(b), although the starting edge positions indicated by reference numerals 131 to 134 were determined as 70% positions of an RR signal based on a relative method, they may also be determined based on an absolute method, i.e. an R signal, for example as 0.3 sec.

Next, referring to FIG. 28, an embodiment will be described in which finishing edge positions are determined by overlaying on segments. FIG. 28 consists of schematic diagrams that illustrate an embodiment that determines finishing edge positions by overlaying on reference segment positions. Reference numerals 141 to 144 in FIG. 28(a) denote reference positions after relocation (finishing edge reference positions). According to a method that employs a finishing edge of a segment as a reference (hereunder, referred to as "finishing edge reference method") as in the present invention, a reference position is disposed at a large position of the view positions for each segment. When reference positions after relocation overlap, as in the case of reference positions 142 and 144, the signal that is further from the center of the reconstruction view area (in this example, 144) is deleted (not used). In the finishing edge reference method, a reference position on the side on which an adjacent view is small is taken as the segment center position, and the reference segment position on the side on which a view adjacent to the segment center position is small is taken as the starting edge reference position, and weights are generated so that weights are high in the segment center positions and weights are low at the edge reference positions (starting edge, finishing edge). In this example, for the relocated area shown in FIG. 28(a), it is necessary that weights are generated so that the total sum of weights of the same phase are constant for each view. By disposing the obtained weights in the view positions before relocation, a final weight function as shown in FIG. 28(b) is acquired. Similarly to the starting edge reference method, when determining the finishing edge position of this segment, the relative method and absolute method may be applied. In FIG. 28(b), although the starting edge positions indicated by reference numerals 141 to 144 were determined as 70% positions of an RR signal based on a relative method, they may also be determined based on an absolute method, i.e. an R signal, for example as 0.3 sec.

Next, referring to FIG. 29, an embodiment will be described in which segment center positions and starting edge reference positions are determined by overlaying on reference segment positions. FIG. 29 consists of schematic diagrams that illustrate an embodiment that determines segment center positions and starting edge reference positions by overlaying on reference segment positions. In FIG. 29(a), reference numerals 151C to 154C denote segment center positions after relocation, and reference numerals 151S to 154S denote starting edge reference positions after relocation. According to a method that employs a starting edge and a center of a segment and as a reference (hereunder, referred to as "center-starting edge reference method") as in the present invention, a starting edge reference position is disposed at a small position of the view positions for each segment and the segment center position is disposed at a position that is larger in comparison thereto. When reference segment positions after relocation overlap, as in the case of the positions denoted by reference numerals 152C and 154C, the signal that is further from the center of the reconstruction view area (in this example, 154C) is deleted (not used). In the center-starting edge reference method, a segment center position on the side on which a view adjacent to the segment center position is large is taken as a finishing edge reference position, and weights are generated so that weights are high at segment center positions and weights are low at the edge reference positions (starting edge, finishing edge). In this example, for the relocated area shown in FIG. 29(a), it is necessary that weights are generated so that the total sum of weights of the same phase are constant for each view. By disposing the obtained weights in the view positions before relocation, a final weight function as shown in FIG. 29(b) is acquired.

Next, referring to FIG. 30, an embodiment will be described in which center reference positions and finishing edge reference positions are determined by overlaying on segments. FIG. 30 consists of schematic diagrams that illustrate an embodiment that determines segment center positions and finishing edge positions by overlaying on reference segment positions. In FIG. 30(a), reference numerals 161C to 164C denote segment center positions after relocation, and reference numerals 161E to 163E denote finishing edge reference positions after relocation. According to a method that employs a finishing edge and a center of a segment and as a reference (hereunder, referred to as "center-finishing edge reference method") as in the present invention, a finishing edge reference position is disposed at a large position of the view positions for each segment and the segment center position is disposed at a position that is smaller in comparison thereto. When reference positions after relocation overlap, as in the case of the positions denoted by reference numerals 162C and 164C, the signal that is further from the center of the reconstruction view area (in this example, 164C) is deleted (not used). According to the center-finishing edge reference method, a reference segment position on the side on which a view adjacent to the segment center position is large is taken as a starting edge reference position, and weights are generated so that weights are high at segment center positions and weights are low at the edge reference positions (starting edge, finishing edge). In this example, for the relocated area shown in FIG. 30(a), it is necessary that weights are generated so that the total sum of weights of the same phase are constant for each view. By disposing the obtained weights in the view positions before relocation, a final weight function as shown in FIG. 30(b) is acquired.

Next, processing that is performed with respect to weight functions determined by the starting edge reference method (FIG. 27), the finishing edge reference method (FIG. 28), the center-starting edge reference method (FIG. 29) and the center-finishing edge reference method (FIG. 30) is described referring to FIG. 31. This is to prevent artifacts caused by weights remaining outside the reconstruction view area (however, the processing illustrated in FIG. 31 is applied only in a case where data is not created by extrapolation).

Figure 31A:
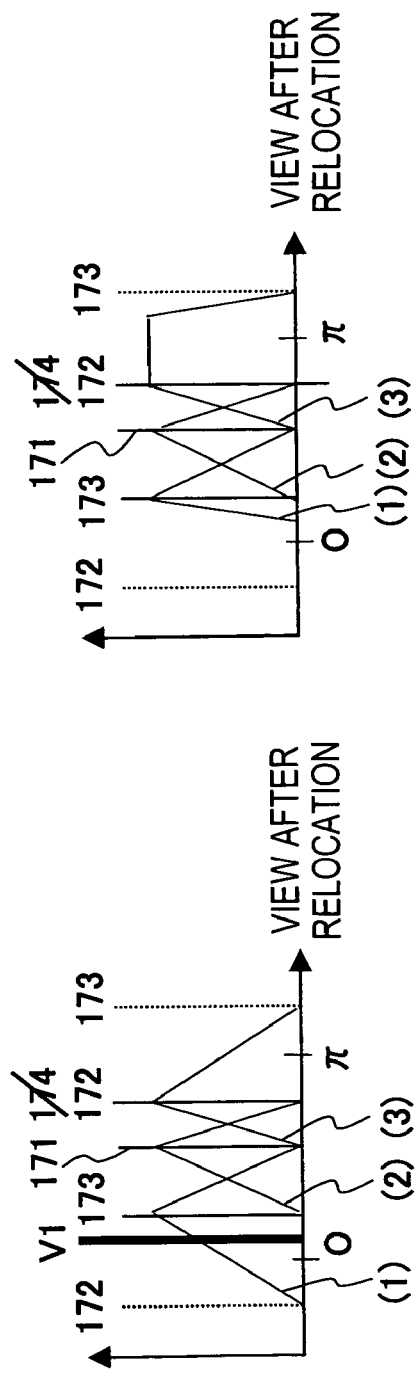
FIG. 31(a) is a schematic diagram for explaining correspondence processing with respect to restrictions caused by a reconstruction view area, which shows weight functions and reference segment positions after relocation; (b) is a schematic diagram for explaining correspondence processing with respect to restrictions caused by a reconstruction view area, which shows a view that was corrected to contain the weight functions of (a) in the reconstruction view area; and (c) is a schematic diagram for explaining correspondence processing with respect to restrictions caused by a reconstruction view area, which shows a state in which weight functions after correction are disposed at pre-relocation view positions.
Figure 31B:
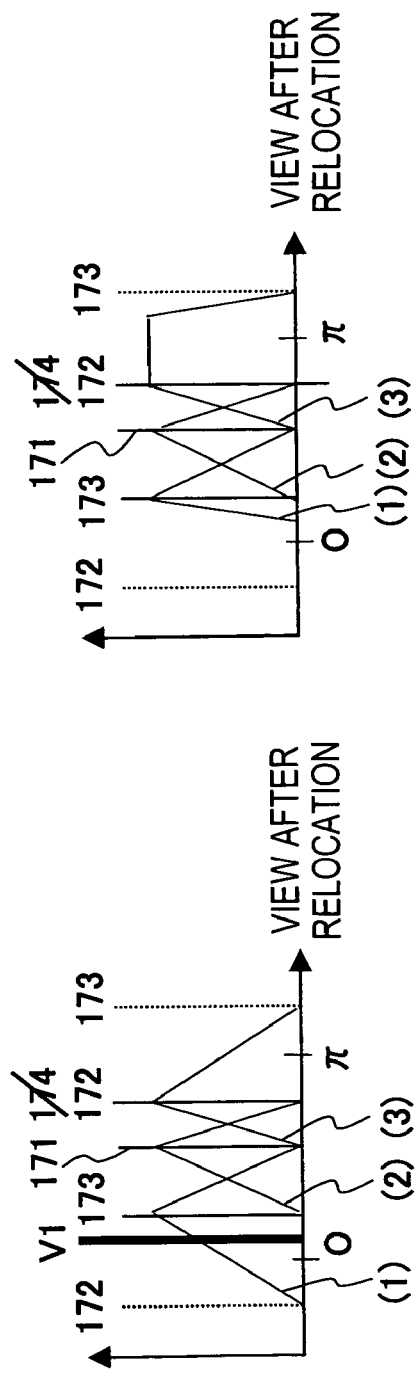
Figure 31C:
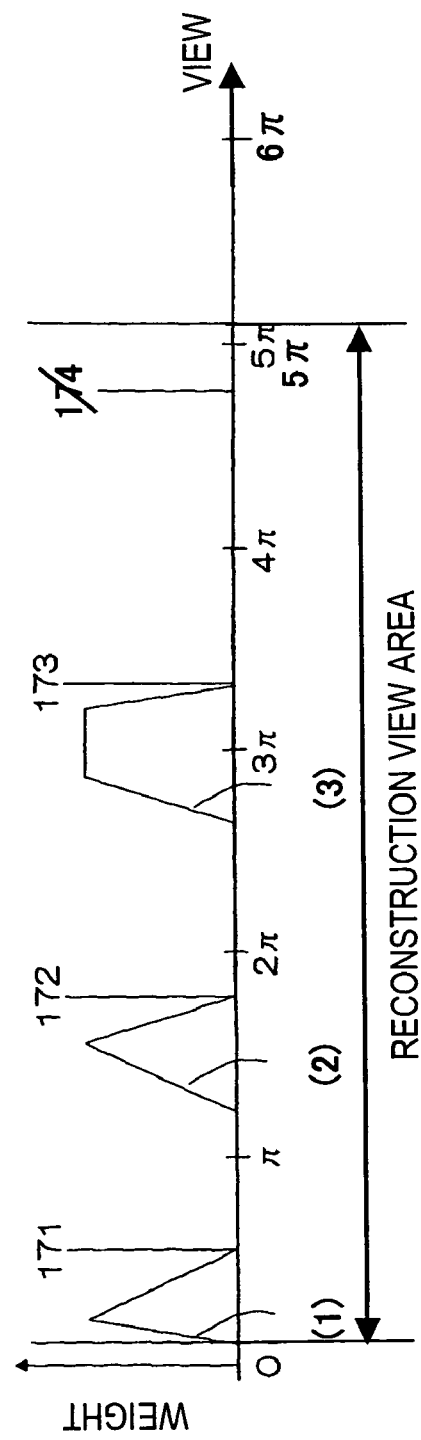

FIG. 31(a) shows a state in which a segment is set in which a segment center position is at a reference segment position, a starting edge reference position of the segment is a reference segment position that is positioned in an adjacent forward phase at a time of relocation, and a finishing edge reference position is a reference segment position that is positioned in an adjacent rear phase at a time of relocation, and weights are generated. When a generated weight exceeds the reconstruction view area (in this case, weight (1) corresponding to reference position 171), an adjustment is performed so as to include the weight in the reconstruction view area (FIG. 31(b)). More specifically, reference character v1 denotes the lower limit of the reconstruction view area, and since the weight (1) exceeds this, the weight (1) starting edge position is made to be v1, and the weights are adjusted so that the total sum of weights in the relocation phase is constant (in this case, the weight (3) corresponding to the reference position 173 is adjusted). As a result, weights can be generated such that the weight (1) does not exceed v1 and the total sum of weights for the relocation phase is constant (FIG. 31(c)).

Next, the manner of dealing with a case in which relocated phases were at the same reference position will be described referring to FIG. 32. When reference positions after relocation overlap as illustrated by reference positions 182 and 184 shown in FIG. 32(a), the signal that is further from the center of the reconstruction view area (184 in the above described) is deleted. Then, weights are generated based on the relocation phases after the deletion (FIG. 32(b)), and those weights are disposed at the view positions prior to relocation to obtain the final weight function (FIG. 32(c)). As a result, segments can be set without using a signal for which an error caused by the cone angle is large because it is far from the center of the reconstruction view area.

According to this embodiment, since the finishing edge of each segment is at a reference segment position, ECG reconstruction is performed without utilizing image data corresponding to a phase with a high degree of motion. Therefore, motion artifacts are fewer using the equivalent electrocardiogram information as heretofore, and individual differences in the optimal offset amount can also be dealt with.

Although a tomographic apparatus that uses X rays is used according to this embodiment, the present embodiment is not limited thereto, and it can also be applied to a tomographic apparatus that uses gamma rays, neutron rays, positrons, electromagnetic energy or light.

FIFTH EMBODIMENT

The fifth embodiment is a method that acquires a cardiac reconstruction image using an X-ray CT apparatus.

An X-ray CT apparatus irradiates X rays while rotating a rotating part equipped with an X-ray tube and an X-ray detector around the circumference of an object to be examined, and detects X rays that passed through the object's body with an X-ray detector. At this time, X-ray transmission data is collected in a manner such that a cardiac phase and rotational direction angle (hereunder, referred to as "view angle") are not identical for each rotation, and by obtaining by interpolation data of a desired slice position from the data collected in this manner, cardiac X-ray transmission data in a certain cardiac phase is arranged for an angle of at least 180°. Since a tomogram can be created by arranging data from an at least 180° direction, it is possible to collect data of a certain cardiac phase from a 180° direction or more in a period in which the rotating part rotates several times, to create a tomogram. In this connection, the term "certain cardiac phase" refers to, for example, immediately before a contraction phase in which the cardiac motion is comparatively stable.

At the time of this cardiography, to collect X-ray transmission data in a manner such that a cardiac phase and a rotational direction angle (hereunder, referred to as "view angle") are not identical for each rotation as described above, it is necessary to perform staggering so that cardiac cycle and the rotational cycle of the rotating part do not coincide. If these cycles do coincide, data required for reconstruction scanning will not be acquired irregardless of the number of times the rotating part is rotated. However, the efficiency of collecting X-ray transmission data and the extent of ineffective radiation exposure will vary depending on the extent of that staggering.

Therefore, conventionally, for example as disclosed in Japanese Patent Laid Open No. 2001-170044, in order to stagger the cardiac phase and view angle as described above in consideration of the aforementioned collection efficiency and ineffective radiation exposure, the rotation speed that is the scanning speed is uniquely determined as described below. More specifically, a rotation speed R is calculated by dividing the product of a helical pitch P and 60 by the product of a number obtained by subtracting 1 from a number of detector rows N and a heart rate B. According to this disclosure, a rotation speed R is calculated at which the heart rate of an object to be examined is controlled at a constant rate.

However, in fact it is rare that a heartbeat is constant and does not fluctuate. When the heartbeat fluctuates, scanning is performed under a heart rate that is different to the initially assumed heart rate, and the scanning speed thus deviates from a scanning speed that is suitable thereto. If the scanning speed deviates from the optimal scanning speed, the extent of ineffective radiation exposure or the efficiency of collection X-ray transmission data varies, and the temporal resolution that is an important factor in determining image quality is also affected.

Therefore, an object of the X-ray CT apparatus according to the fifth embodiment is to enable acquisition of images by high image quality scanning that have a high temporal resolution, even when the heartbeat at the time of scanning varies from the heartbeat at the time of setting the scanning speed.

Hereunder, a preferred embodiment of the X-ray CT apparatus according to the fifth embodiment is described in accordance with the attached drawings.

Figure 33:
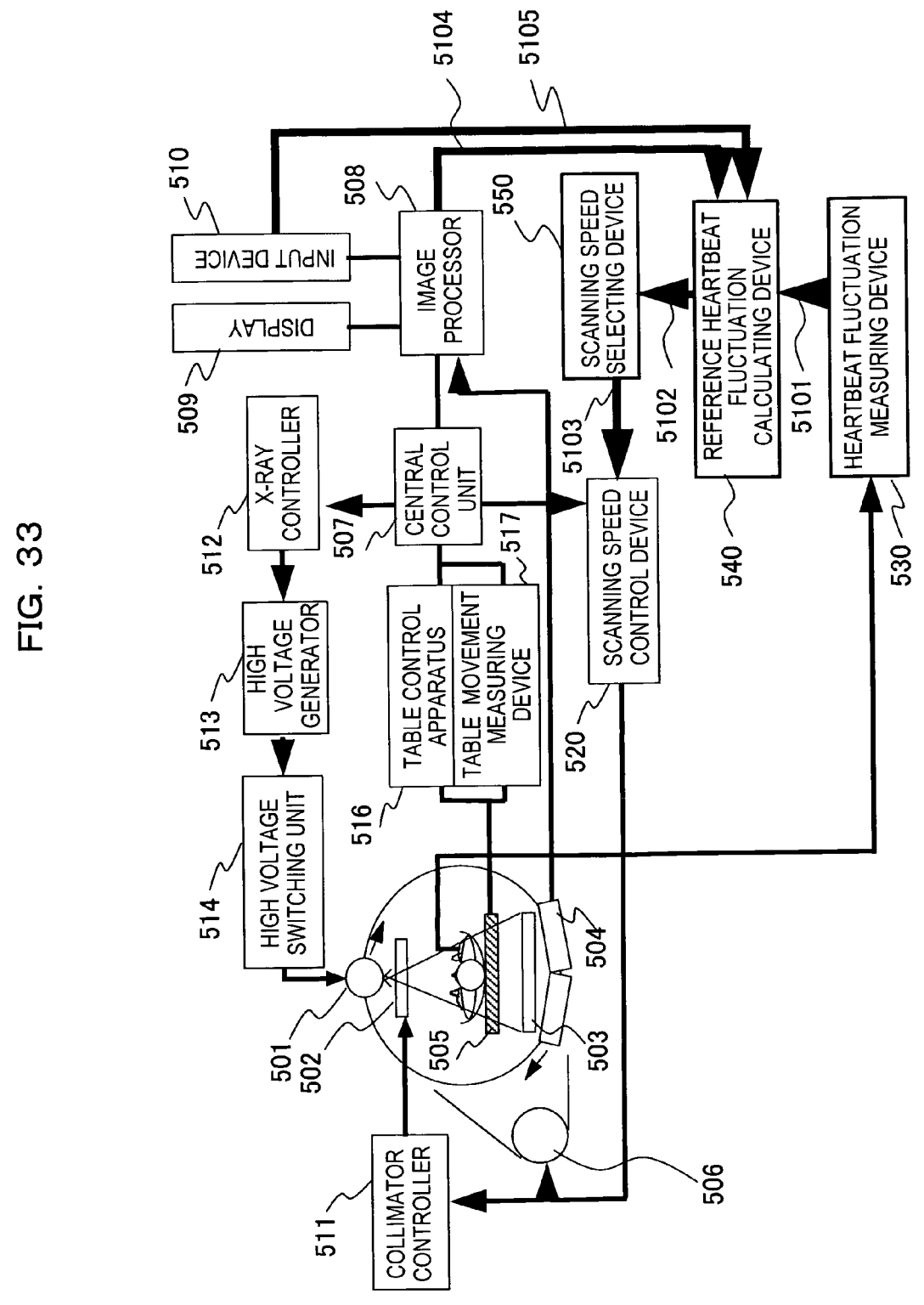

FIG. 33 is a view that illustrates an X-ray CT apparatus according to the fifth embodiment. The X-ray CT apparatus comprises an X-ray tube 501, a collimator 502, an X-ray detector 503 as radiation detection device, a preamplifier 504, a table 505, a rotational driving apparatus 506 that implements a predetermined scanning speed, a central control unit 507, an image processor 508, a display 509, an input device 510, a collimator controller 511, an X-ray controller 512, a high voltage generator 513, a high voltage switching unit 514, a scanning speed control device 520, a heartbeat fluctuation measuring device 530, a reference heartbeat fluctuation calculating device 540 and a scanning speed selecting device 550. However, the heartbeat fluctuation measuring device 530 need not necessarily be included in the configuration of the X-ray CT apparatus according to this embodiment, and it is sufficient that it can be connected separately from outside.

At the time of scanning, the high voltage generator 513 generates electric power as instructed by the X-ray controller 512 and sends the power to the high voltage switching unit 514, and the high voltage switching unit 514 applies a predetermined tube voltage and tube current to the X-ray tube 501. Upon receiving the tube voltage and tube current, the X-ray tube 501 emits an electron beam or the like to generate X rays by striking the electron beam against a target. X rays generated by the X-ray tube 501 are focused in accordance with a scanning site by the collimator 502, and then irradiated at the object on the table 505. X rays that passed through the object are collected by the X-ray detector 503. The transmitted X-ray data that was collected is sent to the image processor 508 to be scanned, and is displayed on the display 509 to make it available for use in diagnosis and the like.

In the configuration shown in FIG. 33, the characteristic parts of this embodiment are the scanning speed control device 520, the heartbeat fluctuation measuring device 530, the reference heartbeat fluctuation calculating device 540 and the scanning speed selecting device 550. These parts determine the scanning speed based on heartbeat fluctuation information prior to scanning. The interaction between these characteristic parts will now be described briefly. First, heartbeat fluctuation information that is obtained from the chest of the object is collected for a predetermined time by the above described heartbeat fluctuation measuring device 530. The collected data is sent to the reference heartbeat fluctuation calculating device 540 as an actual heartbeat waveform 5101 that represent a measurement heart rate and a heartbeat fluctuation amount. Based on the above described actual heartbeat waveform 5101, the reference heartbeat fluctuation calculating device 540 determined a reference heartbeat fluctuation amount 5102 and a reference heart rate as described later.

The reference heart rate and reference heartbeat fluctuation amount 5102 that are determined in this manner, are sent to the scanning speed selecting device 50. At the scanning speed selecting device 550, a scanning speed 5103 for optimizing an effective temporal resolution, described later, in the range of the reference heartbeat fluctuation amount 5102 and the reference heart rate is selected. The scanning speed 5103 that was selected in this manner is set in the scanning speed control device 520. The scanning speed control device 520 drives the rotational driving apparatus 506 at the scanning speed 5103 that was set.

Next, an entire execution algorithm according to this embodiment will be described using the flowchart in FIG. 34.

At the time of scanning, in step S3401, scanning parameters that are the conditions necessary for scanning are input from the input device 510 shown in FIG. 33.

In step S3402, heartbeat fluctuation information is acquired by, for example, attaching the heartbeat fluctuation measuring device 530 shown in FIG. 33 to the object. Further, heartbeat fluctuation information that was acquired in this manner is sent to the reference heartbeat fluctuation calculating device 540 as the actual heartbeat waveform 5101. In this case, based on the above described heartbeat fluctuation information, a reference heartbeat fluctuation amount 5102 and a reference heart rate are calculated as a range in which the heart rate may settle down. The scanning speed selecting device 550 receives the reference heartbeat fluctuation amount 5102 and reference heart rate that were calculated in this manner.

In step S3403, the scanning speed selecting device 550 performs preparations for deciding one scanning speed from among a plurality of scanning speeds at which the effective temporal resolution is optimized for within a heartbeat fluctuation width decided using the reference heart rate and the reference heartbeat fluctuation amount 5102. More specifically, it evaluates the effective temporal resolution. This evaluation is performed employing a lowest temporal resolution, mean temporal resolution and temporal resolution fluctuation width and the like, described later, as a measure.

In step S3404, the scanning speed selecting device 550 determines the optimized scanning speed 5103 based on the evaluation of the effective temporal resolution in the above described step S3403.

In step S3405, the scanning speed control device 520 causes scanning to be executed at the scanning speed 5103 determined in step S3404, and the X-ray detector 503 collects transmitted X-ray data as a set with heartbeat fluctuation information that was collected separately by the heartbeat fluctuation measuring device 530.

In step S3406, based on the reconstruction parameters that were input in step S3401, the image processor 508 performs ECG-gated reconstruction for the set of the heartbeat fluctuation information and transmitted X-ray data that was obtained in step S3405. In this connection, as used herein the term "ECG-gated reconstruction" refers to reconstruction that is performed with respect to a cardiac phase that is obtained from heartbeat fluctuation information while synchronizing with a predetermined temporal phase difference, and includes electrocardiogram half reconstruction and electrocardiogram segment reconstruction.

The reasons why, in the conventional technology, when the heartbeat of the object fluctuates and scanning is thus performed under a heart rate condition that is different to the initially assumed heart rate, the effective temporal resolution decreases and image quality deteriorates will now be clarified. The present embodiment clarifies this phenomenon and provides an answer to that problem.

First, the difference in the meaning of the terms "temporal resolution" and "effective temporal resolution" will be explained. The term "temporal resolution is high" refers to the fact that by scanning a moving subject in a shorter time, blurring of the moving subject accompanying the course of time can be lessened. In the conventional technology, as the scanning speed increases, i.e. the scan time is reduced, the temporal resolution increases. For example, in FIG. 35 the scanning speed of (a) is a 0.7 sec. scan, and the scanning speed of (b) is a 0.9 sec. scan. Accordingly, the scan of the smaller number of 0.7 sec. acquires images of the same area in a shorter time than the 0.9 sec. scan, and thus the temporal resolution for the 0.7 sec. scan is relatively higher.

Further, the scanning speeds in FIGS. 36(*a*) and (*b*) are a 0.5 sec. scan and a 1.1 sec. scan, respectively, and similarly the temporal resolution of the scan of the smaller number of 0.5 sec. is relatively higher than that of the 1.1 sec. scan. Therefore, when the scanning speeds in FIG. 35 and FIG. 36 are combined, it can be understood that the temporal resolution decreases in the order of the 0.5 sec. scan in FIG. 36(*a*), 0.7 sec. scan in FIG. 35(*a*), 0.9 sec. scan in FIG. 35(*b*), and 1.1 sec. scan in FIG. 36(*b*).

However, when we consider heart rate fluctuations the circumstances change. The effect on temporal resolution when heartbeat fluctuations are taken into account will be described using the concept "effective temporal resolution". The effective temporal resolution changes depending on the heart rate, and it becomes lower as the length of the longest among acquisition times of partial data that constitute a reconstruction image for each heart rate increases. However, it is not something that is uniquely fixed if the heart rate is determined, and it changes in accordance with part of various scanning parameters that can be arbitrarily set, such as the scanning speed (scan time), number of detector rows, the scan method such as a helical scan or circular scan, and the helical pitch.

FIG. 35 and FIG. 36 are diagrams that graph the relation between effective temporal resolution and heart rate [beat/min] for each scanning speed (scan time) with respect to the case of a helical scan at a helical pitch using a multi-row detector of a certain number of rows. In FIG. 35, for a case in which the heart rate of a certain subject fluctuates in a range between B and C around a center A, when the actual temporal resolution of the 0.7 sec. scan in FIG. 35(*a*) is compared with that of the 0.9 sec. scan in FIG. 35(*b*) when the heart rate is at position A, it is found that the temporal resolution at the time of the 0.7 sec. scan in FIG. 35(*a*) in which the rotating part makes one rotation in 0.7 sec. is slightly higher than that at the time of the 0.9 sec. scan in FIG. 35(*b*) in which the rotating part makes one rotation in 0.9 sec.

However, when the heart rate is at position B, the effective temporal resolution of the 0.9 sec. scan in FIG. 35(*b*) is higher than that at the time of the 0.7 sec. scan in FIG. 35(*a*). When the heart rate is at position C, conversely the effective temporal resolution of the 0.7 sec. scan in FIG. 35(*a*) is higher than that at the time of the 0.9 sec. scan in FIG. 35(*b*).

Figure 35A:
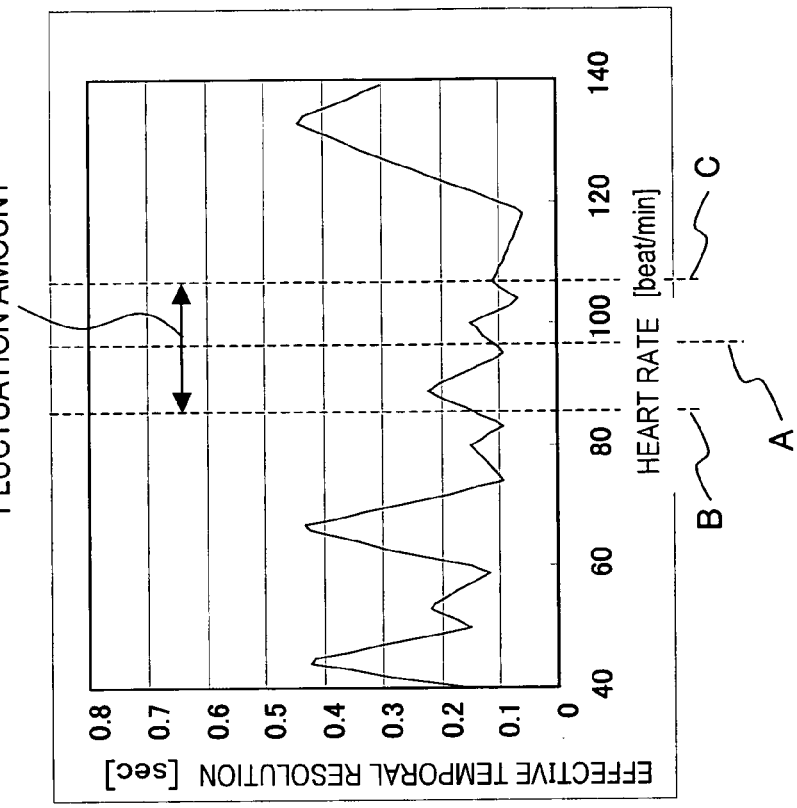
FIG. 35(a) is a graph describing one correlation between a heartbeat fluctuation width and effective temporal resolution with respect to two scanning speeds, that shows a view at the time of a 0.7 second scan (comparatively high temporal resolution), and (b) is a graph describing one correlation between a heartbeat fluctuation width and effective temporal resolution with respect to two scanning speeds, that shows a view at the time of a 0.9 second scan (comparatively low temporal resolution)
Figure 35B:
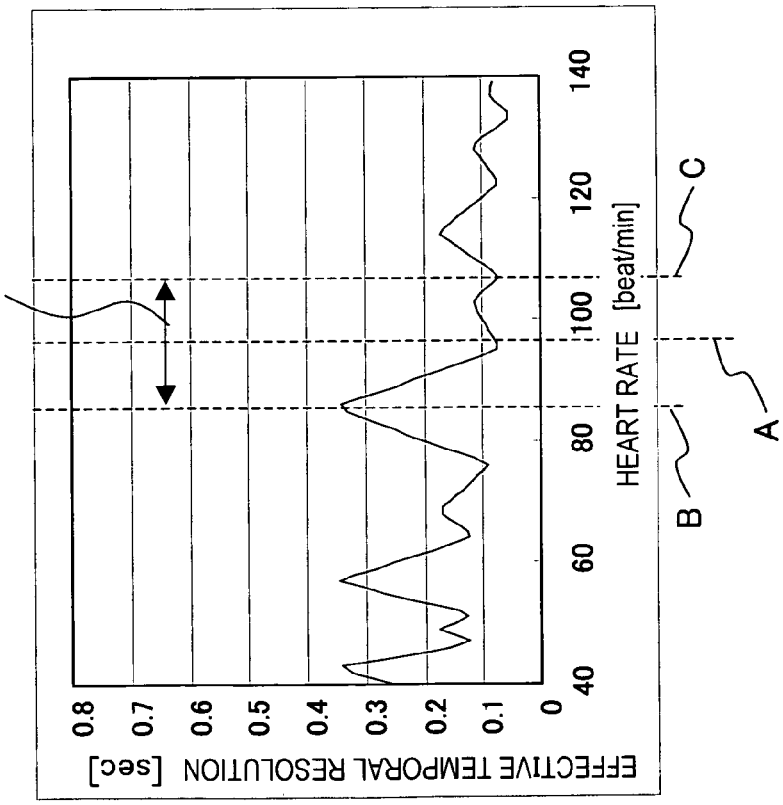

A more detailed description (i.e. a comparison in FIG. 35(a) and FIG. 35(b)) is as follows. When the heart rate is in a range from the vicinity of 85 to the vicinity of 90, the 0.9 sec. scan in FIG. 35(b) produces the highest effective temporal resolution. When the heart rate is between the vicinity of 90 and the vicinity of 95, the effective temporal resolution is approximately equal. When the heart rate is between the vicinity of 95 and the vicinity of 102 [beat/min], the 0.7 sec. scan in FIG. 35(a) produces the highest effective temporal resolution. When the heart rate is between the vicinity of 102 and the vicinity of 106 [beat/min], the 0.9 sec. scan in FIG. 35(a) produces the highest effective temporal resolution. When the heart rate is between the vicinity of 106 and the vicinity of 110 [beat/min], the 0.7 sec. scan in FIG. 35(a) produces the highest effective temporal resolution.

Likewise, referring to FIG. 36, the cases of a scan time of (a) 0.5 sec. and (b) 1.1 sec. will be compared. In FIG. 36, when the heart rate [beat/min] of an object to be examined is at a position A, the temporal resolution at the time of the 1.1 sec. scan as shown in (b) in which the rotating part makes one rotation in 1.1 sec. is higher than that at the time of the 0.5 sec. scan shown in (a). When the heart rate is at position B, there is no change in the effective temporal resolution between the 0.5 sec. scan of (a) and the 1.1 sec. scan of (b). When the heart rate is at position C, the effective temporal resolution at the time of the 0.5 sec. scan of (a) is higher than that at the time of the 1.1 sec. scan of (b). A more detailed description is as follows. When the heart rate is between the vicinity of 86 and the vicinity of 92 [beat/min], the 0.5 sec. scan shown in (a) produces the highest effective temporal resolution. When the heart rate is between the vicinity of 92 and the vicinity of 99 [beat/min], the 1.1 sec. scan shown in (b) produces the highest effective temporal resolution. When the heart rate is between the vicinity of 99 and the vicinity of 104 [beat/min], the 0.5 sec. scan shown in (a) produces the highest effective temporal resolution.

As described above, since the effective temporal resolution varies minutely according to the heart rate, the effective temporal resolution cannot be optimized without determining the scan time by taking into account such variations.

Next, differences between the effective temporal resolution and the temporal resolution will be described in detail. As described above, when reconstructing an ECG-gated image, a tomogram can not be obtained unless image data is collected from a view direction of at least 180°. However, since the heart is always moving, a period in which the heart is in a state in which it is hardly moving in a certain cardiac phase is extremely short. Scanning performed in one rotation is not sufficient to obtain a data set for at least 180° that is necessary for reconstruction by acquiring X-ray transmission data from a variety of view angle within that short time, and it is necessary to perform scanning over a number of rotations. In this case, X-ray transmission data corresponding to a certain cardiac phase that is obtained for each rotation is called a "segment".

Since corresponding target cardiac phases differ in accordance with the internal position in a segment obtained in this manner, a high weight is assigned to a position within a segment corresponding to the target cardiac phase, and a low weight is assigned to a position within a segment that is separate from the target cardiac phase. In this way, the temporal resolution of a reconstruction image can be further increased.

Figure 37A:
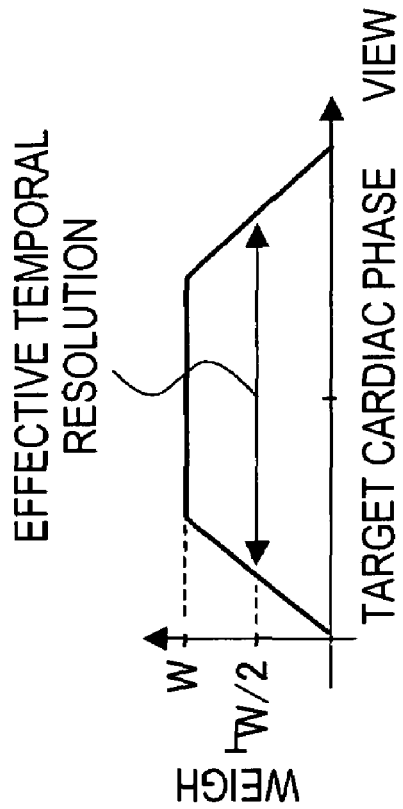
FIG. 37(a) is a view describing the relation between effective temporal resolution and weights according to segments, which shows the case of a rectangular weighting, and (b) is a view describing the relation between effective temporal resolution and weights according to segments, which shows the case of a trapezoidal weighting.
Figure 37B:
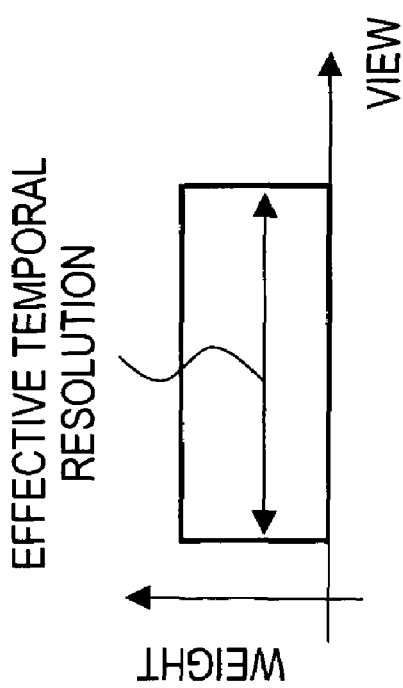

When assigning weights to a segment, as shown in FIG. 37(a), when the contribution ratio to image reconstruction is equal at each position within the segment, that is, when weights are assigned in the form of a rectangular weighting, a contributing time width is a value obtained by converting the segment width to time. However, as shown in FIG. 37(b), when the contribution ratio is different at each position of a segment, for example, when weights are assigned in the form of trapezoidal weighting, a contributing time width is about a half-value width of a weight function that is added to the segment. Thus, in FIG. 37(a) and FIG. 37(b), the phenomenon that the effective temporal resolution differs between segment occurs. More specifically, the widths of weights used in reconstruction of a given tomogram do not necessarily match. As a result, when reconstructing a tomogram, the temporal resolution is decided by the effective temporal resolution that is the worst in the segment is, i.e. the temporal resolution is decided by allowing for the width of the widest weight. In this connection, segments will sometimes overlap partially, or alternatively, in some cases when it is not possible to obtain a segment of a target view angle of a target cross-section in a target cardiac phase, the segment will be determined by interpolation based on adjacent segments, and therefore weighting for each segment becomes all the more complicated and further affects the effective temporal resolution in a complex manner. The foregoing described that the effective temporal resolution is representative of the segment that contributes most to a decrease in image quality caused by motion in an image of a moving body such as the heart.

Next the meaning of the terms "reference heart rate" and "reference heartbeat fluctuation amount" will be clarified with reference to FIG. 33 and FIG. 38. The reference heartbeat fluctuation calculating device 540 acquires an actual heartbeat waveform in advance from an object to be examined, and based thereon determines a reference heart rate and a reference heartbeat fluctuation amount when deciding scanning parameters before scanning. The actual heartbeat waveform is, for example, a waveform as shown in FIG. 38(a), and it changes over the course of time. In brief, the reference heart rate and reference heartbeat fluctuation amount are an averaged heart rate that is obtained from the actual heartbeat waveform and the fluctuation width thereof, and methods for determining these can be broadly classified into two methods. One is a method that directly analyzes the actual heartbeat waveform to determine the mean value and fluctuation amount thereof, and the other is a method that makes a histogram of the actual heartbeat waveform and performs analysis thereof. These methods are described in detail later.

Next, an algorithm according to this embodiment of the present invention will be described in detail referring to FIG. 34. This algorithm can be implemented by the reference heartbeat fluctuation calculating device 540 and the scanning speed selecting device 550 shown in FIG. 33, and implementation is not limited to these, and it can also be implemented by running a program that executes the aforementioned algorithm inside the central control unit 507.

In step S3401, scanning parameters are input from the input device 510. The scanning parameters include the scan time as the scanning speed necessary for collecting data required for scanning of one slice, the position and range of the region of interest, selection of a scan method such as a helical scan or circular scan, the helical pitch and table movement speed and the like. Further, the reconstruction parameters include the position and range of the region of interest, the helical pitch, the reconstruction image size, the table movement speed, the cardiac phase to be reconstructed, the reconstruction mode such as half reconstruction or segment reconstruction, the segment width index, the reconstruction slice spacing and the reconstruction filter function. At this time, scanning parameters including the table movement speed or helical pitch may be input via the input device 510.

As the input device 510, a mouse, a keyboard, a touch panel display or an audio input device (microphone) can be used. In step S3402, the reference heart rate or reference heartbeat fluctuation amount 5102 is acquired under the various conditions. Step S3402 is executed by, for example, the heartbeat fluctuation measuring device 530 and the reference heartbeat fluctuation calculating device 540 shown in FIG. 33. In this example, the heartbeat fluctuation measuring device 530 is, for example, an electrocardiograph. Naturally, instead of that, it is possible to use dynamic information that was obtained from measurement data 5104 acquired with the X-ray CT apparatus as shown in FIG. 33 in place of an electrocardiographic waveform. In that case, a superfluous device such as an electrocardiograph can be omitted. For example, a known technique such as a technique disclosed in Japanese Patent Laid-Open No. 2003-204961 can be used to use dynamic information obtained from measurement data in place of an electrocardiographic waveform. Further, it is also possible to use technology that is capable of ascertaining dynamic information based on technology disclosed in Japanese Patent Laid-Open No. 2004-313513 or other technology for capturing image data.

The heart rate or heartbeat fluctuation amount at the time of scanning will differ for each object. Further, a heartbeat fluctuation amount or heart rate that can be read from the slope of an electrocardiographic waveform in breath-holding practice prior to scanning will also differ for each object. Therefore, in determining the reference heart rate and the reference heartbeat fluctuation amount 5102, as described above, the chronological actual heartbeat waveform 5101 of the object is acquired. Since the actual heartbeat waveform to be used in that of a finite duration, hereunder it is referred to as a "heartbeat fluctuation function". The heartbeat fluctuation function and a histogram thereof are prepared according to the two methods described above.

The heartbeat fluctuation function illustrates the correlation between elapsed time and heart rate, and the histogram illustrates the correlation between heart rate and frequency as the occurrence frequency for each heart rate. In step S3402, the reference heartbeat fluctuation calculating device 540 refers to a heartbeat fluctuation function or a histogram that was created in this manner, and determines the reference heart rate [beat/sec] as one of the items (1) to (5) shown below, and the reference heartbeat fluctuation amount as one of the items (6) to (10) shown below.

(1) A mean value of the heartbeat fluctuation function is taken as the reference heart rate.

(2) A center of gravity value of the histogram is taken as the reference heart rate.

(3) A median value of the histogram is taken as the reference heart rate.

(4) An additional value that is weighted in accordance with the frequency of the histogram is taken as the reference heart rate.

(5) A center of gravity value at which the frequency of the histogram is Th or more is taken as the reference heart rate.

(6) The fluctuation width (difference between highest heart rate and lowest heart rate) of the heartbeat fluctuation function is taken as the heartbeat fluctuation amount.

(7) The width of the histogram (difference between highest heart rate and lowest heart rate) is taken as the heartbeat fluctuation amount.

(8) The half-value width of the histogram is taken as the reference heartbeat fluctuation width.

(9) A width of 1/10 of the histogram is taken as the reference heartbeat fluctuation width.

(10) A width (difference between highest heart rate and lowest heart rate) at which the frequency of the histogram is Th or more is taken as the reference heartbeat fluctuation width.

Figure 38A:
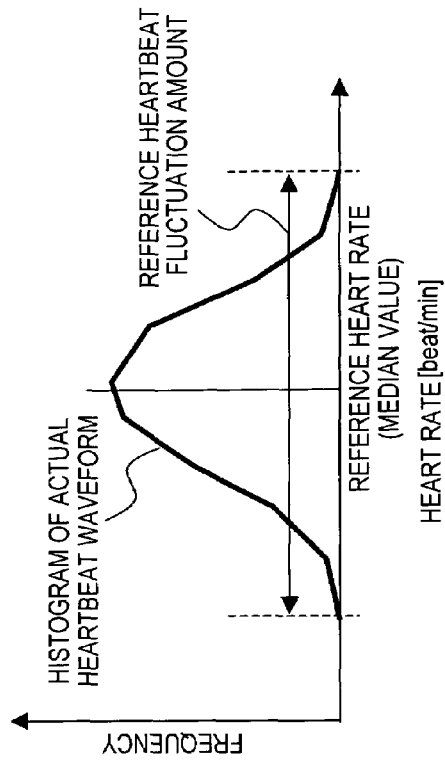
FIG. 38(a) is a view that illustrates a method of determining a reference heartbeat fluctuation width and a reference heart rate according to the fifth embodiment, which shows an actual heartbeat waveform, (b) is a view that illustrates a method of determining a reference heartbeat fluctuation width and a reference heart rate according to the fifth embodiment, which shows a histogram of an actual heartbeat waveform, (c) is a view that illustrates a method of determining a reference heartbeat fluctuation width and a reference heart rate according to the fifth embodiment, which shows a reference heartbeat fluctuation amount (half-value width), and (d) is a view that illustrates a method of determining a reference heartbeat fluctuation width and a reference heart rate according to the fifth embodiment, which shows a reference heartbeat fluctuation amount.
Figure 38B:
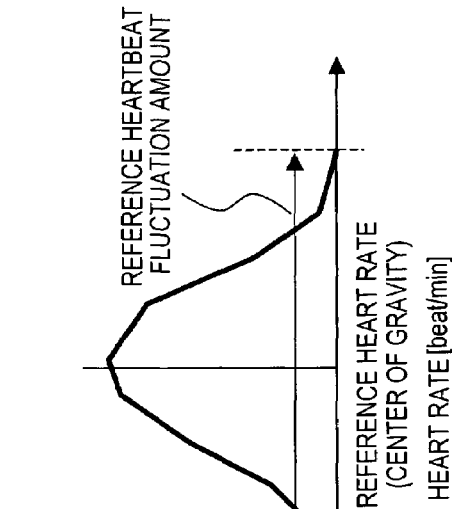
Figure 38C:
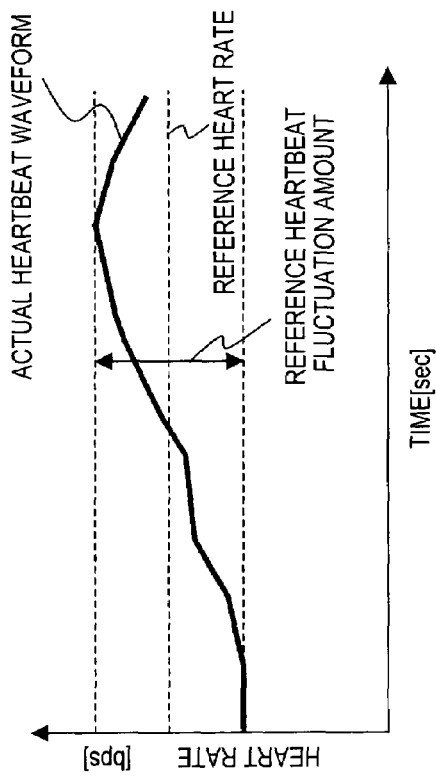
Figure 38D:
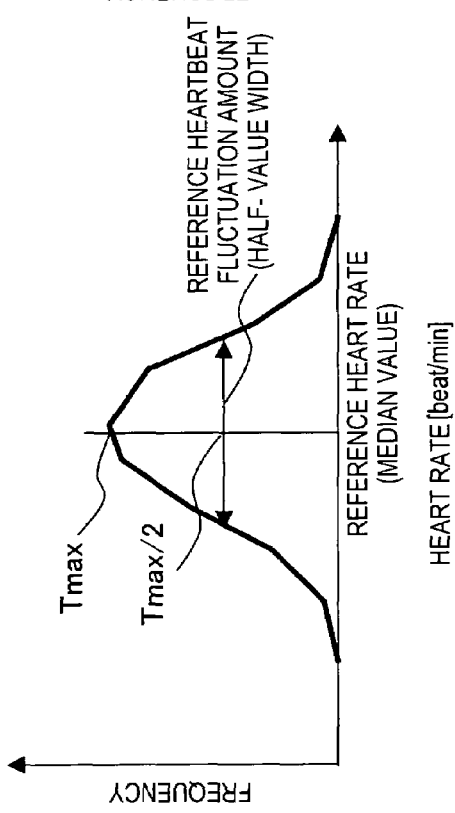

FIGS. 38(a) to (d) illustrate examples of the aforementioned combinations. In FIG. 38(a), a heartbeat fluctuation function is created from the actual monitoring results of an object to be examined, and the mean value thereof is determined as the reference heart rate as in (1) above, and the fluctuation width thereof is determined as the reference heartbeat fluctuation amount as in (6) above. In FIG. 38(b), a histogram is created that illustrates the correlation between a heart rate obtained from the actual monitoring results of an object to be examined and a frequency as the occurrence frequency thereof, and the center of gravity value thereof is determined as the reference heart rate as in (2) above, and the width thereof is determined as the reference heartbeat fluctuation amount as in (7) above. In FIG. 38(c), a histogram is created that illustrates the correlation between a heart rate obtained from the actual monitoring results of an object to be examined and a frequency as the occurrence frequency thereof, and the center of gravity value thereof is determined as the reference heart rate as in (2) above, and the half-value width is determined as the reference heartbeat fluctuation amount as in (8) above. In FIG. 38(d), a histogram is created that illustrates the correlation between a heart rate obtained from the actual monitoring results of an object to be examined and a frequency as the occurrence frequency thereof, and the median value thereof is determined as the reference heart rate as in (3) above, and the width thereof is determined as the reference heartbeat fluctuation amount as in (7) above. In this connection, the heart rate or heartbeat fluctuation amount at the time of previous scanning will differ for each object. Further, irrespective of who the object is, a statistical heartbeat fluctuation amount at a time of filling with a contrast medium can be used. Further, if data that relates to the heart rate or heartbeat fluctuation amount at the time of filling with a contrast medium in the past still remains for the object, that kind of data can be used. When using this kind of statistical data or past data, the data can be input via the input device 510 shown in FIG. 33, or can be read into the central control unit 507 from separately connected storage device. These are sent to the reference heartbeat fluctuation amount calculating device 540 via a line 5104 or 5105 shown in FIG. 33. Based on heartbeat information under these various conditions, a reference heart rate and a reference heartbeat fluctuation amount 5102 is determined that is suitable to that object at that examination time.

An example of using the lowest temporal resolution that may have the most application opportunities among the choices at step S3403 in FIG. 34 will be described according to the present embodiment. As an additional remark in advance, the aforementioned choices also include the temporal resolution fluctuation width and the mean temporal resolution, in addition to the above described lowest temporal resolution. The lowest temporal resolution is suited to a case where the heart rate changes gradually and the like. The temporal resolution fluctuation width is suited to a case of a person with a higher heartbeat than normal who is liable to become nervous and the like. The mean temporal resolution is suited to a case where there is a sudden fluctuation in a pulse wave.

Figure 39A:
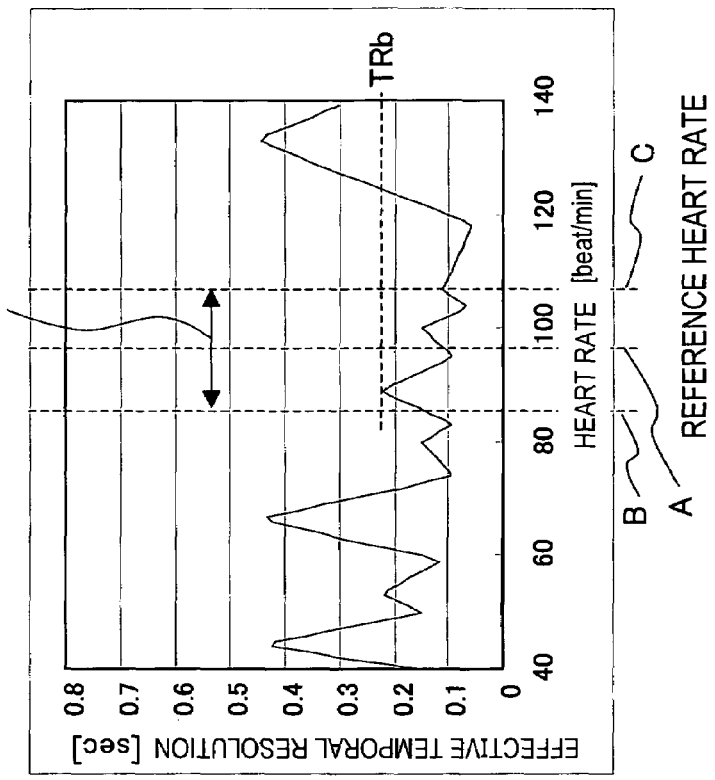
FIG. 39(a) is a view showing a method of determining a scan time that used a lowest temporal resolution according to the fifth embodiment, that illustrates a case using the lowest temporal resolution (time of 0.7 seconds scan), and (b) is a view showing a method of determining a scan time that used a lowest temporal resolution according to the fifth embodiment, that illustrates a case using the lowest temporal resolution (time of 0.9 seconds scan)
Figure 39B:
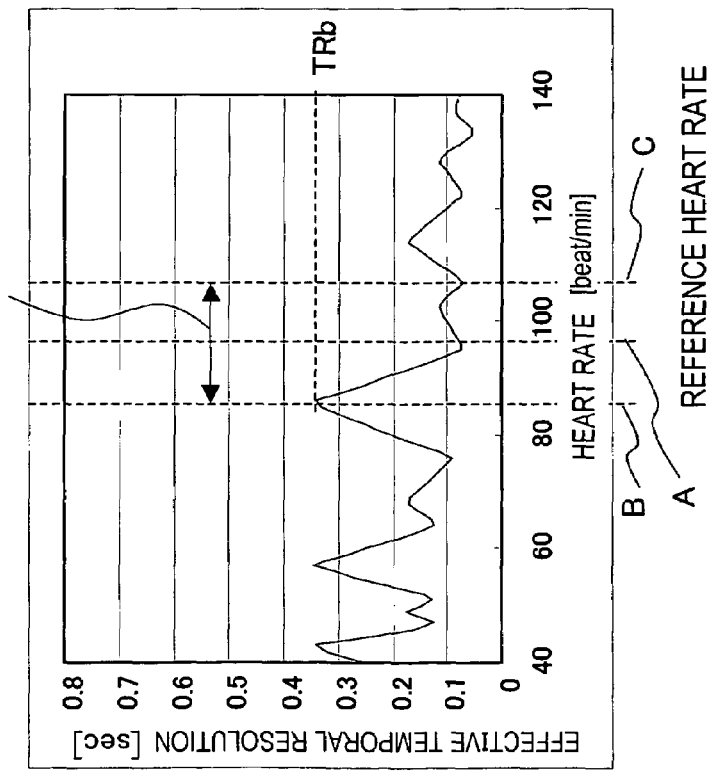

Steps S3403 and S3404 are, for example, executed by the scanning speed selecting device 550 shown in FIG. 33. When the correlation with effective temporal resolution corresponding to changes in heart rate are graphed for a plurality of scan times, sequential lines as shown in FIG. 39 are obtained, as was already partially described. Although graph have been prepared with respect to only (a) a scan time of 0.7 seconds and (b) a scan time of 0.9 seconds in FIG. 39, it is preferable to previously prepare a graph that shows the correlation between heartbeat and effective temporal resolution that was made to correspond to various scanning parameters such as a plurality of scan times that number three or more. FIG. 39 shows a method of calculating lowest temporal resolution, and by applying the reference heart rate and the reference heartbeat fluctuation amount 3102 that were determined in step S3402 to this correlation, a lowest temporal resolution TRb that is based on the reference heart rate and reference heartbeat fluctuation amount can be obtained.

In step S3404, the lowest temporal resolution TRb that was determined as described above is compared with respect to a scan time of 0.7 seconds and a scan time of 0.9 seconds. The lowest effective temporal resolutions TRb between the reference heartbeat fluctuation amounts B and C that are established around the reference heart rate A are compared, and the scan time for which the lowest effective temporal resolution is higher is decided as the scan time at the time of scanning.

More specifically, in the case of the scan time of 0.7 [sec/rot] in FIG. 39(*a*), when the heart rate is approximately 85 [beat/min] the lowest temporal resolution TRb (0.7)=0.35 [sec], and in the case of the scan time of 0.9 [sec/rot] in FIG. 39(*b*), when the heart rate is approximately 85 [beat/min] the lowest temporal resolution TRb (0.9)=0.23 [sec]. That is, since TRb (0.7)>TRb (0.9), the scan time with the higher lowest temporal resolution is 0.9 [sec/rot]. Therefore, the scan time of 0.9 [sec/rot] is set as a scanning parameter.

In step S3405, for the scan time that was determined in step S3404, a helical scan is executed based on the helical pitch that is a scanning parameter input in step S3401. At this time, scanning is carried out while associating the scanning view position and position of the electrocardiographic waveform.

In step S3406, the image data obtained in step S3405 is subjected to ECG-gated reconstruction based on reconstruction parameters that were input in step S3401. As used herein, the term "ECG-gated reconstruction" refers to image reconstruction performed by extracting data corresponding to a target cardiac phase from X-ray transmission data that is shifted and synchronized so as to be a predetermined scan time with respect to a heartbeat period obtained from an electrocardiogram, and it includes electrocardiogram half reconstruction and electrocardiogram segment reconstruction.

As described above, according to this embodiment it is possible to determine a scan time as a scanning speed that can optimize effective temporal resolution. When using a lowest temporal resolution as in the present embodiment, it is possible to employ an effective temporal resolution that is even a little higher as the effective temporal resolution contributing most to image quality degradation within a heartbeat fluctuation width. This method of using a lowest temporal resolution is suited, for example, to a case in which a heart rate gradually changes. More specifically, it is suited to a case in which the pulse of an object to be examined increases due to nervousness or a case in which a contrast medium was administered. In other words, it is suited to general subjects with a narrow heartbeat fluctuation width.

Figure 40A:
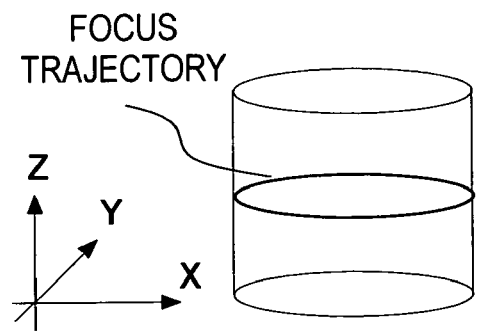
FIG. 40(a) is a conceptual diagram illustrating a helical scan and a circular scan in an X-ray CT apparatus, which illustrates a focus trajectory of a circular scan, and (b) is a conceptual diagram illustrating a helical scan and a circular scan in an X-ray CT apparatus, which illustrates a focus trajectory of a helical scan.
Figure 40B:
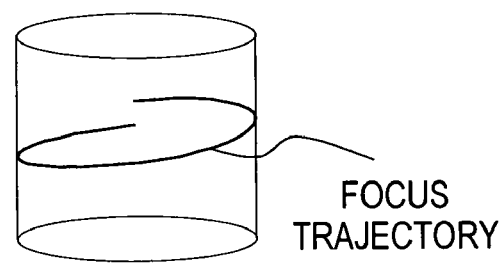

In the foregoing, this embodiment was described taking an example of performing a helical scan using a multi-row detector. However, this embodiment is not limited to a helical scan, and it can be applied in a similar manner to the case of a circular scan. Next, a description is given regarding the fact that the present invention can be applied to either scan method. FIG. 40 is a view that compares the focus trajectory for a circular scan and a helical scan according to the present invention. FIG. 40(*a*) shows the movement trajectory of the X-ray source at the time of a circular scan, and FIG. 40(*b*) shows the movement trajectory of the X-ray source at the time of a helical scan. In the case of scanning performed with a circular orbit as shown in FIG. 40(*a*), by performing filtered two-dimensional back projection, an image at an X-ray source position can be accurately reproduced.

However, in the case of scanning performed with a helical trajectory as shown in FIG. 40(*b*), since the trajectory moves in the body axis direction the focus trajectory does not form a closed curve and thus data is discontinuous at the scanning end positions. That is, a reconstruction image or X-ray transmission data to be handled discretely is handled as continuous data. Therefore, by only performing filtered two-dimensional back projection, streak shaped artifact are generated because the data ends used in reconstruction are discontinuous in the body axis direction. Thus, data interpolation or the like is conducted for data obtained with a helical trajectory as shown in FIG. 40(*b*). It is thereby possible to create circular orbit data as shown in FIG. 40(*a*). Thereafter, streak artifacts can be prevented by performing filtered two-dimensional back projection.

By using interpolation in this manner, it is possible to obtain an image in which discontinuity was lessened. When actually performing this kind of interpolation, discrete calculations can be performed by interpolation in three directions consisting of the phase direction, detector row direction and detector channel direction using an interpolation method such as Lagrange interpolation. Preferably, calculation is performed by interpolation in four directions that include interpolation in the time direction.

As described above, it is possible to obtain data of a predetermined cardiac phase from a variety of view angles in an arbitrary tomographic plane in similar manner for a helical scan and a circular scan. Heartbeat fluctuation information can then be collected independently of the scan method, such as a circular scan or a helical scan.

Further, although a case that used a multi-row detector was described according to the present embodiment, the present invention is also applicable to a case of using a single-row detector. FIG. 41 shows conceptual diagrams in which a single-row detector and a multi-row detector are arranged in the direction of the circulation axis. With respect to the multi-row detector shown in FIG. 41(*b*), although the thickness of an X-ray beam for each row (hereunder, referred to as "detector collimation thickness") is thinner than that of the single-row detector shown in FIG. 41(*a*), the configuration is one in which a plurality of single-row detectors of narrow width are aligned in the direction of the circulation axis, and as a whole that includes a plurality of rows it can image a wider area in the direction of the circulation axis at one time.

When a helical scan as shown in FIG. 41(*b*) was performed using a multi-row detector, for example, it is possible to control scanning such that after the first row of the detector collected X-ray transmission data from a certain view angle for a tomographic plane, the second row collects X-ray transmission data from a certain view angle for the same tomographic plane, and collection of data from a certain view angle for that tomographic plane is then continued in a similar manner for the third row to nth row. Generally, when a helical scan is carried out with a multi-row detector, scan control can be performed so that different detector rows on the detector respectively detect transmission X rays of a certain predetermined tomographic plane from their respective view angles.

Figure 41A:
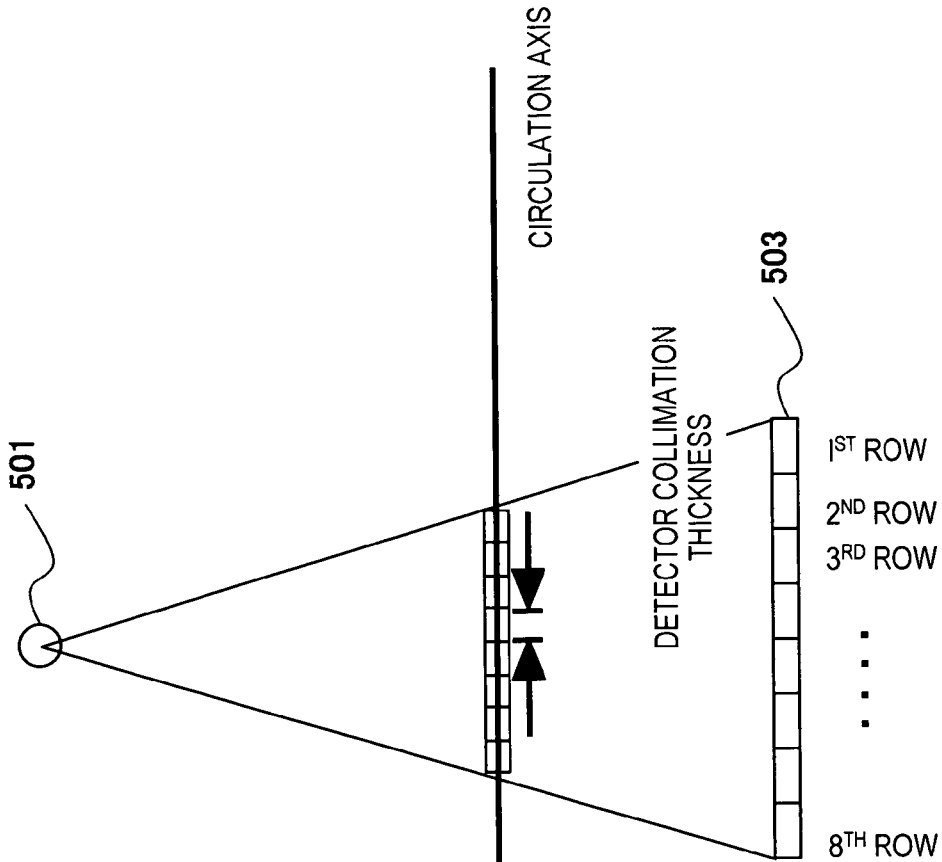
FIG. 41(a) is a conceptual diagram illustrating a detector collimation thickness on a circulation axis for a single-row X-ray detector and a multi-row X-ray detector in an X-ray CT apparatus, that shows a detector collimation thickness of a single-row X-ray detector, and (b) is a conceptual diagram illustrating a detector collimation thickness on a circulation axis for a single-row X-ray detector and a multi-row X-ray detector in an X-ray CT apparatus, that shows a detector collimation thickness of a multi-row X-ray detector.
Figure 41B:
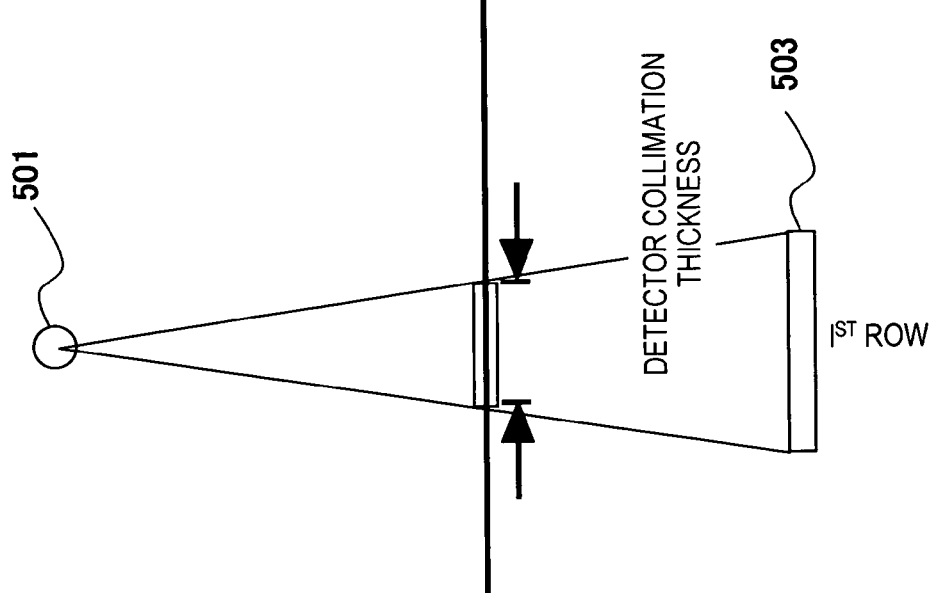

At this time, by using the aforementioned interpolation, it is possible to ultimately obtain that same effect as detecting transmission X rays from various view angles by using the circular scan in FIG. 41(a).

For this embodiment, by performing a helical scan using the multi-row detector as described above it is possible to acquire a plurality of cross-sections for a segment of a predetermined cardiac phase from many view directions at one time. However, even when a circular scan is performed using the multi-row detector as described above it is still possible to obtain a plurality of cross-sections for a segment of a predetermined cardiac phase from many view directions. Further, by repeating a helical scan using the above described single-row detector it is possible to acquire a plurality of cross-sections for a segment of a predetermined cardiac phase from many view directions, although it will require a certain amount of time. Furthermore, by performing a circular scan using the above described single-row detector it is also possible to acquire a certain cross section for a segment of a predetermined cardiac phase from many view directions, although it will require a certain amount of time.

As described above, even when a helical scan or circular scan and a multi-row detector or single-row detector are combined, the present invention can be implemented in accordance with the description of this embodiment.

In this connection, when using a multi-row detector, the spatial resolution in the direction of the circulation axis, i.e. the resolution in the body axis direction, of a tomogram depends greatly on the X-ray beam thickness (detector collimation thickness) per row. More specifically, the thinner that the detector collimation thickness is, the more the body axis resolution is enhanced. Therefore, when using a multi-row detector, the spatial resolution can also be enhanced in addition to enhancing the temporal resolution.

According to this embodiment, since scanning speed selecting device is provided that selects a scanning speed based on a heartbeat fluctuation amount and a heart rate that are measured with heartbeat fluctuation measuring device, even when scanning an object to be examined for whom there is a tendency for the heart rate at the time of actual scanning to differ from that when setting the scanning conditions, it is possible to select a scanning speed that can optimize the temporal resolution in accordance with the heart rate fluctuation tendency. Thus, an improvement in temporal resolution that is one factor that determines the quality of an image can be attempted.

It is therefore possible to avoid examination discrepancies caused by a deterioration in temporal resolution, and consequently the time and labour involved in reattempting scanning can be eliminated, improved examination efficiency can be realized, and ineffective radiation exposure that accompanies scanning reattempts can be avoided.

Further, since a reference heart rate and a reference heartbeat fluctuation amount can be determined from a measured heart rate and heartbeat fluctuation amount and the like, and the scanning speed selecting device can select a scanning speed on the basis of these, it is possible to ascertain the correlation with respect to scanning speed between the reference heart rate and reference heartbeat fluctuation amount and the effective temporal resolution, to thereby rationally enhance temporal resolution. Accompanying this, the opportunities for occurrence of examination discrepancies due to temporal resolution deterioration can be decreased still more. It is also possible to realize still further improvement regarding the time and labour involved in reattempting scanning, examination efficiency and avoidance of ineffective radiation exposure.

Since the reference heart rate is determined as a mean value of a measured heartbeat fluctuation amount and heart rate, or any one of a center of gravity value, median value and weighted additional value obtained when at least one part thereof is histogrammed, determination of a reference heart rate is simplified and selection of an optimal scanning speed can be performed swiftly and accurately.

Since the reference heartbeat fluctuation amount is determined as the calculated reference heart rate or fluctuation width, or any one of a width, half-value width or $\frac{1}{10}$ width when at least one part thereof was histogrammed, determination of a reference heartbeat fluctuation amount is simplified and selection of an optimal scanning speed can be performed swiftly and accurately.

Furthermore, using a correlation between effective temporal resolution and heart rate as determined for each scanning speed, heart rates within the range of a reference heartbeat fluctuation amount are applied to the correlation function for each different scanning speed to calculate and evaluate the effective temporal resolution, and therefore a relation with respect to scanning speed between the reference heart rate and reference heartbeat fluctuation amount and the effective temporal resolution is quantifiable, and thus improvement of temporal resolution can be attempted with greater accuracy. Accompanying this, the opportunities for occurrence of examination discrepancies due to temporal resolution deterioration can be decreased still more. It is also possible to realize still further improvement regarding the time and labour involved in reattempting scanning, examination efficiency, and avoidance of ineffective radiation exposure.

The lowest among a series of effective temporal resolutions obtained by application of the correlation function is taken as the lowest temporal resolution to select a scanning speed at which that lowest temporal resolution is highest, and this it is possible to set a scanning speed that can better enhance the temporal resolution in a case in which an object's pulse rises due to nervousness or a case where a contrast medium is administered.

Since the heartbeat fluctuation measuring device is movement amount extracting device that determines a movement amount of a moving body based of an electrocardiograph or the detected radiation, in a case where a heart rate and the fluctuation amount thereof can be estimated from data acquired with the X-ray CT apparatus, by using that function, even when there is no electrocardiograph it is possible to acquire a superior image with high temporal resolution.

Further, by comprising an input device that enables external input of data regarding a change in a heart rate or heartbeat fluctuation amount that serve as the basis for calculating the reference heart rate and the reference heartbeat fluctuation amount, it is possible to input from outside changes in a statistical heart rate after infusion of a contrast medium or the like or past heart rate fluctuation data of the same object, and to employ such information as a reference for determining a scanning speed. Even without estimating a heart rate and a fluctuation amount thereof from data obtained with an X-ray CT apparatus or other heartbeat fluctuation measuring device such as an electrocardiograph, it is possible to acquire a superior image with a high temporal resolution.

By comprising moving device that can move a relative location with respect to radiation detection device in the direction of the body axis of the object at the time of scanning, it is possible to acquire a cardiac image along the body axis direction of the object, and it is thus possible to improve the image quality of a four-dimensional image, a three-dimensional image in an arbitrary cardiac phase, or a two-dimensional image in an arbitrary cardiac phase and arbitrary cross-section.

Although a tomographic apparatus that uses X rays is used according to this embodiment, this embodiment is not limited thereto, and it can also be applied to a tomographic apparatus that uses gamma rays, neutron rays, positrons, electromagnetic energy or light.

SIXTH EMBODIMENT

Figure 34:
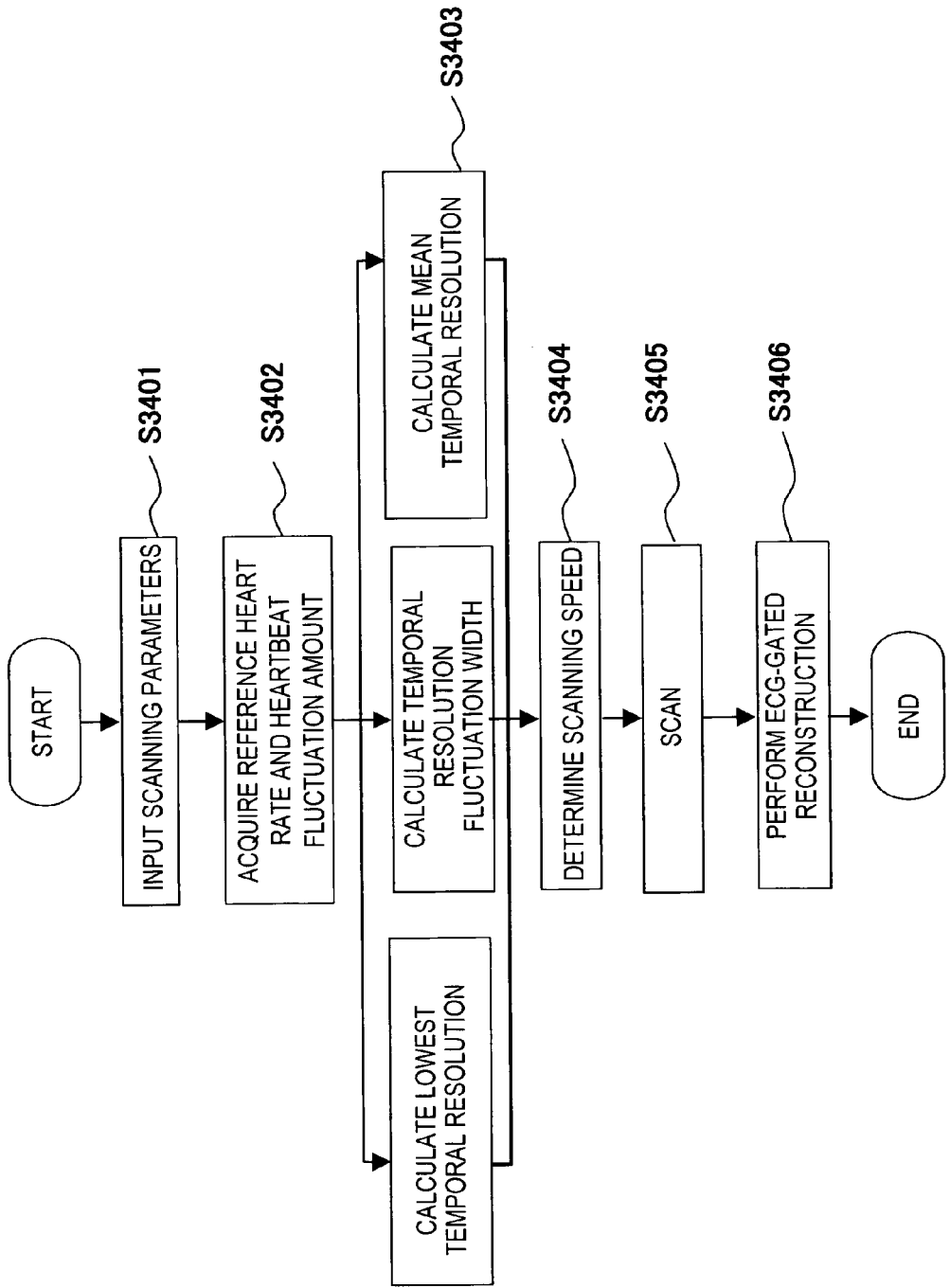
FIG. 34 is a flowchart illustrating the procedures of electrocardiogram (hereunder, referred to as "ECG")-gated reconstruction in the X-ray CT apparatus according to the fifth embodiment.

The sixth embodiment is a method of determining a scan time on the basis of a reference heartbeat fluctuation amount and a reference heart rate of an object to be examined in accordance with the flowchart shown in FIG. 34, as with the fifth embodiment. However, in the sixth embodiment, a temporal resolution fluctuation width that is calculated in step S3403 in FIG. 34 is different to the lowest temporal resolution of Embodiment 5. The other steps and components of the apparatus are the same as those described in the fifth embodiment, and a description thereof is omitted here. In this connection, unless specifically stated otherwise, in this embodiment the reference numbers that are the same as those in the fifth embodiment denote the same parts.

Figure 42A:
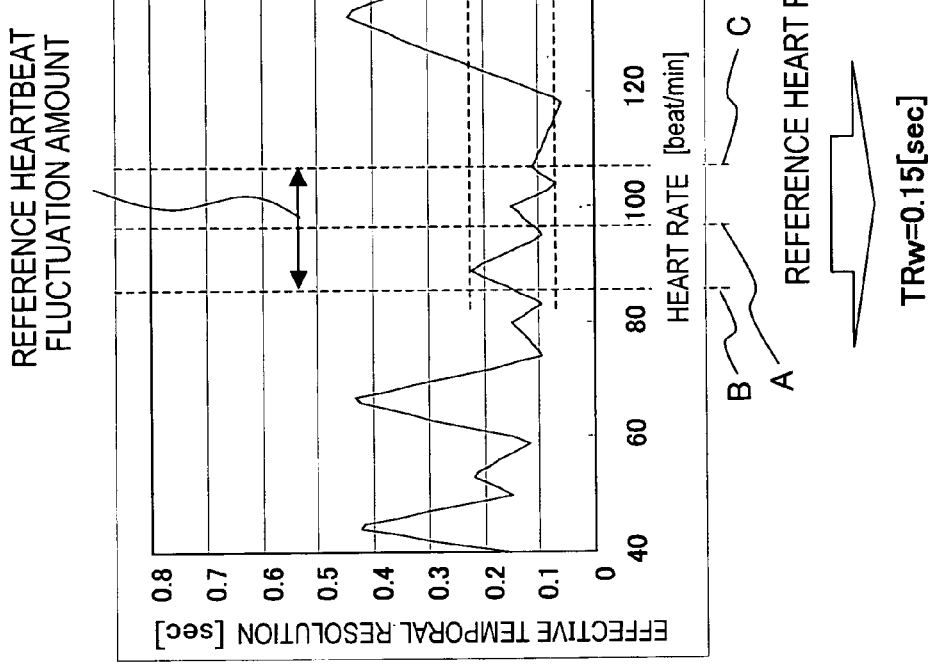
FIG. 42(a) is a view that illustrates a method of determining a scan time that used a temporal resolution fluctuation width according to the sixth embodiment, showing a case using the temporal resolution fluctuation width (time of 0.7 seconds scan), and (b) is a view that illustrates a method of determining a scan time that used a temporal resolution fluctuation width according to the sixth embodiment, showing a case using the temporal resolution fluctuation width (time of 0.9 seconds scan)
Figure 42B:
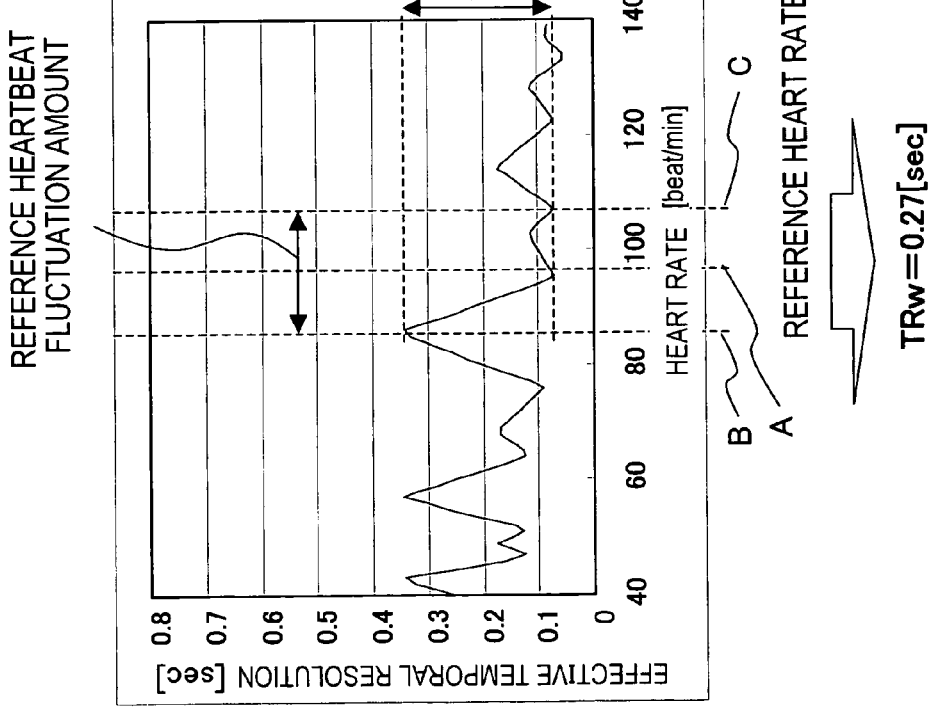

When using a temporal resolution fluctuation width, a correlation function as shown in FIG. 42 is used. A correlation function is preferably prepared in advance for each scan time in accordance with the combination of scanning parameters.

In step S3403 in FIG. 34, the temporal resolution fluctuation width is determined as shown in FIG. 42. The reason for using a temporal resolution fluctuation width TRw that determines a fluctuation width TRw of the effective temporal resolution in an area that is decided on the basis of a reference heartbeat range 5102 and a reference heart rate that were determined in step S3402 is that, if there is a large difference in the effective temporal resolution of a plurality of segments that are the basis of a reconstruction image of the same cross section, it is possible to prevent that difference being manifested as an artifact. The ultimate target object for an X-ray CT apparatus is an image. If there is a significant difference in the effective temporal resolution of segments at the time of image reconstruction, the image quality will be affected. More specifically, if one segment has an exceptionally high effective temporal resolution but the effective temporal resolution of the other segments is not at the same level as the high resolution, the temporal resolution is weighed down by the segments that have the low effective temporal resolution.

Therefore, in step S3404, the fluctuation in the effective temporal resolution within the reference heartbeat fluctuation width, i.e. the temporal resolution fluctuation width TRw, that is narrower is employed as the scan time. Step S3404 will be described referring to FIG. 42. First, temporal resolution fluctuation widths TRw corresponding to the ranges of reference heartbeat fluctuation amounts B and C that are established around a reference heart rate A are determined. For example, in FIG. 42(a), the fluctuation range of the effective temporal resolution for the reference heartbeat range is 0.08 to 0.35 [sec], and the temporal resolution fluctuation width TRw (0.7) is 0.27 [sec] in this time interval. Further, in FIG. 42(b), the fluctuation range of the effective temporal resolution for the reference heartbeat fluctuation amount is 0.08 to 0.23 [sec], and the temporal resolution fluctuation range TRw (0.9) is 0.15 [sec]. More specifically, when the scan time is 0.7 [sec/rot], the temporal resolution fluctuation width TRw (0.7) =0.27 [sec], and when the scan time is 0.9 [sec/rot], the temporal resolution fluctuation width TRw (0.9)=0.15 [sec].

Next, it is determined which temporal resolution fluctuation width is narrower. In this example, since TRw (0.7) >TRw (0.9), the scan time with the narrower temporal resolution fluctuation width is 0.9 [sec/rot]. Accordingly, the scan time 0.9 [sec/rot] is set as a scanning parameter.

In step S3404, either the temporal resolution width or the lowest temporal resolution calculated in step S3403, or a scan time that is a scanning speed based on a combination of these may be selected.

According to this embodiment, since a scanning speed at which a fluctuation width of an effective temporal resolution within a reference heartbeat range centering on a reference heart rate is narrowest is selected, the effective temporal resolution and homogenization of an image are excellent.

For example, the present embodiment is suited to a case in which a heart rate is distributed uniformly over a wide range, or to an object to be examined who is liable to become tense or who is in a state of severe tension and has heartbeat fluctuations that are greater than normal, or to an object to be examined with a particularly weak heart.

The present embodiment is more suitable for a case in which an object to be examined has large heartbeat fluctuations than the case of the lowest resolution of the fifth embodiment.

Although a tomographic apparatus that uses X rays is used according to this embodiment, the present embodiment is not limited thereto, and it can also be applied to a tomographic apparatus that uses gamma rays, neutron rays, positrons, electromagnetic energy or light.

SEVENTH EMBODIMENT

The seventh embodiment differs to the fifth embodiment and sixth embodiment in the respect that, at step S3403 in FIG. 34 the mean temporal resolution is calculated instead of the lowest temporal resolution and the temporal resolution fluctuation width as in the fifth and sixth embodiments, respectively. The other steps and components of the apparatus are the same as those described in the fifth embodiment, and a description thereof is omitted here. In this connection, unless specifically stated otherwise, in this embodiment the reference numbers that are the same as those in the fifth embodiment denote the same parts.

Figure 43A:
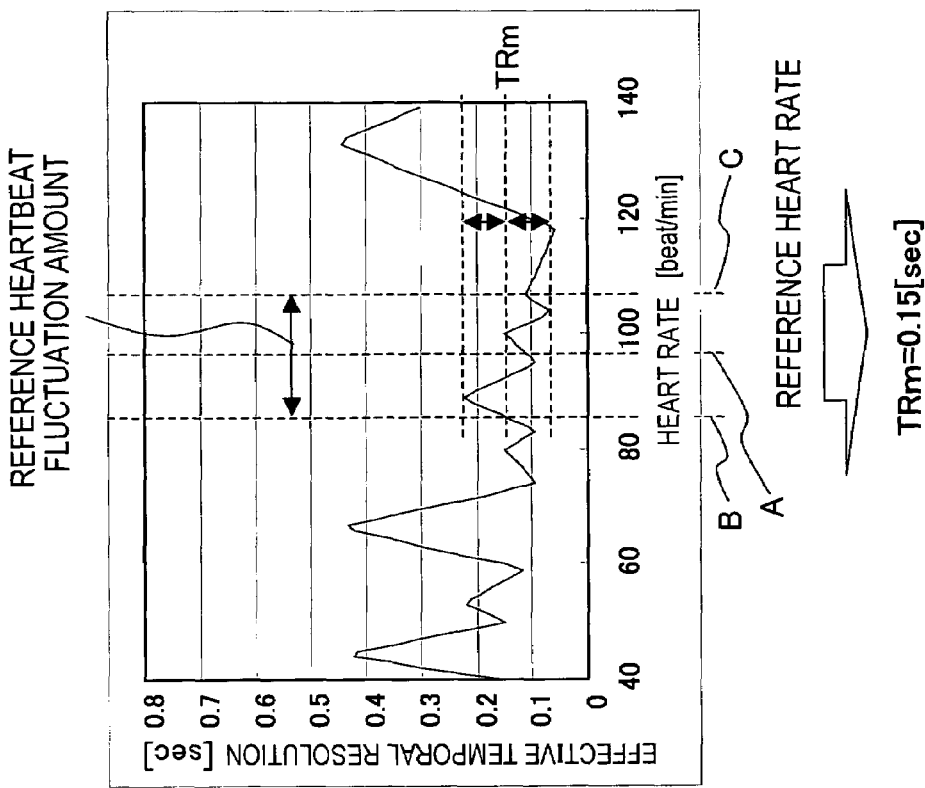
FIG. 43(a) is a view that illustrates a method of determining a scan time that used a mean temporal resolution according to the seventh embodiment, showing a case using the mean temporal resolution (time of 0.7 seconds scan), and (b) is a view that illustrates a method of determining a scan time that used a mean temporal resolution according to the seventh embodiment, showing a case using the mean temporal resolution (time of 0.9 seconds scan)
Figure 43B:
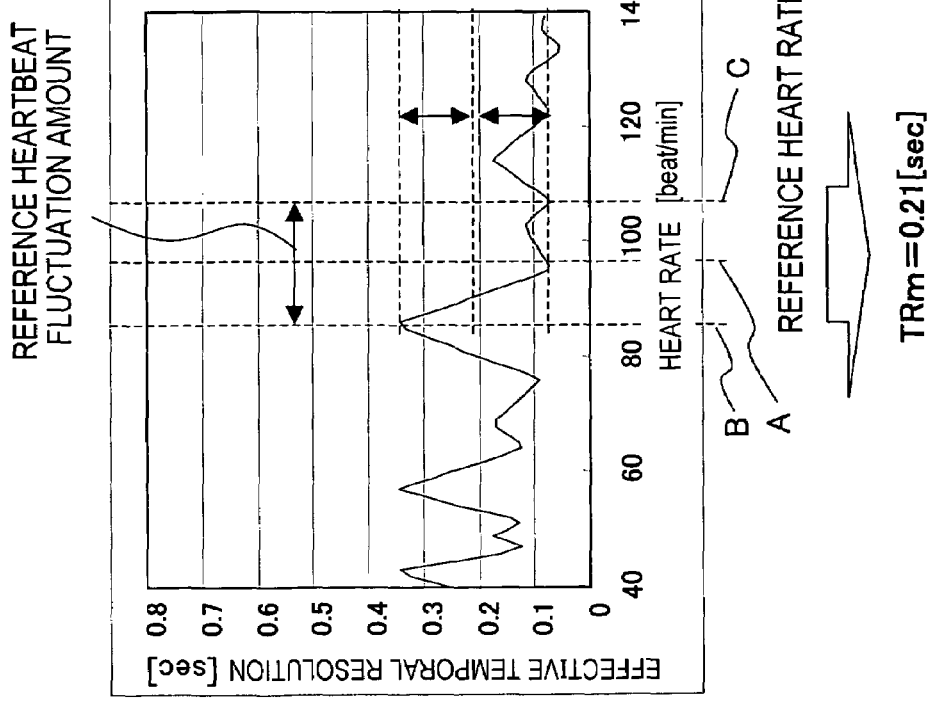

When using mean temporal resolution, a correlation function as shown in FIG. 43 is used. A correlation function is preferably prepared in advance for each scan time in accordance with the combination of scanning parameters.

In step S3403, for the mean temporal resolution, weighted addition of the effective temporal resolution is performed using a weight value in accordance with a frequency by employing a center of gravity value as a criterion, and the weighted additional value is determined as the scan time at scanning that is the scanning speed. By applying a weighting to the incidence frequency of heart rates that correspond to each effective temporal resolution, the average effective temporal resolution is determined as a mean temporal resolution TRm. When using the mean temporal resolution, it is possible to improve the image quality of an image by selecting an intermediate value that is not far removed from a minimum value and maximum value of the effective temporal resolution to suppress the impact of temporal fluctuations to a minimum.

Calculation of the mean temporal resolution will be described referring to FIG. 43. In the case of a scan time of 0.7 sec, for an object to be examined with a reference heartbeat range from 85 to 105 [beat/min], the frequency of a heart rate of 85 [beat/min] is 2, the frequency of a heart rate of 90

[beat/min] is 2, the frequency of a heart rate of 95 [beat/min] is 3, the frequency of a heart rate of 100 [beat/min] is 2, the frequency of a heart rate of 105 [beat/min] is 1, and the total sum of frequencies is 9. The frequency ratio of the heartbeats is: 2/9 for the heart rate of 85 [beat/min], 2/9 for the heart rate of 90 [beat/min], 3/9 for the heart rate of 95 [beat/min], 2/9 for the heart rate of 100 [beat/min], and 1/10 for the heart rate of 105 [beat/min].

In this example, in the case of a scan time of 0.7 [sec], when the effective temporal resolution of the heart rate of 85 [beat/min] is 0.3 [sec], the effective temporal resolution of the heart rate of 90 [beat/min] is 0.2 [sec], the effective temporal resolution of the heart rate of 95 [beat/min] is 0.08 [sec], the effective temporal resolution of the heart rate of 100 [beat/min] is 0.1 [sec], and the effective temporal resolution of the heart rate of 105 [beat/min] is 0.08 [sec], the mean temporal resolution is determined as follows.

$$0.3*2/10+0.2*2/10+0.08*3/10+0.1*2/10+0.08*1/10=0.152 [\text{sec}] \quad \text{[Formula 23]}$$

Likewise, in the case of a scan time of 0.9 [sec], for an object to be examined who similarly has a reference heartbeat range from 85 to 105 [beat/min], when the effective temporal resolution of the heart rate of 85 [beat/min] is 0.15 [sec], the effective temporal resolution of the heart rate of 90 [beat/min] is 0.20 [sec], the effective temporal resolution of the heart rate of 95 [beat/min] is 0.1 [sec], the effective temporal resolution of the heart rate of 100 [beat/min] is 0.15 [sec], and the effective temporal resolution of the heart rate of 105 [beat/min] is 0.1 [sec], the mean temporal resolution is determined as follows.

$$0.15*2/10+0.20*2/10+0.1*3/10+0.15*2/10+0.1*1/10=0.14 [\text{sec}] \quad \text{[Formula 24]}$$

That is, when the scan time is 0.7 [sec/rot], the mean temporal resolution TRm (0.7)=0.152 [sec], and when the scan time is 0.9 [sec/rot], the mean temporal resolution TRm(0.9)=0.14 [sec].

In step S3404, since TRm (0.7)>TRm(0.9), it is determined that the scan time with the higher mean temporal resolution is 0.9 [sec/rot]. The scan time of 0.9 [sec/rot] is thus set as a scanning parameter.

Use of the mean temporal resolution TRm is suitable for an object to be examined having an eruptive abnormality such as a sudden increase in a pulse wave.

In step S3404, either one of temporal resolution width, mean temporal resolution, or lowest temporal resolution as calculated in step S3403, or a combination of these may be used as a basis for determining the scan time as the scanning speed. In that case, if there is a scanning speed that occupies the majority among the three scanning speeds consisting of a scanning speed at which the lowest temporal resolution is highest, a scanning speed at which the temporal resolution fluctuation width is narrowest, and a scanning speed at which the mean temporal resolution is highest, that scanning speed may be selected.

According to the present embodiment as described above, by counting the frequencies at which the effective temporal resolution occurs for each predetermined range, taking a weighted mean value thereof as a mean temporal resolution, and selecting a scanning speed whereby that resolution is highest, it is possible to set a scanning speed that can further enhance the temporal resolution.

Although a tomographic apparatus that uses X rays was described according to the above three embodiments (fifth embodiment, sixth embodiment, and seventh embodiment), the present invention is not limited thereto, and it can also be applied to a tomographic apparatus that uses gamma rays, neutron rays, positrons, electromagnetic energy or light. Further, in the case of an X-ray CT apparatus, the scanner method is not limited to a first generation, second generation, third generation or fourth generation method, and the invention is also applicable to a helical scan or a circular scan. The invention can also be used for an electron beam CT, a cathode scan CT or a multi-tube CT equipped with a plurality of X-ray sources.

Further, regarding the detector shape, the invention is applicable to any kind of detector such as a detector disposed on a cylindrical surface that is centered on an X-ray source, a flat panel detector, a detector disposed on a spherical surface that is centered on an X-ray source, and a detector disposed on a cylindrical surface that is centered on the circulation axis, and with respect to the number of rows of a detector, the invention is applicable to various detectors, from a single-row detector to a multi-row detector.

In this embodiment, since X-ray transmission data or a reconstruction image that should actually be handled discretely is handled as continuous data, the data or image may be discretely calculated by performing interpolation in three directions consisting of the phase direction, the detector row direction and the detector channel direction using an interpolation method such as Lagrange interpolation. At this time, calculation may be performed by interpolation in four directions that include interpolation in the time direction.

According to this embodiment, even when scanning an object to be examined for whom there is a tendency for the heart rate at the time of actual scanning to differ from that when setting the scanning speed, it is possible to select a scanning speed that can optimize the temporal resolution in accordance with the heart rate fluctuation tendency, and thus an improvement in temporal resolution that is one factor that determines the quality of an image can be attempted.

It is therefore possible to avoid examination discrepancies caused by a deterioration in temporal resolution, and thus the time and labor involved in reattempting scanning can be eliminated, improved examination efficiency can be realized, and ineffective radiation exposure that accompanies scanning reattempts can be avoided.

Furthermore, the accuracy of extracting a calcium score or a stricture of, for example, a coronary artery that has a large degree of movement and is liable to be affected by heartbeat fluctuations is enhanced to obtain a superior diagnostic ability. Although a tomographic apparatus that uses X rays is used according to this embodiment, the present embodiment is not limited thereto, and it can also be applied to a tomographic apparatus that uses gamma rays, neutron rays, positrons, electromagnetic energy or light.

EIGHTH EMBODIMENT

The eighth embodiment relates to an X-ray CT apparatus, and more particularly to an apparatus for the purpose of scanning sites that carry out a periodic motion in an object to be examined, such as a cardiovascular region or a respiratory organ. When a moving body member is scanned with an X-ray CT apparatus, artifacts that are caused by movement of the object are generated in the obtained tomogram (reconstruction image). To decrease the occurrence of these artifacts, in general, in combination with use of a biosensor such as a respiration sensor or an electrocardiograph, measurement is performed by a device that converts a physiological motion into an electrical signal, and the obtained electrical signals are used to control scanning and process the images.

ECG-gated reconstruction is known as a method of scanning the heart as the scanning object.

According to this method, electrical signals that were measured by an electrocardiograph are attached to scanning data (transmitted X-ray data) and collected, and image reconstruction is performed based on the obtained scanning data, to thereby enable obtainment of a cardiac tomogram in an arbitrary cardiac phase.

For example, Japanese Patent Laid-Open No. 2002-330961 discloses an X-ray CT apparatus that collects, from a plurality of heartbeats, scanning data (hereafter, referred to as "segments") of different views or scans that were scanned in approximately the same cardiac phase based on R waves of an electrocardiographic waveform. It is possible to attempt to enhance the temporal resolution by performing image reconstruction based on segments that were collected in this manner.

Figure 44:
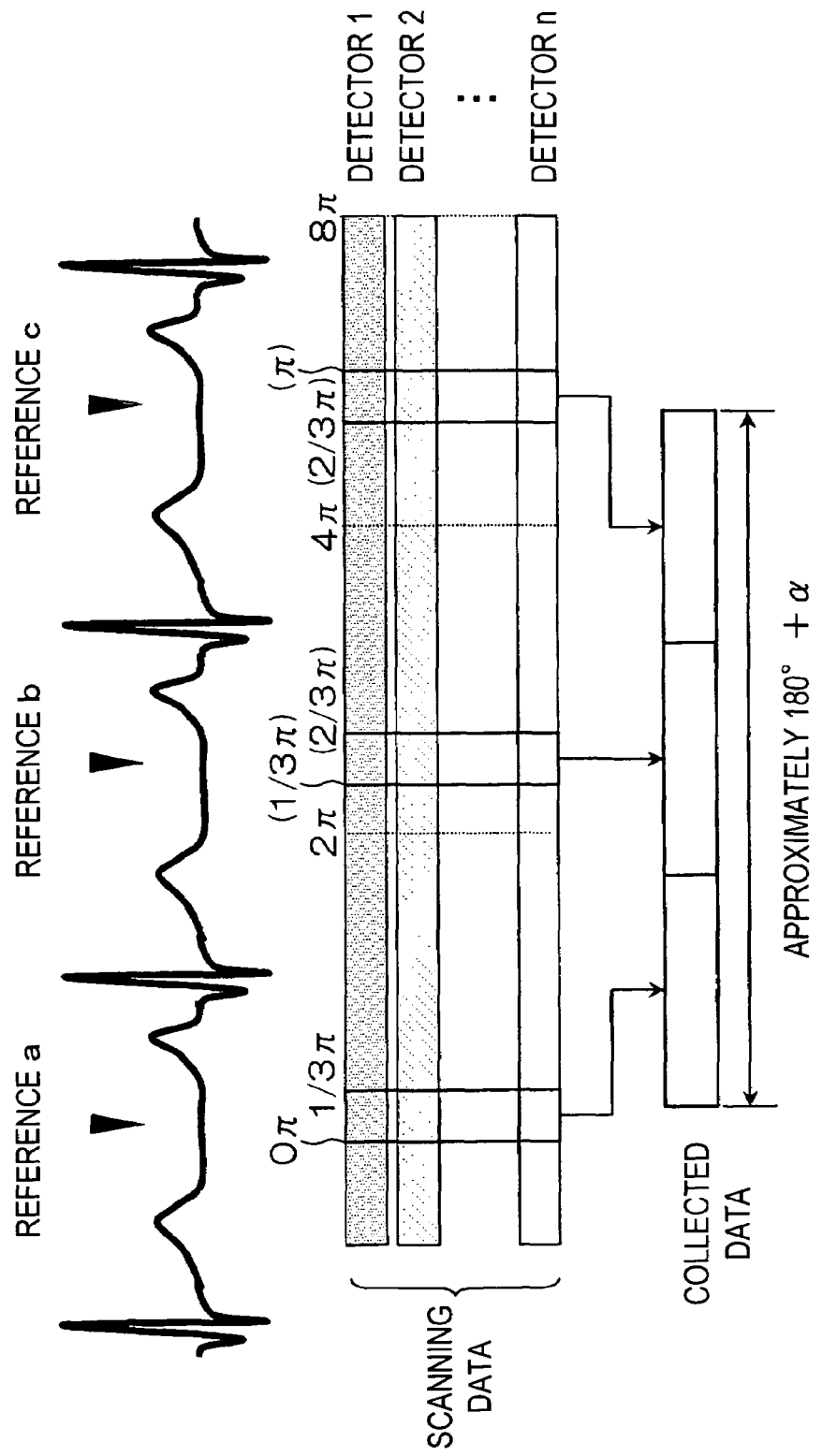
FIG. 44 is a schematic diagram showing a calculation example of a segment extraction range according to a method as the conventional technique with respect to the eighth embodiment.

A method of extracting segments for ECG-gated reconstruction according to the above described X-ray CT apparatus will now be described based on FIG. 44. FIG. 44 illustrates an example in which three segments are collected. Scanning data of different scanning angles in the same temporal phase is collected based on reconstruction reference positions. The data amount collected is the amount of the scanning angle that is necessary for reconstruction (approximately $180°+\alpha$, $\alpha$: X-ray cone angle). In the example shown in FIG. 44, segments are collected by employing 0 to $1/3\pi$ from reference a, $\pi/3$ to $2\pi/3$ from reference b, and $2\pi/3$ to $\pi$ from reference c as extraction ranges. To create a tomogram at an arbitrary slice position, a set of data of the same slice position is created by conducting interpolation processing between scanning data that was obtained from each detector row, to then perform image reconstruction.

However, when collecting segments from a plurality of heartbeats on the basis of image reconstruction electrocardiogram information, all of the collected segments are not necessarily suitable for image reconstruction. For example, in comparison to a segment collected from a heartbeat for which the heart rate is low, there is a greater possibility of a segment collected from a heartbeat for which the heart rate is high being affected by heartbeat motion, which results in motion artifacts. That is, variations in significance exist with respect to ECG-gated reconstruction in a plurality of collected segments. Consequently, in some cases segments with a low significance are included in segments that are collected. In that case, there is a problem of the possibility of image quality being degraded due to the occurrence of motion artifacts or the like in the reconstruction image that is created.

Thus, in consideration of the above described problem, an object of the X-ray CT apparatus according to this embodiment is to provide an X-ray CT apparatus that can contribute to enhancing spatial resolution or temporal resolution when collecting segments of the same cardiac phase from a plurality of heartbeats.

In this connection, as used in this embodiment, the term "reconstruction reference position" refers to a position that represents a cardiac phase position of a cardiac image created by an operator.

Further, the term "significance" refers to the level of contribution to a reconstruction image of scanning data that is collected on the basis of the reconstruction reference position, and it corresponds to the level of contribution of scanning data at each reconstruction reference position with respect to an amount of scanning data collected for a scanning angle of $180°+\alpha$ ($\alpha$: X-ray cone angle). More specifically, the fact that the significance of a certain piece of scanning data is high means that the influence that scanning data has on the image quality of a reconstruction image (for example, a cardiac image) is high in comparison to other scanning data.

Further, the term "feature quantity of periodic motion" refers to a numerical value that represents a feature of periodic motion, for example, a standard deviation of a pulse height when using a waveform to display a periodic motion or a period of a periodic motion.

Hereunder, a preferred embodiment of the X-ray Ct apparatus according to the present invention is described in detail in accordance with the attached drawings.

Figure 45:
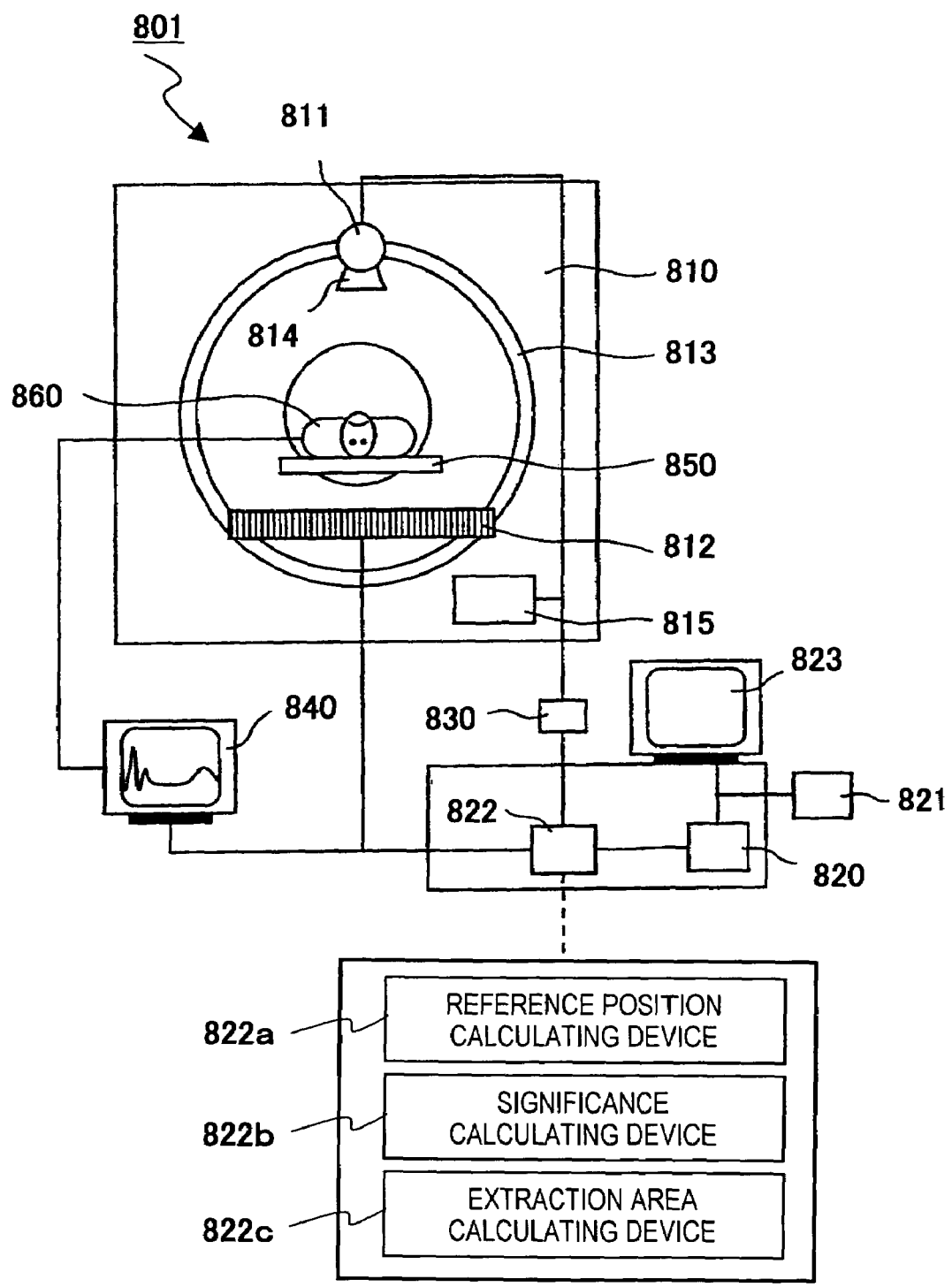
FIG. 45 is a block diagram showing an X-ray CT apparatus according to the eighth embodiment.

FIG. 45 is a schematic configuration diagram showing the configuration of an X-ray CT apparatus according to one embodiment of the present invention. An X-ray CT apparatus 801 shown in FIG. 45 comprises a scanner gantry part 810 that performs X-ray irradiation and detection, an image processor 820 that performs image reconstruction calculation based on scanning data that is detected by the scanner gantry part 810, a measurement controller 830 that controls a measurement operation in the scanner gantry part 810, and a patient table 850 on which an object to be examined 860 lies.

The scanner gantry part 810 comprises an X-ray tube 811 that irradiates X-rays, an X-ray detector 812 that detects X-rays that passed through the object 860 to output scanning data, and a rotary table 813 that is equipped with the X-ray tube 811 and the X-ray detector 812. A collimator 814 that controls the direction of an X-ray flux is attached to the X-ray tube 811. The X-ray detector 812 is a multi-slice X-ray detector that can acquire scanning data of a plurality of positions (n slices) at the same time by aligning a plurality of detectors 1, 2 . . . n in n rows in the body axis direction of the object 860. The rotary table 813 is rotated by a rotational driving apparatus 815. The rotational driving apparatus 815 is controlled by a measurement controller 830.

The image processor 820 includes a mouse 821 that comprises a pointing device such as a mouse or a keyboard, a computer 822 that is connected to a measurement controller 830 and carries out control and operation of the measurement controller 830, and a display 823 comprising a CRT or a liquid crystal display.

The X-ray intensity generated by the X-ray tube 811 is controlled by the measurement controller 830. The measurement controller 830 is operated and controlled by the computer 822. The computer 822 is connected to an electrocardiograph 840 for acquiring electrocardiographic waveforms of the object 860.

The computer 822 comprises reference position calculating device 822a, significance calculating device 822b, and extraction range calculating device 822c.

Figure 46:
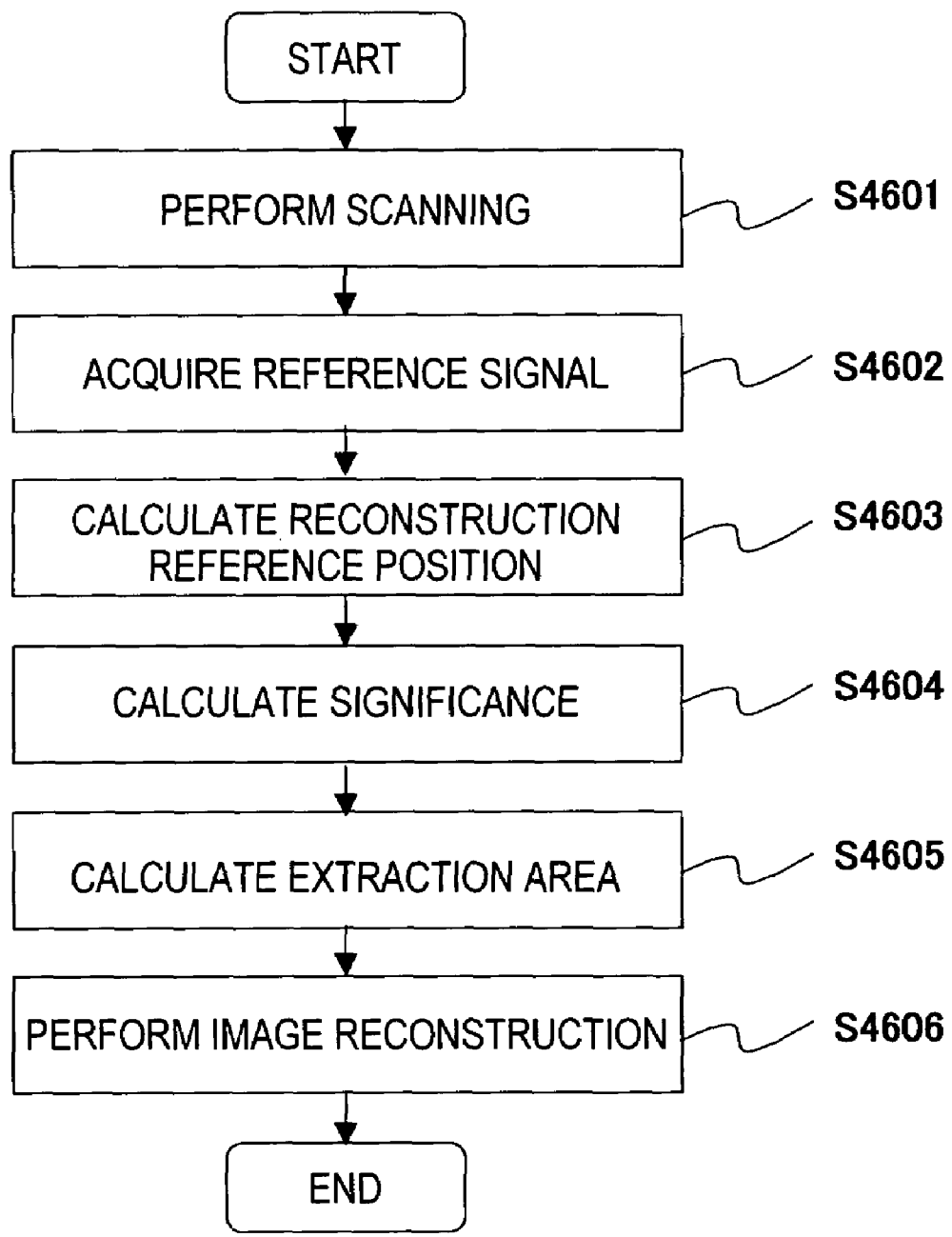
FIG. 46 is a flowchart illustrating processing for obtaining a tomogram using the X-ray CT apparatus shown in FIG. 45.

Next, a process for creating a cardiac image using the X-ray CT apparatus 801 will be described on the basis in FIG. 46. FIG. 46 is a flowchart that illustrates a process of creating a cardiac image. Hereunder, the process is described in step order.

(Step S4601)

A scanning region that includes the heart of the object 860 is scanned by the X-ray CT apparatus 801. Simultaneously with the collection of scanning data, the X-ray CT apparatus 801 collects electrocardiogram information using the electrocardiograph 840.

(Step S4602)

Figure 47:
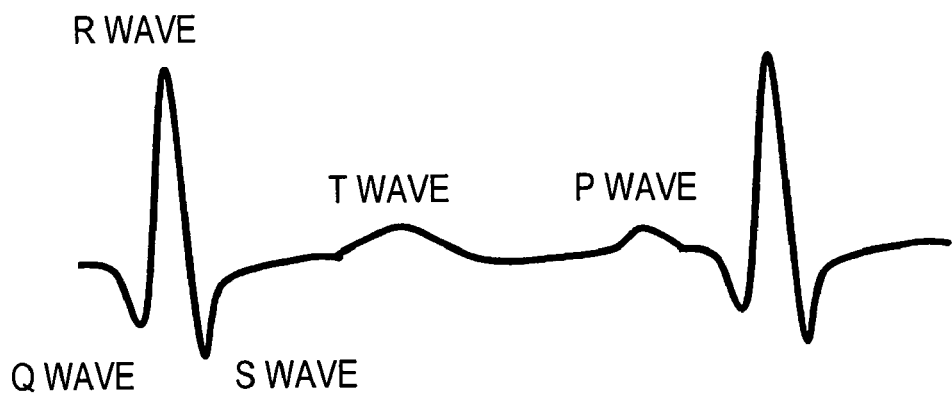
FIG. 47 is a schematic diagram showing one example of an electrocardiographic waveform that can be obtained with an electrocardiograph.

When performing ECG-gated reconstruction, signals as references for segments are acquired from the electrocardiogram information collected in step S4601. FIG. 47 shows one example of a common electrocardiographic waveform.

Although in most cases the position of an R wave, for which a peak position can be simply identified, is normally used as a reference signal, a P wave, Q wave, S wave or T wave may also be used.

(Step S4603)

Figure 48:
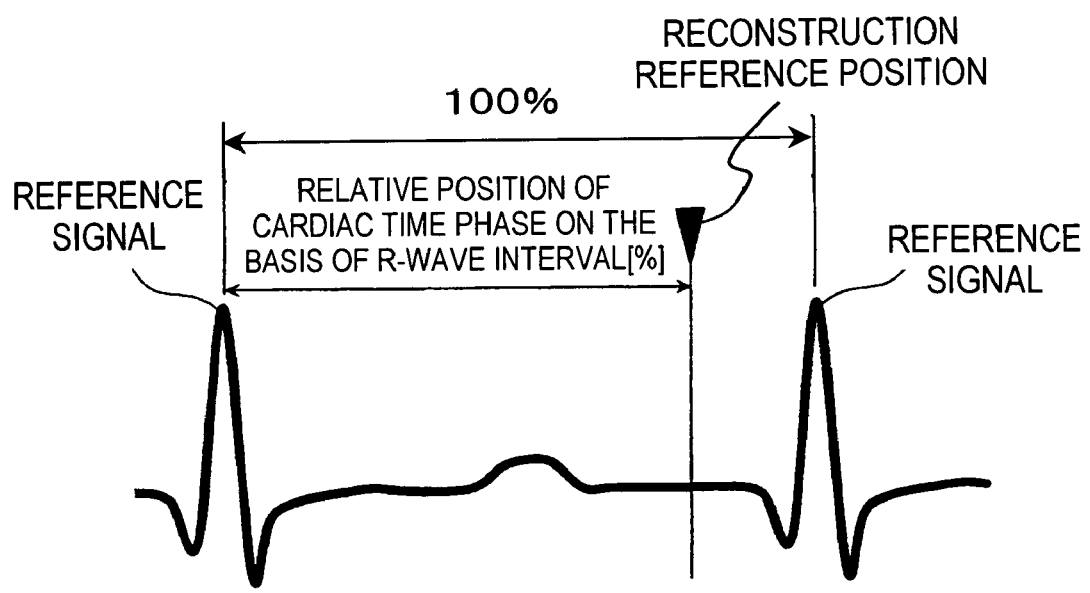
FIG. 48 is a schematic diagram showing one example of a reconstruction reference position that is calculated by reference position calculating device.
Figure 49:
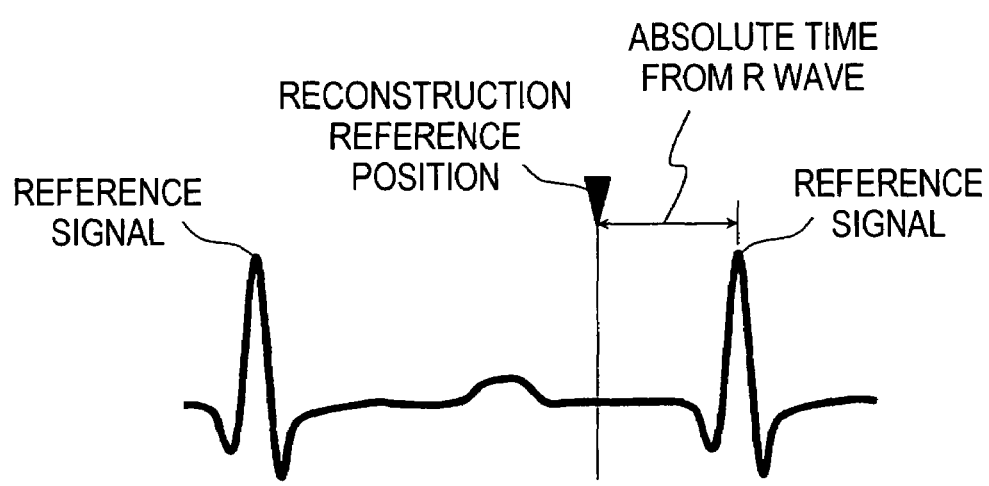
FIG. 49 is a schematic diagram showing one example of a reconstruction reference position that is calculated by reference position calculating device.

The reference position calculating device 822a calculates reconstruction reference positions on the basis of reference signals acquired in step S4602. FIG. 48 is a view that shows one example of a reconstruction reference position, in which a reconstruction reference position is determined using a relative position in a case where R waves are taken as reference signals and a time interval until an adjacent R wave is taken as 100%. The value of the relative position is decided by the operator. FIG. 49 is a view that shows an example of a reconstruction reference position, in which R waves are taken as reference signals and a reconstruction reference position is determined using an absolute time from an R wave. The value of the absolute time is decided by the operator.

(Step S4604)

The significance calculating device 822b calculates the significances for various reconstruction reference positions that were calculated in step S4603.

Figure 50:
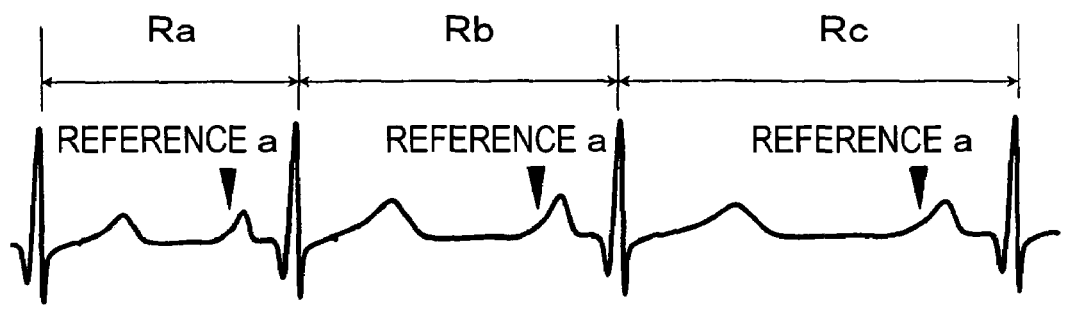
FIG. 50 is a schematic diagram showing one example of significance that is calculated by significance calculating device.

FIG. 50 is a view showing one example that calculates significances from one heartbeat period. When one heartbeat period is long, cardiac motion is slow in comparison to a short heartbeat period, and the influence of cardiac motion on scanning data that was scanned in that period is small. More specifically, segments that are collected based on reconstruction reference positions that are included in one long heartbeat period are more suitable for ECG-gated reconstruction than those for one short heartbeat period. Based on this idea, a higher significance is set for reconstruction reference positions included in one long heartbeat period. FIG. 50 is a view showing an electrocardiographic waveform that was acquired during cardiography, in which reference characters Ra, Rb, and Rc represent one heartbeat period of respective cardiac motions. When the reconstruction reference positions to be used for ECG-gated reconstruction are taken as reference a, reference b and reference c, the significances La, Lb, and Lc of the respective reconstruction reference positions are represented by the formula shown in [Formula 25] below.

$La=Ra/(Ra+Rb+Rc)$ $Lb=Rb/(Ra+Rb+Rc)$ $Lc=Rc/(Ra+Rb+Rc)$ [Formula 25]

Figure 51:
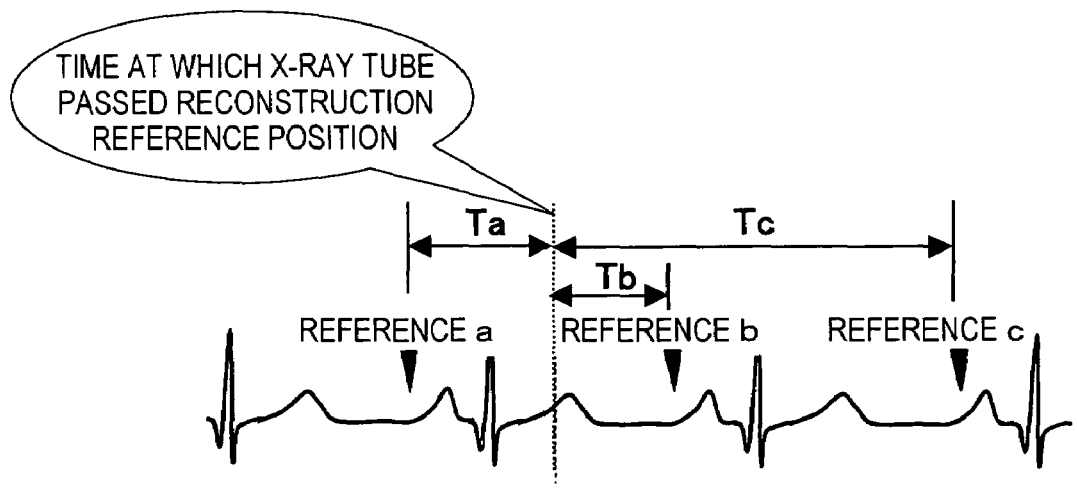
FIG. 51 is a schematic diagram showing one example of significance that is calculated by significance calculating device.

FIG. 51 is a view showing one example of calculating significance based on a time interval from an X-ray tube transit time to a reconstruction reference position. In an X-ray CT apparatus (multi-slice CT apparatus) comprising a plurality of X-ray detectors 812 in the body axis direction, since X-rays that have an angle of divergence (cone angle) in the body axis direction are utilized, the amount of artifacts that are generated increases according to an increase in the quantity of scanning data that is detected by X-ray detectors 812 at the two ends.

As described above, in ECG-gated reconstruction, image reconstruction is performed by collecting segments that were scanned at a plurality of times, and the greater the degree of temporal remoteness of a segment that was scanned at a time that is temporally remote from the time that the X-ray tube passed an arbitrary reconstruction reference position, the more that the proportion of segments scanned from X-ray detectors 812 near to both ends of the X-ray detectors 812 increases, and the possibility of artifacts being caused grows.

Based on the foregoing idea, the closer a reconstruction reference position is temporally to the time that the X-ray tube passed an arbitrary reconstruction reference position, the higher the significance that is set for that reconstruction reference position.

FIG. 51 is a view showing an electrocardiographic waveform that was acquired during cardiography, in which reference characters Ta, Tb and Tc denote time intervals from a time that the X-ray tube passes an arbitrary reconstruction reference position until reference a, reference b and reference c as reconstruction reference positions used for ECG-gated reconstruction. The significances of the respective reconstruction reference positions are represented by the formula shown in [Formula 26] below.

$La=(1/Ta)/(1/Ta+1/Tb+1/Tc)$ $Lb=(1/Tb)/(1/Ta+1/Tb+1/Tc)$ $Lc=(1/Tc)/(1/Ta+1/Tb+1/Tc)$ [Formula 26]

Figure 52:
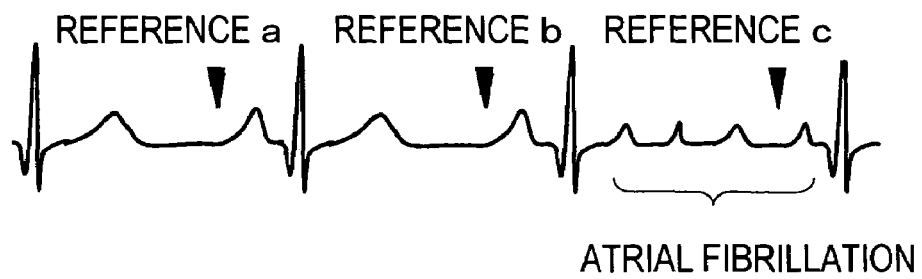
FIG. 52 is a schematic diagram showing one example of significance that is calculated by significance calculating device.

FIG. 52 is a view showing one example that calculates significances based on the regularity of cardiac motion. ECG-gated reconstruction is a method that attempts to enhance temporal resolution by utilizing the phenomenon that the heartbeats in a regular manner.

However, there is a high possibility that the patient that is the object of the heart examination may have some form of heart disease, and for example in a case where atrial fibrillation occurs, the regularity of the cardiac motion is disturbed. In that case, since regularity of cardiac motion is not assured for segments that were scanned during atrial fibrillation, it is difficult to say that the relevant image data is image data that is divided into segments suitable for ECG-gated reconstruction. Based on the foregoing idea, the greater the extent to which a reconstruction reference position is included in a regular heartbeat, the higher the significance that is set for that position.

FIG. 52 is a view showing an electrocardiographic waveform that was acquired during cardiography, which shows an example of occurrence of atrial fibrillation around a reference c when reference a, reference b and reference c are taken as reconstruction reference positions to be used in ECG-gated reconstruction. When atrial fibrillation occurs, small irregular waves appear in the shape of the electrocardiographic waveform. When this kind of abnormality is found in an electrocardiographic waveform, it is considered that the regularity of the cardiac motion was disrupted, and the significance of a reconstruction reference position (reference c in FIG. 52) that is included in a time period in which the electrocardiographic waveform is abnormal is set lower than the significance of other reconstruction reference positions. The regularity of cardiac motion is, for example, evaluated by calculating the standard deviation of wave heights of the electrocardiographic waveform.

Examples of other methods of calculating significance include a method in which a normal heartbeat waveform of the patient is previously stored as a template, and template matching is conducted for respective waveforms. That level of matching is then reflected in the significance. More specifically, the higher the level of matching of the heartbeat in which a reconstruction reference position is included, the higher the significance that is set for that reconstruction reference position.

Although according to the above described FIGS. 50, 51 and 52, significance was calculated based on a certain single indicator, significance may also be calculated by combining a plurality of indicators. Further, although a method was described that automatically calculates significance based on an electrocardiographic waveform, the electrocardiographic waveform may also be displayed on a display 823 to allow the addition of manual modification according to the judgement of the operator.

Figure 53A:
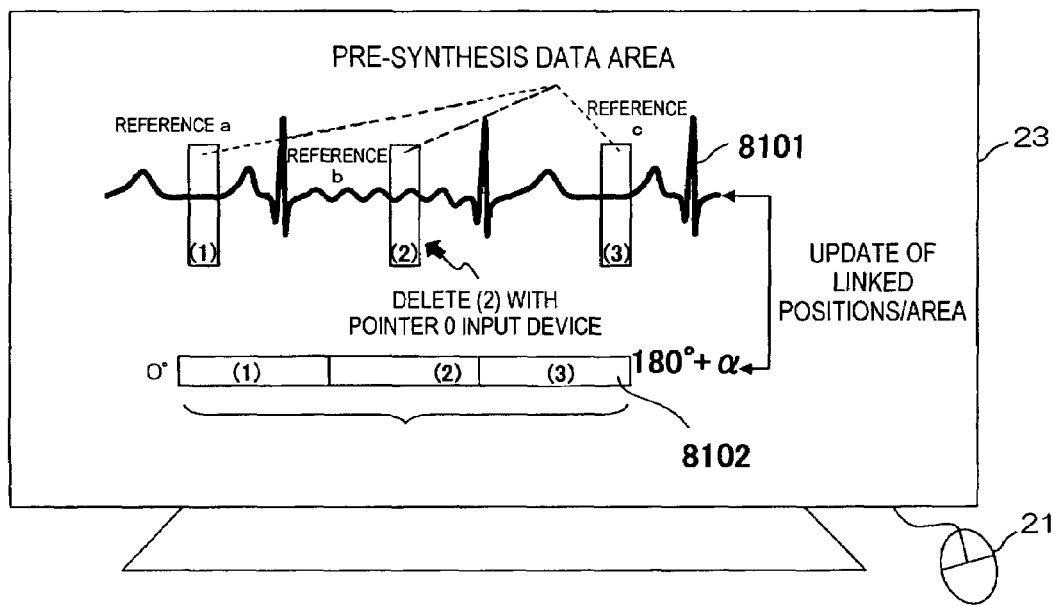
FIGS. 53(a) and (b) are schematic diagrams showing screen display examples that display an electrocardiographic waveform 8101 and the significance of a segment 8102 in association with each other.
Figure 53B:
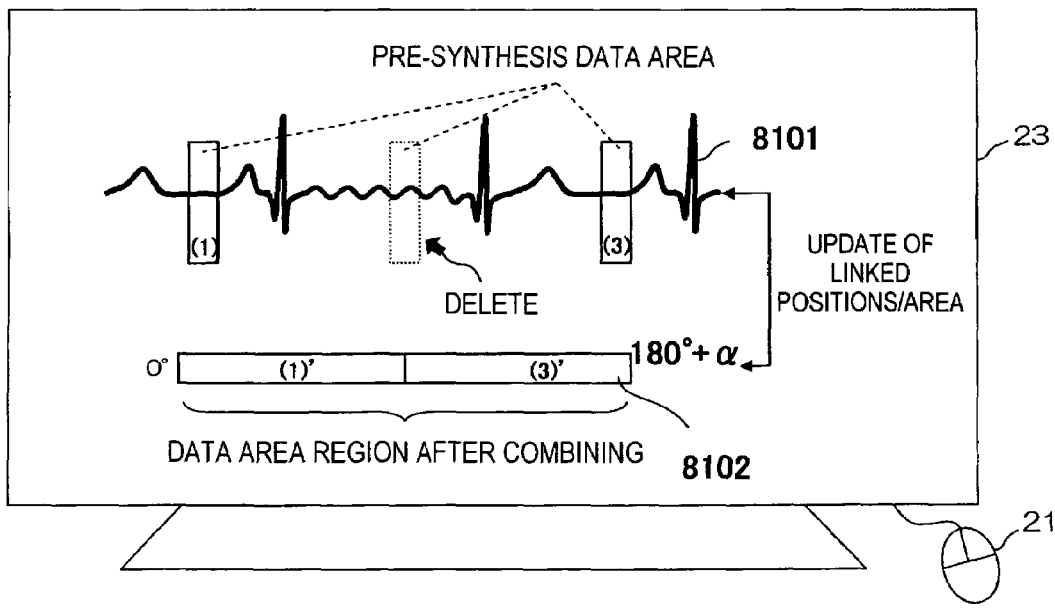

Hereunder, a method of manually modifying the significance will be described referring to FIG. 53. FIG. 53 is a schematic diagram that shows an example of a screen display in which an electrocardiographic waveform 8101 and the significances of segments 8102 are displayed in association with one another.

FIG. 53-(a) is a view showing a screen display example for a display 823 that shows that the extraction range calculating device 822c collected three segments from reference a, reference b and reference c as reconstruction reference positions. FIG. 53-(b) is a screen display example that shows a result obtained when an operator used the mouse 821 to delete a segment of a section in which there was atrial fibrillation.

In FIG. 53-(a), for a segment (2) that corresponds to a reference b position that is included in a heartbeat in which atrial fibrillation occurred, the heartbeat regularity is low in a comparison of references a, b and c as reconstruction reference positions. Therefore, the significance of reference b is markedly low or is less than a preset significance threshold value. In this case collection is performed for the two segments at references a and c. It is thus possible to perform image reconstruction that excludes a segment with a low significance, to enable enhancement of image quality.

More specifically, after the operator specifies the display area of segment (2) by dragging or clicking with the mouse 821, the operator inputs an instruction to delete that display area. Consequently, in response to the deletion processing, the significance of segments (1) and (3) that are the portions at reference a and reference c increases (i.e. the proportion of each of segments (1) and (3) increases in the combined data range area). By bringing together the two segments (1)' and (3)' after this change, an area of the post-combination data range is created. In this manner, the number of segments to be collected may be adjusted in accordance with the significance.

The above described FIGS. 50, 51 and 52 can be applied to ECG-gated reconstruction when performing a dynamic scan using a single slice X-ray CT apparatus or a multi-slice X-ray CT apparatus. Further, for ECG-gated reconstruction when performing a helical scan using a multi-slice X-ray CT apparatus, a method that calculates the significance based on a time at which the X-ray tube 811 passed the reconstruction reference position as shown in FIG. 51 can be applied.

(Step S4605)

Figure 54:
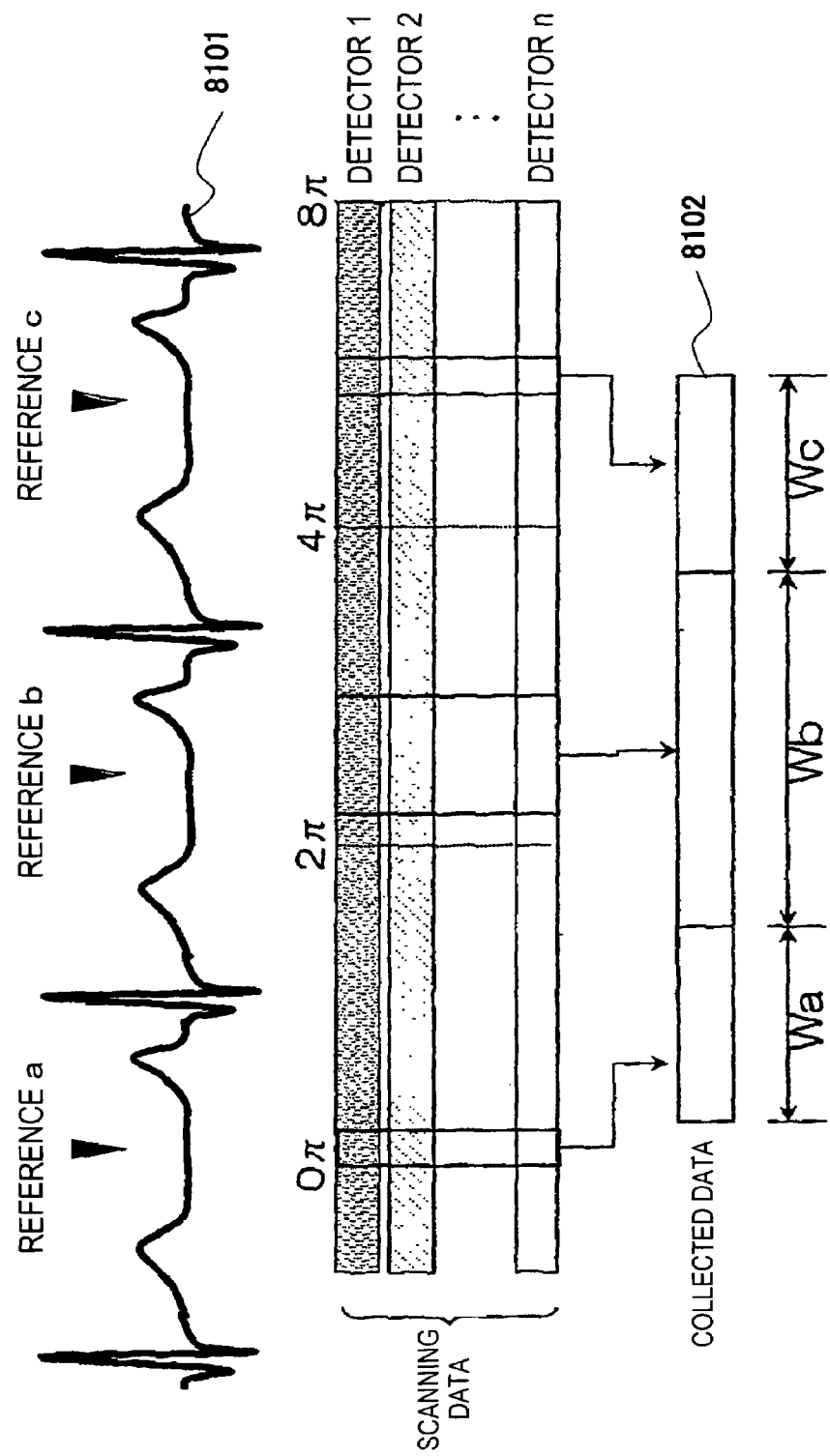
FIG. 54 is a schematic diagram showing a weighted display example.

The extraction range calculating device 822c calculates an extraction range of segments based on the significances as calculated in step S4604. The extraction range calculating device 822c adjusts the extraction range based on the significance that is set for each reconstruction reference position. FIG. 54 illustrates one example thereof. FIG. 54 illustrates an extraction range in a case where the relation between significance Ia, Ib and Ic of references a, b, and c is Ia:Ib:Ic=1:2:1, in which the widths of data widths Wa, Wb and Wb of segments that are extracted based on references a, b and c in correspondence with the ratio of significance are adjusted such that Wa:Wb:Wc=1:2:1. By increasing the proportion of a segment that was extracted from a reference position with a high significance in this manner, it is possible to enhance the image quality.

In this connection, although in FIG. 54 the ratio of data widths Wa, Wb and Wc was adjusted such that it is the same as the ratio of the significances Ia, Ib and Ic, the data widths may also be calculated upon assigning arbitrary weights to the significances. The weighting may be preset in the image processor 820, or the operator may input the weights as the occasion arises.

When the weighting to be assigned is, for example, Ia:Ib:Ic=1:2:1, when each significance is raised to a power of a coefficient 0.5 to calculate Wa, Wb and Wc, then Wa:Wb:Wc=1:1.4:1, and thus the influence of the significances on the data widths can be reduced. Thereby, even in a case of overcorrection, i.e. when a difference in significance is too large, data widths can be set at suitable proportions.

Conversely, when the significance ratio is Ia:Ib:Ic=1:2:1 and each significance is raised to the power of a coefficient 2 to calculate the widths Wa, Wb and Wc, then Wa:Wb:Wc=1:4:1 and the influence of the significances on the data widths can thus be increased.

(Step S4606)

The extraction range calculating device 822c collects the calculated segments, and the image processor 20 performs reconstruction processing to generate a reconstruction image based on the post-combination data in which these segments are assembled.

According to the above described embodiment, although as shown in FIG. 53 an embodiment was illustrated in which an operator used the mouse 821 to modify reconstruction reference positions that were calculated by the extraction range calculating device 822c, a configuration may also be adopted whereby only a heartbeat waveform is displayed on the display 823 based on heartbeat data, and the operator specifies heartbeat phases to be used for image reconstruction among that heartbeat waveform and performs image reconstruction using segments that correspond to those heartbeat phases.

Further, a configuration may also combine the use of a weight display that displays the weight of each segment. The operator carries out area specification by dragging or clicking the mouse 821 on a heartbeat phase to which a weight is to be adjusted. At this time, adjustment may be performed so that the total sum of weights for the X-ray CT apparatus 801 is 1. For example, when two heartbeat phases were selected, the X-ray CT apparatus 801 may be adjusted so that when the weight of one heartbeat phase is increased, the weight of the other heartbeat phase decreases, such that the total weight of the two heartbeat phases is 1.

Although according to this embodiment image reconstruction was performed that takes account of cardiac motion using the electrocardiograph 840 as a periodic motion recognition apparatus, another device that recognizes a periodic motion of a living organism, for example, a pulse sensor or a respiration sensor may be used as the periodic motion recognition apparatus. When a respiratory organ sensor is used, the image quality of image reconstruction of a lung region can be enhanced. ECG-gated reconstruction also includes a method that restricts temporal discontinuity by overlapping adjoining segments, and the present invention can also be applied to that method. More specifically, the method of overlapping or the overlapping width of data can be adjusted by increasing the contribution ratio of segments with a high significance, to enable an enhancement in image quality.

The present embodiment can provide an X-ray CT apparatus that contributes to improving a spatial resolution or a temporal resolution when collecting segments of the same cardiac phase from a plurality of heartbeats.

Although a tomographic apparatus that uses X rays is used according to this embodiment, the present embodiment is not limited thereto, and it can also be applied to a tomographic apparatus that uses gamma rays, neutron rays, positrons, electromagnetic energy or light.

INDUSTRIAL APPLICABILITY

The present invention can generate a tomogram of a site that performs a periodic motion in an object to be examined while suppressing radiation exposure by X-rays. Further, when generating a tomogram using gamma rays, neutron rays, positrons, electromagnetic energy or light that is emitted from an agent that was injected or infused into an object to be examined, it is possible to collect data for generating a tomogram more efficiently.

The invention claimed is:

1. A radiotomography apparatus, comprising:
a radiation detection device that irradiates radiation from a radiation source in multiple directions around an object to be examined and detects radiation that is transmitted through the object from the multiple directions;
a table on which the object lies and which can move the object in a body axis direction of the object;
a reconstruction parameter setting device that sets reconstruction parameters that include an amount of movement of the table in the body axis direction, and that are used to reconstruct an image of the object;
a reconstruction view area calculating device that calculates a reconstruction view area for at least one data segment that is necessary for a reconstruction calculation that is determined for each spatial position that is reconstructed based on the reconstruction parameters;
a reference segment position setting device that sets a reference segment position in the calculated reconstruction view area according to a phase signal that is obtained by dynamic analysis of the object;
an effective segment calculating device that calculates a data segment including the set reference segment position as an effective segment using a predetermined weight function, said effective segment calculating device including
number of effective segments calculating device that calculates a number of effective segments for which the set reference segment position is present in the reconstruction view area,
a segment width calculating device that calculates a width of an effective segment that is defined at the reference segment position for each of the calculated number of effective segments, using an area which an adjacent data segment thereof has, and
a weight function calculating device that calculates said weight function which highly contributes to image reconstruction of data segments for which the phase signals are equal by widths of the calculated effective segments and the set reference segment positions, and for which the sum of weights of data segments that face the effective segments are equal; and
an image creating device that creates an image by reconstructing the calculated effective segments.

2. The radiotomography apparatus according to claim 1, wherein based on movement information of one part of an object to be examined that moves in a predetermined period, the reference segment position setting device sets a position of a reference segment that corresponds to a predetermined phase in that period.

3. The radiotomography apparatus according to claim 2, wherein the reconstruction parameter setting device comprises device that displays information to enable setting of a position of a reference segment that corresponds to a predetermined phase in a period of the movement information.

4. The radiotomography apparatus according to claim 1, wherein the segment width calculating device folds the effective segment with respect to a natural number multiple of $\pi$, and determines a width of each effective segment such that a fixed ratio exists between adjacent effective segments, and with respect to a width of effective segments that are located nearest to a starting edge and a finishing edge of the reconstruction view area, performs adjustment so that the widths of those effective segments do not protrude from the reconstruction view area, irrespective of the fixed ratio.

5. The radiotomography apparatus according to claim 1, wherein the weight function is a weight function having, with respect to each of the effective segments, a width that is equal to or greater than a width of each effective segment that is centered on a reference segment position of each effective segment.

6. The radiotomography apparatus according to claim 1, wherein the weight function is a function in which weights of each of the adjacent effective segments has an overlap ratio between 0 and 100%, and a sum total of weights in the reconstruction view area is 1.

7. The radiotomography apparatus according to claim 1, wherein the weight function is a weight function in which, when the adjacent effective segment are substantially matching, both segments are used and a sum total of weights assigned to the segments is 1.

8. The radiotomography apparatus according to claim 1, wherein the weight function is a weight function that returns weights of the effective segments to a pre-location $N\pi$ area to perform calculation.

9. The radiotomography apparatus according to claim 1, further comprising reconstruction filtering device that performs reconstruction filtering for the effective segments,
wherein the image creating device creates an image in which effective segments after the reconstruction filtering are reconstructed.

10. The radiotomography apparatus according to claim 1, wherein the image creating device performs cone angle correction prior to the reconstruction.

11. The radiotomography appararus according to claim 1, wherein the image creating device performs realignment processing that realigns a shape of X-ray beams from a fan shape to a parallel shape prior to the reconstruction.

12. The radiotomography apparatus according to claim 1, wherein the image creating device creates an image by reconstruction according to a weighted three-dimensional back projection method using the weight function.

13. The radiotomography apparatus according to claim 1, wherein:
the radiation detection device has a plurality of detector rows in a body axis direction of an object to be examined, and
the effective segment calculating device performs extrapolation of data that is obtained with the plurality of detector rows on at least one side of the radiation detection device in a row direction.

14. A radiotomography apparatus, comprising:
a radiation source including a radiation generating unit that irradiates radiation and a control unit that controls the radiation generating unit;
a radiation detection device that is disposed facing the radiation generating unit to sandwich an object to be examined therebetween, and that detects radiation transmitted through the object to output radiation transmission data;

a rotating device that is equipped with the radiation source and the radiation detection device and is capable of rotation;

a periodic motion data input device that measures a periodic motion of the object and accepts input of periodic motion data that is obtained;

a reconstruction view area determining device that determines a data reconstruction view area based on the input periodic motion;

a reference segment position calculating device that calculates a reference segment position that is located in an arbitrary phase before a reference signal that indicates a phase having a large degree of motion of the object that is included in the periodic motion data;

a relocating device that relocates a reference segment position that is included in the reconstruction view area in a phase corresponding to the reference segment position that is within a range of a natural number multiple of $\pi$;

a segment setting device that sets segments such that, for each of the reference segment positions that are relocated, a starting edge or a finishing edge coincide with the reference segment position;

a weight function calculating device that calculates a weight function that continuously changes such that a sum of weights assigned to adjoining segments in each of the phases that are relocated is constant; and an image creating device that performs reconstruction calculation processing based on the radiation transmission data that is calculated.

15. The radiotomography apparatus according to claim 14, wherein:

the segment setting device sets a segment in which a segment center position is at a reference segment position that is in a phase that is rearward or forward of another reference segment position that corresponds to the starting edge or finishing edge, and that is adjacent at a time of relocation to another reference segment position, and a finishing edge or a starting edge is at a reference segment position that is in a phase that is rearward or forward of the segment center position at a relocation time, and that is adjacent at a relocation time to the segment center position, and the weight function calculating device calculates a weight function such that, in the segment, a weight of the segment center position is highest and a weight of a finishing edge and a starting edge of the segment is lowest.

16. The radiotomography apparatus according to claim 14, wherein the weight function calculating device generates a weight function using a linear function or a non-linear function.

17. A radiotomography apparatus, comprising:

a radiation source including a radiation generating unit that irradiates radiation and a control unit that controls the radiation generating unit;

a radiation detection device that is disposed facing the radiation generating unit to sandwich an object to be examined therebetween, and that detects radiation transmitted through the object to output radiation transmission data;

a rotating device that is equipped with the radiation source and the radiation detection device and is capable of rotation;

a periodic motion data input device that measures a periodic motion of the object and accepts input of periodic motion data that is obtained;

a reconstruction view area determining device that determines a reconstruction view area based on the input periodic motion;

a reference segment position calculating device that calculates a first reference segment position that is located in a phase that fulfills a first condition with respect to a reference signal that indicates a phase having a large degree of motion of an object to be examined that is included in the periodic motion data, and a second reference segment position that is located in a phase that fulfills a second condition with respect to the reference signal;

a relocating device that relocates a first reference segment position and a second reference segment position that are included in the reconstruction view area in a phase corresponding to the first reference segment position and the second reference segment position that is within range or a natural number multiple of $\pi$;

a segment setting device that sets a segment in which the relocated first reference segment position as a segment center position, and at least one of a starting edge and a finishing edge coincides with a first reference segment position or a second reference segment position that is adjacent to the relocated first reference segment position at a relocation time;

a weight function calculating device calculates a weight function that continuously changes so that a sum of weights that are assigned to adjacent segments in each of the phases that is relocated is constant; and an image creating device that performs reconstruction calculation processing based on the radiation transmission data to which the weights are assigned.

18. The radiotomography apparatus according to claim 17, wherein the weight function calculating device generates a weight function using a linear function or a non-linear function.

19. A radiotomography apparatus comprising:

a radiation detection device that detects radiation that is transmitted through an object to be examined from around the object at a predetermined scanning speed;

a table on which the object lies;

a scanning speed control device that can set the predetermined scanning speed of the radiation detection device;

an image creating device that processes the detected radiation to convert resulting data into data segments and create a tomogram;

a heartbeat fluctuation measuring device that measures a heart rate and a heartbeat fluctuation amount of the object;

a reference heartbeat fluctuation calculating device that determines a reference heart rate and a reference heartbeat fluctuation amount based on a heart rate and a heartbeat fluctuation amount that are measured by the heartbeat fluctuation measuring device; and a scanning speed selecting device that selects a scanning speed based on the reference heart rate and the reference heartbeat fluctuation amount than are output from the reference heartbeat fluctuation calculating device, and outputs the scanning speed to the scanning speed control device as the predetermined scanning speed, said scanning speed selecting device comprising;

a first part that stores a correlation function between an effective temporal resolution and a head rate that is decided for each of the scanning speeds, a second part that calculates a series of effective temporal resolution using the correlation function which, for each different scanning speed, stores heart rates within a range of the reference heartbeat fluctuation amount that is centered around the reference heart rate, and a third part that selects the scanning speed based on the calculated series of effective temporal resolution.

20. The radiotomography apparatus according to claim 19, wherein the reference heartbeat fluctuation calculating device determines the reference heart rate as a mean value of at least one part of a heart rate that is measured with the heartbeat fluctuation measuring device, or any one of a center of gravity value, a median value, a weighted additional value and a center of gravity value at a predetermined frequency or more when at least one part of the heart rate is histogrammed.

21. The radiotomography apparatus according to claim 19, wherein the reference heartbeat fluctuation calculating device determines the reference heartbeat fluctuation amount as an interval between a maximum value and a minimum value of at least one part of a heart rate that is measured with the heartbeat fluctuation measuring device, or any one of a width when at least one part of the heart rate is histogrammed, a half-value width, a ¹/₁₀ width or a width at a predetermined frequency or more.

22. The radiotomography apparatus according to claim 19, wherein the device selecting the scanning speed employs a lowest temporal resolution among the series of effective temporal resolutions that are obtained by applying the correlation function as a lowest temporal resolution, determines the lowest temporal resolution for each different scanning speed, and selects a scanning speed at which the lowest temporal resolution is highest.

23. The radiotomography apparatus according to claim 19, wherein the device selecting the scanning speed employs a fluctuation with of the series of effective temporal resolutions that are obtained by applying the correlation function as a temporal resolution fluctuation width that is determined for each different scanning speed, and selects a scanning speed at which the temporal resolution fluctuation width is smallest.

24. The radiotomography apparatus according to claim 19, wherein the device selecting the scanning speed counts a frequency at which the effective temporal resolution occurs taking as a reference a plurality of center of gravity values for each different scanning speed with respect to the series of effective temporal resolutions that are obtained by applying the correlation function, employs a weighted mean value of a center of gravity value of the effective temporal resolution and the occurrence frequency as a mean temporal resolution, and selects a scanning speed at which the mean temporal resolution is highest.

25. The radiotomography apparatus according to claim 19, wherein, when there is a scanning speed that occupies a majority among three scanning speeds consisting of:

a scanning speed at which a lowest temporal resolution is highest when the scanning speed selecting device employs a lowest effective temporal resolution among a series of effective temporal resolutions that are obtained by applying the correlation function as a lowest temporal resolution, and determines the lowest temporal resolution for each different scanning speed;

a scanning speed at which a temporal resolution fluctuation width is smallest when the scanning speed selecting device employs a fluctuation width of a series of effective temporal resolutions that are obtained by applying the correlation function as a temporal resolution fluctuation width that is determined for each different scanning speed; and a scanning speed at which a mean temporal resolution is highest when the scanning speed selecting device counts a frequency at which the effective temporal resolution occurs taking as a reference a plurality of center of gravity values for each different scanning speed with respect to a series of effective temporal resolutions that are obtained by applying the correlation function, and employs a weighted mean value of a center of gravity value of the effective temporal resolution and the occurrence frequency as a mean temporal resolution;

the scanning speed selecting device selects the scanning speed that occupies a majority among the three scanning speeds.

26. The radiotomography apparatus according to claim 19, wherein the heartbeat fluctuation measuring device is a movement amount extracting device that determines a movement amount of a moving body based on an electrocardiograph or the radiation that is detected.

27. The radiotomography apparatus according to claim 19, further comprising an input device that can input from outside change data of a heart rare and a heartbeat fluctuation amount as the basis of a calculation of the reference heart race and the reference heartbeat fluctuation amount, instead of a heart rate and a heartbeat fluctuation amount that are measured by the heartbeat fluctuation measuring device.

28. The radiotomography apparatus according to claim 19, further comprising moving device that is capable of moving at least one member of the group consisting of the radiation detection device and the table in a body axis direction of an object to be examined in a relative manner, and characterized in that the scanning speed control device performs scanning in cooperation with the moving device.

29. A radiotomography apparatus, comprising:

a radiation source including a radiation generating unit that irradiates radiation and a control unit that controls the radiation generating unit;

a radiation detection device that is disposed facing the radiation generating unit to sandwich an object to be examined therebetween, and that detects radiation transmitted through the object to output radiation transmission data;

a rotating device that is equipped with the radiation source and the radiation detection device and is capable of rotation;

a first image creating device that performs reconstruction calculation processing based on the radiation transmission data;

a periodic motion data input device that measures a periodic motion of the object and accepts input of periodic motion data that is obtained;

a reconstruction reference position calculating device that calculates a reconstruction reference position that indicates an arbitrary periodic phase position at which reconstruction is performed, based on the periodic motion data;

a significance calculating device that calculates a significance for each reconstruction reference position that is calculated by the reconstruction reference position calculating device, based on a feature quantity that shows a periodic motion of the object or a time at which the radiation generating unit passes the reconstruction reference position;

an extraction range calculating device that calculates an extraction range in accordance with a significance that is calculated for each of the reconstruction reference positions such that as the significance of a reconstruction reference position increases, the extraction tinge of the radiation transmission data widens for that reconstruction reference position; and a second image creating device that performs reconstruction calculation processing based on the radiation transmission data that is included in the extraction range that is calculated.

30. The radiotomography apparatus according to claim 29, wherein the significance calculating device calculates a significance on the basis of at least one member of the group consisting of: a period of the periodic motion in which the reconstruction reference position is included; time intervals from a time that the radiation generating unit passes the reconstruction reference position until each of the reconstruction reference positions; and a regularity of a periodic motion of the object in which the reconstruction reference position is included.

31. The radiotomography apparatus according to claim 29, wherein the extraction range calculating device calculates an extraction range by assigning predetermined weights to a significance of each reconstruction reference position that is calculated by the significance calculating device.

* * * * *